US010982277B2

(12) United States Patent
Liu et al.

(10) Patent No.: US 10,982,277 B2
(45) Date of Patent: *Apr. 20, 2021

(54) MODIFIED NUCLEOSIDES OR NUCLEOTIDES

(71) Applicant: Illumina Cambridge Limited, Cambridge (GB)

(72) Inventors: Xiaohai Liu, Cambridge (GB); Xiaolin Wu, Cambridge (GB); Geoffrey Paul Smith, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,443

(22) Filed: Sep. 6, 2019

(65) Prior Publication Data

US 2020/0087725 A1 Mar. 19, 2020

Related U.S. Application Data

(63) Continuation of application No. 15/444,826, filed on Feb. 28, 2017, now Pat. No. 10,407,721, which is a continuation of application No. 14/771,481, filed as application No. PCT/EP2013/055466 on Mar. 15, 2013, now Pat. No. 9,593,373.

(51) Int. Cl.
| | |
|---|---|
| *C12Q 1/68* | (2018.01) |
| *C07H 19/073* | (2006.01) |
| *C07H 19/10* | (2006.01) |
| *C07H 19/14* | (2006.01) |
| *C07H 19/173* | (2006.01) |
| *C07H 19/20* | (2006.01) |
| *C12Q 1/6869* | (2018.01) |
| *C12Q 1/6876* | (2018.01) |

(52) U.S. Cl.
CPC ......... *C12Q 1/6869* (2013.01); *C07H 19/073* (2013.01); *C07H 19/10* (2013.01); *C07H 19/14* (2013.01); *C07H 19/173* (2013.01); *C07H 19/20* (2013.01); *C12Q 1/6876* (2013.01); *Y02P 20/55* (2015.11)

(58) Field of Classification Search
CPC .... C12Q 1/6869; C07H 19/073; C07H 19/10; C07H 19/14; C07H 19/173; C07H 19/20
See application file for complete search history.

(56) References Cited

U.S. PATENT DOCUMENTS

| | | |
|---|---|---|
| 4,711,955 A | 12/1987 | Ward et al. |
| 4,772,691 A | 9/1988 | Herman |
| 4,824,775 A | 4/1989 | Dattagupta et al. |
| 4,863,849 A | 9/1989 | Melamede |
| 4,888,274 A | 12/1989 | Radding et al. |
| 4,900,686 A | 2/1990 | Arnost et al. |
| 4,971,903 A | 11/1990 | Hyman |
| 5,047,519 A | 9/1991 | Hobbs, Jr. et al. |
| 5,118,605 A | 6/1992 | Urdea |
| 5,151,507 A | 9/1992 | Hobbs et al. |
| 5,174,962 A | 12/1992 | Brennan et al. |
| 5,175,269 A | 12/1992 | Stavrianopoulos |
| 5,242,796 A | 9/1993 | Prober et al. |
| 5,302,509 A | 4/1994 | Cheeseman |
| 5,328,824 A | 7/1994 | Ward et al. |
| 5,436,143 A | 7/1995 | Hyman |
| 5,449,767 A | 9/1995 | Ward et al. |
| 5,476,928 A | 12/1995 | Ward et al. |
| 5,516,664 A | 5/1996 | Hyman |
| 5,534,424 A | 7/1996 | Uhlen |
| 5,547,839 A | 8/1996 | Dower et al. |
| 5,547,859 A | 8/1996 | Goodman et al. |
| 5,602,000 A | 2/1997 | Hyman |
| 5,635,400 A | 6/1997 | Brenner |
| 5,712,378 A | 1/1998 | Wang |
| 5,728,528 A | 3/1998 | Mathies et al. |
| 5,763,594 A | 6/1998 | Hiatt et al. |
| 5,770,367 A | 6/1998 | Southern et al. |
| 5,798,210 A | 8/1998 | Canard et al. |
| 5,808,045 A | 9/1998 | Hiatt et al. |
| 5,821,356 A | 10/1998 | Khan et al. |
| 5,844,106 A | 12/1998 | Seela et al. |
| 5,849,542 A | 12/1998 | Reeve et al. |
| 5,872,244 A | 2/1999 | Hiatt et al. |
| 5,885,775 A | 3/1999 | Haff et al. |
| 5,959,089 A | 9/1999 | Hannessian |

(Continued)

FOREIGN PATENT DOCUMENTS

| | | |
|---|---|---|
| DE | 4141178 | 6/1993 |
| EP | 0 251 786 | 11/1994 |

(Continued)

OTHER PUBLICATIONS

Bebenek et al., Feb. 25, 1992, The Effects of dNTP Pool Imbalances on Frameshift Fidelity during DNA Replication, The Journal of Biological Chemistry, 267(6):3589-3596.

Bebenek et al., Jul. 1990, Frameshift errors initiated by nucleotide misincorporation, Proc. Natl. Acad. Sci. USA, 87:4946-4950.

Beckman Coulter CEQ(TM) 2000 DNA Analysis System User's Guide, 606913-AC, dated Jun. 2000.

Bentley et al., Nov. 6, 2008, Accurate whole human genome sequencing using reversible terminator chemistry, Nature, 456(7218):53-59.

(Continued)

*Primary Examiner* — Jezia Riley

(74) *Attorney, Agent, or Firm* — Knobbe, Martens, Olson & Bear, LLP

(57) ABSTRACT

Some embodiments described herein relate to modified nucleotide and nucleoside molecules with novel 3'-hydroxy protecting groups. Also provided herein are methods to prepare such modified nucleotide and nucleoside molecules and sequencing by synthesis processes using such modified nucleotide and nucleoside molecules.

21 Claims, 4 Drawing Sheets

(56) References Cited

U.S. PATENT DOCUMENTS

| | | |
|---|---|---|
| 6,001,566 A | 12/1999 | Canard et al. |
| 6,005,125 A | 12/1999 | Zhang et al. |
| 6,008,379 A | 12/1999 | Benson et al. |
| 6,013,445 A | 1/2000 | Albrecht |
| 6,046,005 A | 4/2000 | Ju et al. |
| 6,074,823 A | 6/2000 | Koster |
| 6,087,095 A | 7/2000 | Rosenthal et al. |
| 6,087,112 A | 7/2000 | Dale |
| 6,136,543 A | 10/2000 | Anazawa et al. |
| 6,214,987 B1 | 4/2001 | Hiatt et al. |
| 6,218,118 B1 | 4/2001 | Sampson et al. |
| 6,218,530 B1 | 4/2001 | Rothschild et al. |
| 6,221,592 B1 | 4/2001 | Schwartz et al. |
| 6,232,465 B1 | 5/2001 | Hiatt et al. |
| 6,242,193 B1 | 6/2001 | Anazawa et al. |
| 6,255,083 B1 | 7/2001 | Williams |
| 6,255,475 B1 | 7/2001 | Kwiatkowski |
| 6,287,821 B1 | 9/2001 | Shi et al. |
| 6,309,836 B1 | 10/2001 | Kwiatkowski |
| 6,310,189 B1 | 10/2001 | Fodor et al. |
| 6,312,893 B1 | 11/2001 | Van Ness et al. |
| 6,335,155 B1 | 1/2002 | Wells et al. |
| 6,355,420 B1 | 3/2002 | Chan |
| 6,380,378 B1 | 4/2002 | Kitamura et al. |
| 6,432,360 B1 | 8/2002 | Church |
| 6,451,525 B1 | 9/2002 | Blasband et al. |
| 6,485,944 B1 | 11/2002 | Church et al. |
| 6,524,829 B1 | 2/2003 | Seeger |
| 6,544,797 B1 | 4/2003 | Buechler et al. |
| 6,613,508 B1 | 9/2003 | Van Ness et al. |
| 6,613,523 B2 | 9/2003 | Fischer |
| 6,639,088 B2 | 10/2003 | Kwiatkowski |
| 6,664,079 B2 | 12/2003 | Ju et al. |
| 6,750,357 B1 | 6/2004 | Chiarello et al. |
| 6,780,591 B2 | 8/2004 | Williams et al. |
| 6,787,308 B2 | 9/2004 | Balasubramanian et al. |
| 6,818,395 B1 | 11/2004 | Quake et al. |
| 6,911,345 B2 | 6/2005 | Quake et al. |
| 6,982,146 B1 | 1/2006 | Schneider et al. |
| 7,037,654 B2 | 5/2006 | Chenna et al. |
| 7,037,687 B2 | 5/2006 | Williams et al. |
| 7,056,666 B2 | 6/2006 | Dower et al. |
| 7,057,026 B2 | 6/2006 | Barnes et al. |
| 7,057,031 B2 | 6/2006 | Olenjnik et al. |
| 7,074,597 B2 | 7/2006 | Ju |
| 7,078,499 B2 | 7/2006 | Odedra et al. |
| 7,105,300 B2 | 9/2006 | Parce et al. |
| 7,223,540 B2 | 5/2007 | Pourmand et al. |
| 7,270,951 B1 | 9/2007 | Stemple et al. |
| 7,279,563 B2 | 10/2007 | Kwiatkowski |
| 7,345,159 B2 | 3/2008 | Ju et al. |
| 7,393,533 B1 | 7/2008 | Crotty et al. |
| 6,232,465 C1 | 8/2008 | Hiatt et al. |
| 7,414,116 B2 | 8/2008 | Milton et al. |
| 7,427,673 B2 | 9/2008 | Balasubramanian et al. |
| 5,763,594 C1 | 12/2008 | Hiatt et al. |
| 7,459,275 B2 | 12/2008 | Dower et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 7,713,698 B2 | 5/2010 | Ju et al. |
| 7,771,973 B2 | 8/2010 | Milton et al. |
| 7,772,384 B2 | 8/2010 | Balasubramanian et al. |
| 7,785,790 B1 | 8/2010 | Church et al. |
| 7,785,796 B2 | 8/2010 | Balasubramanian et al. |
| 7,795,424 B2 | 9/2010 | Liu et al. |
| 7,816,503 B2 | 10/2010 | Milton et al. |
| 8,071,739 B2 | 12/2011 | Milton et al. |
| 8,084,590 B2 | 12/2011 | Liu et al. |
| 8,148,064 B2 | 4/2012 | Balasubramanian et al. |
| 8,158,346 B2 | 4/2012 | Balasubramanian et al. |
| 8,394,586 B2 | 3/2013 | Balasubramanian et al. |
| 8,597,881 B2 | 12/2013 | Milton et al. |
| 9,121,060 B2 | 9/2015 | Milton et al. |
| 9,121,062 B2 | 9/2015 | Balasubramanian et al. |
| 9,127,314 B2 | 9/2015 | Liu et al. |
| 9,388,463 B2 | 7/2016 | Balasubramanian et al. |
| 9,388,464 B2 | 7/2016 | Milton et al. |
| 9,410,200 B2 | 8/2016 | Balasubramanian et al. |
| 9,410,199 B2 | 9/2016 | Liu et al. |
| 9,453,258 B2 | 9/2016 | Kain et al. |
| 9,593,373 B2 | 3/2017 | Liu et al. |
| 9,605,310 B2 | 3/2017 | Balasubramanian et al. |
| 10,407,721 B2 * | 9/2019 | Liu .................... C12Q 1/6876 |
| 10,480,025 B2 | 11/2019 | Balasubramanian et al. |
| 10,487,102 B2 | 11/2019 | Liu et al. |
| 10,513,731 B2 | 12/2019 | Milton et al. |
| 2002/0015961 A1 | 2/2002 | Kwiatkowski |
| 2002/0019363 A1 | 2/2002 | Ismail et al. |
| 2003/0008285 A1 | 1/2003 | Fischer |
| 2003/0180769 A1 | 9/2003 | Metzker |
| 2003/0186256 A1 | 10/2003 | Fischer |
| 2004/0014096 A1 | 1/2004 | Anderson et al. |
| 2004/0039189 A1 | 2/2004 | Guimil et al. |
| 2004/0096825 A1 | 5/2004 | Chenna et al. |
| 2010/0159531 A1 | 6/2010 | Gordon et al. |
| 2010/0292452 A1 | 11/2010 | Milton et al. |
| 2010/0323350 A1 | 12/2010 | Gordon |
| 2011/0020827 A1 | 1/2011 | Milton et al. |
| 2011/0124054 A1 | 5/2011 | Olejnik et al. |
| 2012/0052489 A1 | 3/2012 | Gordon et al. |
| 2012/0156671 A1 | 6/2012 | Liu et al. |
| 2012/0252010 A1 | 10/2012 | Balasubramanian et al. |
| 2017/0067104 A1 | 3/2017 | Balasubramanian et al. |
| 2017/0204458 A1 | 7/2017 | Balasubramanian et al. |
| 2020/0017908 A1 | 1/2020 | Milton et al. |
| 2020/0087336 A1 | 3/2020 | Liu et al. |
| 2020/0109448 A1 | 4/2020 | Balasubramanian et al. |
| 2020/0115747 A1 | 4/2020 | Balasubramanian et al. |

FOREIGN PATENT DOCUMENTS

| | | |
|---|---|---|
| EP | 0 992 511 | 4/2000 |
| EP | 1 046 648 | 10/2000 |
| EP | 1 182 267 | 2/2002 |
| EP | 1 291 354 | 3/2003 |
| EP | 0 808 320 | 4/2003 |
| EP | 1 337 541 | 3/2007 |
| EP | 1 218 391 | 4/2007 |
| EP | 1 790 736 | 5/2007 |
| EP | 1 560 838 | 5/2009 |
| EP | 2 119 722 | 11/2009 |
| EP | 2 338 893 | 6/2011 |
| EP | 1 664 287 | 11/2011 |
| EP | 2 325 304 | 5/2012 |
| WO | WO 89/09282 | 10/1989 |
| WO | WO 89/10977 | 11/1989 |
| WO | WO 90/13666 | 11/1990 |
| WO | WO 91/06678 | 5/1991 |
| WO | WO 92/10587 | 6/1992 |
| WO | WO 93/05183 | 3/1993 |
| WO | WO 93/21340 | 10/1993 |
| WO | WO 94/14972 | 7/1994 |
| WO | WO 96/07669 | 3/1996 |
| WO | WO 96/11937 | 4/1996 |
| WO | WO 96/23807 | 8/1996 |
| WO | WO 96/27025 | 9/1996 |
| WO | WO 98/30720 | 7/1998 |
| WO | WO 98/33939 | 8/1998 |
| WO | WO 99/05315 | 2/1999 |
| WO | WO 99/49082 | 9/1999 |
| WO | WO 99/57321 | 11/1999 |
| WO | WO 00/02895 | 1/2000 |
| WO | WO 00/06770 | 2/2000 |
| WO | WO 00/15844 | 3/2000 |
| WO | WO 00/18956 | 4/2000 |
| WO | WO 00/21974 | 4/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | WO 01/16375 | 3/2001 |
| WO | WO 01/23610 | 4/2001 |
| WO | WO 01/25247 | 4/2001 |

(56) References Cited

FOREIGN PATENT DOCUMENTS

| | | |
|---|---|---|
| WO | WO 01/32930 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/022883 | 3/2002 |
| WO | WO 02/29003 | 4/2002 |
| WO | WO 02/072892 | 9/2002 |
| WO | WO 02/079519 | 10/2002 |
| WO | WO 02/088381 | 11/2002 |
| WO | WO 02/088382 | 11/2002 |
| WO | WO 03/002767 | 1/2003 |
| WO | WO 03/020968 | 3/2003 |
| WO | WO 03/048178 | 6/2003 |
| WO | WO 03/048387 | 6/2003 |
| WO | WO 03/085135 | 10/2003 |
| WO | WO 04/007773 | 1/2004 |
| WO | WO 04/018493 | 3/2004 |
| WO | WO 04/018497 | 3/2004 |
| WO | WO 05/084367 | 9/2005 |
| WO | WO 09/054922 | 4/2009 |
| WO | WO 12/083249 | 6/2012 |
| WO | WO 12/162429 | 11/2012 |

OTHER PUBLICATIONS

Bergmann et al., 1995, Allyl as Internucleotide Protecting Group in DNA Synthesis to be Cleaved Off by Ammonia, Tetrahedron, 51(25):6971-6976.

Bi et al., Oct. 20, 2005, Design and Synthesis of a Chemically Cleavable Fluorescent Nucleotide, 3'-O-Allyl-dGTP-allyl-Bodipy-FL-510, as a Reversible Terminator for DNA Sequencing by Synthesis, J. Am. chem. Soc., 128:2542-2543.

Brown et al., 1991, Modern machine-aided methods of oligodeoxyribonucleotide synthesis, Oligonucleotides and Analogues, A Practical Approach, pp. i-ii 1-11, 255.

Brunckova et al., 1994, Intramolecular Hydrogen Atom Abstraction in Carbohydrates and Nucleosides: Inversion of an .alpha.- to .beta.-Manopyranoside and Generation of Thymidine C-4' Radicals, Tetrahedron Letters 35:6619-6622.

Burgess et al., 1997, An Approach to Photolabile, Fluorescent Protecting Groups, J. Org. Chem., 62:5165-5168.

Burns et al., 1991, Selective Reduction of Disulfides by Tris(2-carboxyethyl)phosphine, J. Org. Chem, 56:2648-2650.

Buschmann et al., 2003, Spectroscopic Study and Evaluation of Red-Absorbing Fluorescent Dyes, Bioconjugate Chem. 14:195-204.

Bystrom et al., 1997, ATP Analogs With Non-Transferable Groups in the Y Position as Inhibitors of Glycerol Kinase, Bioorganic & Medicinal Chemistry Letters, 7(20):2613-2616.

Canard et al., 1994, DNA Polymerase Fluorescent Substrates with Reversible 3'-Tags, Gene, 148:1-6.

Canard et al., 1995, Catalytic Editing Properties of DNA Polymerases, Proc. Natl. Acad. Sci., 92:10859-10863.

Chen, Oct. 23, 2015, Incorporation of 3'-Blocked dGTP by Different DNA Polymerases, Illumina, Inc. Protein Engineering Group (iPEG), 8 pp.

Christensen et al., 1972, Specific Chemical Synthesis of Ribonucleoside 0-Benzyl Ethers, J. Org. Chem. 37(22):3398-3401.

Crespo-Hernandez et al., 2000, Part 1. Photochemical and Photophysical Studies of Guanine Derivatives: Intermediates Contributing to its Photodestruction Mechanism in Aqueous Solution and the Participation of the Electron Adduct, Photochemistry and Photobiology, 71(5):534-543.

Dantas et al., 1999, Stannous chloride mediates single strand breaks in plasmid DNA through reactive oxygen species formation, Toxicology Letters 110:129-136.

Dawson et al., 1989, Affinity Isolation of Transcriptionally Active Murine Erythroleukemia Cell DNA Using a Cleavable Biotinylated Nucleotide Analog, The Journal of Biological Chemistry, 264(22):12830-12837.

Dawson et al., 1991, Affinity Isolation of Active Murine Erythroleukemia Cell Chromatin: Uniform Distribution of Ubiquitinated Histone H2A Between Active and Inactive Fractions, Journal of Cellular Biochemistry, 46:166-173.

Definition of VIZ, Merriam-Webster's Collegiate Dictionary, 10th edition, 1997, p. 1316.

Definitions of viz, The Oxford English Dictionary 1989; The Chambers Dictionary 1993; The Longman Dictionary of Contemporary English 2009.

Fersht et al., Jul. 1981, DNA polymerase accuracy and spontaneous mutation rates: Frequencies of purinepurine, purinepyrimidine, and pyrimidine pyrimidine mismatches during DNA replication, Proc. Natl. Acad. Sci. USA, 78(7):4251-4255.

Fersht et al., Oct. 1979, Fidelity of replication of phage OX174 DNA by DNA polymerase III holoenzyme: Spontaneous mutation by misincorporation, Proc. Natl. Acad. Sci. USA, 76(10):4946-4950.

For Authors, Getting published in Nature: the editorial process, nature.com, 2014, 7 pp.

Fuchs, 2011, Handbook of Reagents for Organic Synthesis, Reagents for Silicon-Mediated Organic Synthesis, Purdue University, West Lafayette, IN, USA John Wiley & Sons Ltd, pp. i-iv, 325-336.

Furman et al., Nov. 1986, Phosphorylation of 3'-azido-3'-deoxythymidine and selective interaction of the 5'-triphosphate with human immunodeficiency virus reverse transcriptase, Proc. Natl. Acad. Sci. USA, 83(Medical Sciences):8333-8337.

Gardner et al., 1999, Determinants of nucleotide sugar recognition in an archaeon DNA polymerase, Nucleic Acids Research, 27(12): 2545-2553.

Greene et al., 1999, Protective Groups in Organic Synthesis, Third Edition, John Wiley & Sons, Inc., Chapter 2 (pp. 17-245), Chapter 3 (pp. 246-292), Chapter 10 (pp. 701-723).

Greene et al., 1999, The Role of Protective Groups in Organic Synthesis, Protective Groups in Organic Synthesis, Third Edition, John Wiley & Sons, Inc. Chapter 1, pp. 1-16.

Greene et al., 1999, The Role of Protective Groups in Organic Synthesis, Protective Groups in Organic Synthesis, Third Edition, John Wiley & Sons, Inc., pp. 413, 417, 474, 542-543, 574-576, 749-779.

Guibe et al., 1997, Allylic Protecting Groups and Their Use in a Complex Environment, Part I: Allylic Protection of Alcohols, Tetrahedron, 53(40):13509-13556.

Guibe et al., 1998, Allylic Protecting Groups and Their Use in a Complex Environment, Part II: Allylic Protecting Groups and Their Removal Through Catalytic Palladium pi-Allyl Methodology, Tetrahedron, 54(13):2967-3042.

Guiller et al., 2000, Linkers and cleavage Strategies in Solid-Phase Organic Synthesis and Combinatorial Chemistry, Chem. Rev. 100, pp. 2091-2157.

Guo et al., 2008, Four-color DNA sequencing with 3'-O-modified nucleotide reversible terminators and chemically cleavable fluorescent dideoxynucleotides, PNAS, 105(27):9145-9150.

Guo, 2009, Molecular Engineering of Novel Nucleotide Analogues for DNA Sequencing and Analysis, Thesis, Columbia University.

Handlon et al., 1988, Thiol Reduction of 3'-Azidothymidine to 3'-Aminothymidine: Kinetics and Biomedical Implications, Pharm. Res. 5(5): 297-99.

Hanlon, 1966, The Importance of London Dispersion Forces in the Maintenance of the Deoxyribonucleic Acid Helix, Biochemical and Biophysical Research Communications, 23(6): 861-867.

Hayakawa et al., 1986, Allyl and allyloxycalbonyl groups as versatile protecting groups in nucleotide synthesis, Nucleic Acids Research, Symposium Series No. 17, pp. 97-100.

Hayakawa et al., 1987, A general approach to nucleoside 3'- and 5'-monophosphates, Tetrahedron Letters, 28:2259-2262.

Hayakawa et al., 1993, O-Allyl Protection of Guanine and Thymine Residues in Oligodeoxyribonucleotides, J. Organometallic Chemistry, 58:5551-5555.

Henner et al., 1983, Enzyme Action at 3' Termini of Ionizing Radiation-Induced DNA Strand Breaks, J. Biological Chemistry, 258:15198-15205.

(56) References Cited

OTHER PUBLICATIONS

Holtzman et al., Jan. 1982, Electron microscopy of complexes of isolated acetylcholine receptor, biotinyl-toxin, and avidin, Proc. Natl. Acad. Sci. USA, 79:310-314.
Hovinen et al., 1994, Synthesis of 3'-O-(.omega.-Aminoalkoxymethyl)thymidine 5-Triphosphates, Terminators of DNA Synthesis that Enable 3'-Labelling, JCS Perkin Trans I, pp. 211-217.
Ikeda et al., 1995, A Non-Radioactive DNA Sequencing Method Using Biotinylated Dideoxynucleoside Triphospates and .DELTA. Tth DNA Polymerase, DNA Research, 2:225-227.
Iye et al., 1995, Nucleoside Oxazaphospholidines as Novel Synthons in Oligonucleotide Synthesis, J. Org. Chem, 60:5388-5389.
Ju et al., Four-color DNA sequencing by synthesis using cleavable fluorescent nucleotide reversible terminators, PNAS; vol. 103; No. 52, dated Dec. 26, 2006.
Ju et al., Oct. 26, 2006, Four-color DNA sequencing by synthesis using cleavable fluorescent nucleotide reversible terminators, Columbia Genome Center, Columbia University , 19635-19640.
Jung et al., 1978, Conversion of Alkyl Carbamates into Amines via Treatment with Trimethylsilyl Iodide, J.C.S. Chem. Comm., 7:315-316.
Kamal et al., 1999, A Mild and Rapid Regeneration of Alcohols from Their Allylic Ethers by Chlorotrimethylsilane/Sodium Iodide, Tetrahedron Letters, 40:371-372.
Katagiri et al., 1995, Selective Protection of the Primary Hydroxyl Groups of Oxetanocn A and Conformational Analysis of O-Protected Oxetanocin A1, Chem. Pharm. Bull., 43(5):884-886.
Kim, 2008, Four-Color DNA Sequencing by Synthesis on a Chip Using Cleavable Fluorescent Nucleotide Reversible Terminators, Thesis, Columbia University.
Kit, 1963, Deoxyribonucleic Acids, Division of Biochemical Virology, Baylor University College of Medicine, Houston Texas, Annu. Rev. Biochem, pp. 43-82.
Kitamura et al., 2002, (P(C6H5)3)CpRu+-Catalyzed Deprotection of Allyl Carboxylic Esters, J. Organic Chemistry, 67(14):4975-4977.
Klausner, 19987, Dupont's DNA Sequencer uses new chemistry, Nat. Biotech. 5:1111-1112.
Kloosterman et al., 1985, The Relative Stability of Allyl Ether, Allyloxycarbonyl Ester and Prop-2 Enylidene Acetal Protective Groups Toward Iridium, Rhodium and Palladium Catalysts, Tetrahedron Letters, 26(41):5045-5048.
Knapp et al., 2008, Synthesis of four colors flourescently labelled 3'-0-blocked nucleotides with fluoride cleavable blocking group and linker for array based sequencing-by-synthesis applications, Nucleic Acids Symposium Series, 52:345-346.
Kocienski, 1994, Protecting Groups, Georg Tieme Verlag, Stuttgart, pp. 61-68.
Kraevskii et al., 1987, Substrate Inhibitors of DNA Biosynthesis, Molecular Biology, 21:25-29.
Kraevskii et al., 1987, Substrate Inhibitors of DNA Biosynthesis, Translated from Molekulyarnaya Biologiya (Moscow) (Molecular Biology) 21(1):33-38.
Krecmerova et al., 1990, Synthesis of 5'-O-Phosphonomethyl Derivatives of Pyrimidine 2'-Deoxynucleosides, Collect. Czech. Chem. Commun. 55:2521-2536.
Kurata et al., 2001, Fluorescent Quenching-Based Quantitative Detection of Specific DNA/RNA Using a BODIPY.RTM. FL-Labeled Probe or Primer, Nucleic Acids Research, 29(6):E34.
Kvam et al., 1994, Characterization of Singlet Oxygen-Induced Guanine Residue Damage After Photochemical Treatment of Free Nucleosides and DNA, Biochimica et Biophysica Acta., 1217:9-15.
Lee et al., May 1981, Unwinding of double-stranded DNA helix y dehydration, Proc. Natl. Acad. Sci. USA, 78(5):2838-2842.
Letsinger et al., 1964, 2,4-Dinitrobenzenesulfenyl as a Blocking Group for Hydroxyl Functions in Nucleosides, J. Org. Chem. 29:2615-2618.
Li et al., 2003, A Photocleavable Fluorescent Nucleotide for DNA Sequencing and Analysis, Proc. Natl. Acad. Sci. 100:414-419.

Loubinoux et al., 1988, English Translation of Protection of Phenols by the Azidomethylene Group Application to the Synthesis of Unstable Phenols, Tetrahedron, 44(19):6055-6064.
Lukesh et al., 2012, A Potent, Versatile Disulfide-Reducing Agent from Aspartic Acid, Jounal of the American Chemical Society, 134:4057-4059.
Maier et al., 1995, Synthesis and Properties of New Fluorescein-Labeled Oligonucleotides, Nucleosides & Nucleotides, 14:961-965.
Mardis, Feb. 10, 2011, A decade's perspective on DNA sequencing technology, Nature; 470:198-203 Perspective; doi:10.1038/nature09796.
Markiewicz et al., 1997, A New Method of Synthesis of Fluorescently Labelled Oligonucleotides and Their Application in DNA Sequencing, Nucleic Acids Research, 25:3672-3680.
Marquez et al., 2003, Selective Fluorescence Quenching of 2,3-Diazabicyclo(2.2.2)oct-2-ene by Nucleotides, Organic Letters, 5:3911-3914.
Matsumoto et al., 1968, A Revised Structure of Pederin, 60 Tetrahedron Letters, 60:6297-6300.
Maxam et al., Feb. 1, 1977, A new method for sequencing DNA, Proceedings of the National Academy of Sciences, 74(2):560-564.
Meinwald, 1977, An Approach to the Synthesis of Pederin, Pure and Appl. Chem., vol. 49, Pergoamon Press, pp. 1275-1290.
Meng et al., 2006, Design and Synthesis of a Photocleavable Fluorescent Nucleotide 3'-O-Allyl-dGTP-PC-Bodipy-FL-510 as a Reversible Terminator for DNA Sequencing by Synthesis, JOC, 71:3248-3252.
Meng, 2006, Part 1. Tandem Aldol-Allylation Reactions Promoted by Strained Silacycles, PartII. Design and Synthesis of Modified Fluorescent Nucleotides for DNA Sequencing by Synthesis, Columbia Uuniversity.
Merck Index, The, 2001, Entry for Phenol, an Encyclopedia of Chemicals, Drugs, and Biologicals, 13th Ed., pp. 1299-1300.
Merck Index, The, 2001, Entry for Triphenylphosphine, an Encyclopedia of Chemicals, Drugs, and Biologicals, 13th Ed., p. 1735.
Metzker, 1994, Termination of DNA Synthesis by Novel 3'-Modified-Deoxyribonucleoside 5'-Triphosphases, Nucleic Acids Research, 22(20):4259-4267.
Metzker, 2005, Emerging technologies in DNA sequencing, Genome Research, 15:1767-1776.
Metzker, 2010, Sequencing Technologies—The Next Generation, Nature Reviews Genetics, 11:31-46.
Mitra et al., 2002, Fluorescent in situ sequencing on polymerase colonies, Analytical Biochemistry, Academic Press, San Diego US, 320(1):55-65.
Mitra et al., 2003, Supplementary Information for Fluorescent in situ Sequencing on Polymerase Colonies, Analytical Biochemistry, pp. 1-19.
Mullis et al., 1987, Specific Synthesis of DNA in Vitro via a Polymerase-Catalyzed Chain Reaction, Methods in Enzymology, vol. 155, Rec0mbinant DNA, part F, 19 pp.
Mungall et al., 1975, Use of the Azido Group in the Synthesis of 5' Terminal Aminodeoxythymidine Oligonucleotides, J. Org. Chem., 40(11):1659-1662.
Murakami et al., 1990, Structure of a Plasmodium yoelii gene-encoded protein homologiys to the Ca2+-ATPase of rabbit skeletal muscle sarcoplasmic reticulum, J. Cell Sci. 97:487-95.
Mussini et al., 1985, Criteria for standardization of pH measurements in organic solvents and water + organic solvent mixtures of moderate to high permittivities, Pure & Appl. Chem., 57(6):865-876.
Nazarenko et al., 2002, Effect of Primary and Secondary Structure of Oligodeoxyribonucleotides on the Fluorescent Properties of Conjugated Dyes, Nucleic Acids Research, 30:2089-2095.
Nishino et al., 1991, Efficient Deanilidation of Phosphoranilidates by the Use of Nitrites and Acetic/Anhydride, Heteroatom Chemistry, 2:187-196.
Oksman et al., 1991, Conformation of 3'-Substituted 2', 3'-Dideoxyribonucleosides in Aqueous Solution: Nucleoside Analogs with Potential Antiviral Activity, Nucleosides & Nucleotides, 10(1-3):567-568.
Oksman et al., 1992, Solution Conformations and Hydrolytic Stability of 2'- and 3'-Substituted 2', 3'Dideoxyribonucleosides, Includ-

(56) References Cited

OTHER PUBLICATIONS ing Some Potential Inhibitors of Human Immunodeficiency Virus, Journal of Physical Organic Chemistry, 5(22):741-747.
Olejnik et al., 1995, Photocleavable Biotin Derivatives: A Versatile Approach for the Isolation of Biomolecules, Proc. Natl. Acad. Sci. 92:7590-7594.
O'Neil et al., The Merck Index, An Encyclopedia of Chemicals, Drugs, and Biologicals, Thirteenth Edition, 2001, p. 9815.
Pierce Chemical Company—1999/2000 Products Catalog, (1999) 48 pages.
Pilard et al., 1984, A stereospecific synthesis of (.+−.) .alpha.-conhydrine and (.+−.) .beta.-conhydrine., Tetrahedron Letters, 25(15):1555-1556.
Prober et al., 1987, A System for Rapid DNA Sequencing with Fluorescent Chain-Terminating Dideoxynucleotides, Science, 238:336-341.
Pugliese et al., 1993, Three-dimensional Structure of the Tetragonal Crystal Form of Egg-white Avidin in its Functional Complex with Biotin at 2 7 A Resolution, J. Mol. Biol., pp. 698-710.
Quaedflieg et al., 1992, An Alternative Approach Towards the Synthesis of (3'.fwdarw.5') Methylene Acetal Linked Dinucleosides, Tetrahedron Letters, 33(21):3081-3084.
Qui C., 2011, Novel Molecular Engineering Approaches for Genotyping and DNA Sequencing, Thesis Columbia University, 282 pages.
Ranganathan et al., 1978, Facile Conversion of Adenosine Into New 2'-Substituted-2'-Deoxy-Arabinofuranosyladenine Derivatives : Stereospecific Synthesis of 2'-Azido-2'-Deoxy-,2'-Amino-Z'-Deoxy-, and 2'-Mercapto-2'-Deoxy-BD-Arabinofuranosyladenine, Tetra. Letts. 45:4341-4344.
Rao et al., 2001, Four Color FRET Dye Nucleotide Terminators for DNA Sequencing, Nucleosides, Nucleotides, & Nucleic Acids, 20:673-676.
Rasolonjatovo 1998, et al., 6-N-(N-Methylanthranylamido)-4-Oxo-Hexanoic Acid: A New Fluorescent Protecting Group Applicable to a New DNA Sequencing Method, Nucleosides & Nucleotides, 17:2021-2025.
Rigas et al., Dec. 1986, Rapid plasmid library screening using RecA-coated biotinylated probes, Proc. Natl. Acad. Sci. USA Genetics, 83:9595.
Ruby et al., 1990, Affinity Chromatography with Biotynlated RNAs, Methods in Enxymology, 181, :97-121.
Ruparel et al., Apr. 26, 2005, Design and synthesis of a 3-O-allyl photocleavable fluorescent nucleotide as a reversible terminator for DNA sequencing by synthesis, PNAS, 102(17):5932-5937.
Sanger et al., Dec. 1977, DNA sequencing with chain-terminating inhibitors, Proc. Natl. Acad. Sci. USA, Biochemistry, 74(12):5463-5467.
Sarfati et al., 1995, Synthesis of Fluorescent Derivatives of 3'-O-(6-Aminohexanoy1)-pyrimidine Nucleosides 5'-Triphosphates that Act as DNA Polymerase Substrates Reversibly Tagged at C-3', JCS Perkin Trans I, 1163-1171.
Seeger, 1998, Single Molecule Fluorescence: High-Performance Molecular Diagnosis and Screening, Bioforum, Git Verlag, Darmstadt, DE, 21(4):179-185 (German text and English translation).
Shen et al., Aug. 1995, RNA structure at high resolution, The FASEB Journal, 9:1023-1033.
Shendure et al., 2004, Advanced sequencing technologies: methods and goals, Nature Rev. Genet., 5:335-344.
Stratagene, 1988, Gene Characterization Kits, p. 39, Catalog.
Taylor et al., 1985, Rise per base pair in helices of double-stranded rotavirus RNA determined by electron microscopy, Virus Research, 2:175-182.
Tietze et al., 1997, Synthesis of a Novel Stable GM.-Lactone Analogue as Hapten for a Possible Immunization Against Cancer, Angew. Chem. Int. Ed. Engl. 36(15):1615-1617.
Torimura et al., 2001, Fluorescence-Quenching Phenomenon by Photoinduced Electron Transfer Between a Fluorescent Dye and Nucleotide Base, Analytical Sciences, 17:155-160.
Treinin, 1971, General and Theoretical Aspects, The Chemistry of the Azido Group, Saul Patai, Ed., Chapter 1, pp. 1-55.

Tsai et al., 2006, Versatile and Efficient Synthesis of a New Class of Aza-Based Phosphinic Amide Ligands via Unusual P—C Cleavage, Helvetica Chimica Acta, 89:3007-3017.
Veeneman et al., 1991, An Efficient Approach to the Synthesis of Thymidine Derivatives Containing Phosphate-Isosteric Methylene Acetal Linkages, Tetrahedron, 47:1547-1562.
Wada et al., 2001, 2-(Azidomethyl)benzoyl as a New Protecting Group in Nucleosides, Tetrahedron Letters, 42:1069-1072.
Watkins et al., 1982, Synthesis of Oligodeoxyribonucleotides Using N-Benzyloxycarbonyl-Blocked Nucleosides, J. Am. Chem. Soc. 104:5702-5708.
Watson et al., 2004, Molecular Biology of the Gene; 5th edition, The Structures of DNA and RNA; Chapter 6, pp. 97-128.
Welch et al., 1999, Syntheses of Nucleosides Designed for Combinatorial DNA Sequencing, Chemistry, European Journal, 5:951-960.
Welch et al., 1999, Synthesis of Fluorescent, Photolabile 3'-O-Protected Nucleoside Triphosphates for the Base Addition Sequencing Scheme, Nucleosides & Nucleotides, 18(2):197-201.
Welch et al., 2005, Corrigenda: Synthesis of Nucleosides Designed for Combinatorial DNA Sequencing, Chem. Eur. J., 11:7145.
Westheimer, Mar. 6, 1987, Why Nature Chose Phosphates, Science, 235:1174-1178, www.sciencemag.org.
WT 9° N can Incorporate ffG Nucleotide, Oct. 23, 2015, 1 page.
Wu et al., 2007, Termination of DNA synthesis by N6-alkylated, not 3'-O-alkylated, photocleavable 2'-deoxyadenosine triphosphates, Nucleic Acids Research, 35(19):6339-6349.
Wu et al., Oct. 16, 2007, 3-O-modified nucleotides as reversible terminators for pyrosequencing, PNAS; 104(42):16462-16467.
Wu, 2008, Molecular Engineering of Novel Nucleotide Analogues for DNA Sequencing by Synthesis, Thesis, Columbia University, 231 pages.
Yamashita et al., 1987, Studies of Antitumor Agents, VII. Antitumor Activities of O-Alkoxyalkyl Derivatives of 2'-Deoxy-5-trifluoromethyluridine, Chem. Pharm. Bull., 35:2373-2381.
Yoshimoto et al., 2001, Tris(2,4,6-trimethoxyphenyl)phosphine (TTMPP): A Novel Catalyst for Selective Deacetylation, Chemistry Letters, Department of Chemistry, Faculty of Science, Kobe University, Kobe 657-8501, 934-935.
Yu, 2010, Novel Strategies to Increase Read Length and Accuracy for DNA Sequencing by Synthesis, Thesis, Columbia University, 196 pages.
Zavgorodny et al., 1991, 1-Alkylthioalkylation of Nucleoside Hydroxyl Functions and its Synthetic Applications, Tetrahedron Letters, 32(51):7593-7596.
Zavgorodny et al., 2000, S,X-Acetals in Nucleoside Chemistry III. Synthesis of 2' and 3'-O-Azidomethyl Derivatives of Ribonucleosides, Nucleosides, Nucleotides & Nucleic Acids, 19(10-12):1977-1991.
Zhang, Development of New DNA Sequencing Approaches and Investigation of Vision-related Proteins Using Synthetic Chemistry, Thesis, Columbia University, 319 pages.
Zimmerman, Mar./Apr. 2014, The Smartest Company in the World. and It's Not Google, MIT Tech Review, 117(2):27-29.
Kilger Submission in reply to the summons to attend oral proceedings dated May 13, 2015, Opposition against EP1530578B1 (EP03792519.5) Patentee: Illumina Cambridge Limited, Opposition by: Dr. Christian Kilger, Oct. 1, 2015, 34 pages.
Declaration of Cheng-Yao Chen, Ph.D., in Opposition Proceedings Relating to European Patent EP1530578 (Application 03792519.2. Illumina Cambridge Limited), Oct. 23, 2015, 5 pages.
Claims—First Auxiliary Request (annotated), In the matter of European Patent No. 1530578 and Opposition thereto filed by Dr Christian Kilger, Oct. 27, 2015, 5 pages.
Claims—First Auxiliary Request (clean), In the matter of European Patent No. 1530578 and Opposition thereto filed by Dr Christian Kilger, Oct. 27, 2015, 5 pages.
Further Written Submissions in preparation for Oral Proceedings on Nov. 6, 2015, In the matter of European Patent No. 1530578 and Opposition thereto filed by Dr Christian Kilger, Oct. 27, 2015, 20 pages.
Declaration of Dr. Jorn Glokler, In the matter of European Patent No. 1530578 and Opposition thereto filed by Dr Christian Kilger, Nov. 2, 2015, 16 pages.

(56) References Cited

OTHER PUBLICATIONS

Decision rejecting the opposition (Art. 101(2) EPC), In the matter of European Patent No. 1530578 and Opposition thereto filed by Dr Christian Kilger, Dec. 9, 2015, 23 pages.
Provision of the minutes in accordance with Rule 124(4) EPC, Minutes of the oral proceedings before the Opposition Division, EP Application No. 03792519.5 (EP Patent No. 1530578), Dec. 9, 2015, 14 pages.
Communication from Illumina Cambridge Limited to EPO re Minutes of the Oral Proceedings held Nov. 6, 2015;, Opposition to EP1530578 by Dr. Christian Kilger, mailed Dec. 16, 2015.
International Search Report and Written Opinion for Application No. PCT/EP2013/055466, dated Oct. 29, 2013.
IPR2013-00128, "English Translation of WO98/33939", dated Aug. 6, 1998 and declaration of Ryan Drost.
IPR2013-00128, "Excerpts from the file history of European Patent Application No. 02781434.2", Aug. 16, 2006.
IPR2013-00128, "Amended Complaint for Patent Infringement", dated Apr. 11, 2012.
IPR2013-00128, "Petition for Inter Partes Review of U.S. Pat. No. 7,713,698", dated Sep. 16, 2012.
IPR2013-00128, "Petition for Inter Partes Review of U.S. Pat. No. 7,790,869", dated Sep. 16, 2012.
IPR2013-00128, "Petition for Inter Partes Review of U.S. Pat. No. 8,088,575", dated Oct. 3, 2012.
IPR2013-00128, "Proposed Protective Order in *the Trustees of Columbia University in the City of New York v. Illumina, Inc.*", Dec. 12, 2012.
IPR2013-00128, "Columbia University's Answer to Illumina's Amended Counterclaims for Declaratory Judgment", dated Jan. 7, 2013.
IPR2013-00128, "Declaration of Dr. Bruce Branchaud in Support of Petition for Inter Partes Review of U.S. Pat. No. 7,057,026", Jan. 28, 2013, 1-41.
IPR2013-00128, "Exhibit List", dated Jan. 29, 2013.
IPR2013-00128, "Petition for Inter Partes Review of U.S. Pat. No. 7,057,026", dated Jan. 29, 2013.
IPR2013-00128, "Power of Attorney and Certificate of Service", dated Jan. 29, 2013.
IPR2013-00128, "Order (Regarding Conference Call)", dated Jan. 31, 2013.
IPR2013-00128, "ERRATA", dated Feb. 1, 2013.
IPR2013-00128, "Notice of Filing Date Accorded to Petition and Time for Filing Patent Owner Preliminary Response", dated Feb. 1, 2013.
IPR2013-00128, "Intelligent Bio-Systems' Response to Order", dated Feb. 7, 2013.
IPR2013-00128, "Revised Petition for Inter Partes Review of U.S. Pat. No. 7,057,026", dated Feb. 7, 2013.
IPR2013-00128, "Illumina Cambridge Limited Mandatory Notices", Feb. 18, 2013.
IPR2013-00128, "Illumina Cambridge Limited's Power of Attorney in an Inter Partes Review", dated Feb. 18, 2013.
IPR2013-00128, "Columbia University's Response to Illumina's Requests for Admission", dated Apr. 8, 2013.
IPR2013-00128, "Intelligent Bio-Systems, Inc.'s Responses to Illumina, Inc.'s First Set of Requests for Admission to IBS", dated Apr. 8, 2013.
IPR2013-00128, "Petitioner's Motion for Admission Pro Hac Vice of Robert R. Baron, Jr.", dated Apr. 16, 2013.
IPR2013-00128, "Decision", dated Apr. 26, 2013.
IPR2013-00128, "Illumina Cambridge Ltd Preliminary Response", dated May 1, 2013.
IPR2013-00128, "Declaration of Dr. Bruce P. Branchaud in Support of Petition for Inter Partes Review of U.S. Pat. No. 7,057,026", dated Jun. 4, 2013.
IPR2013-00128, "Decision Institution of Inter Partes Review", dated Jul. 29, 2013.
IPR2013-00128, "Decision", dated Jul. 29, 2013.
IPR2013-00128, "Scheduling Order", dated Jul. 29, 2013.

IPR2013-00128, "Curriculum Vitae Floyd Eric Romesberg", dated Aug. 2013.
IPR2013-00128, "Order Conduct of the Proceeding", dated Aug. 14, 2013.
IPR2013-00128, "Intelligent Bio-Systems Inc.'s List of Proposed Motions", dated Aug. 27, 2013.
IPR2013-00128, "Patent Owner Illumina's Proposed Motions", dated Aug. 27, 2013.
IPR2013-00128, "Order Conduct of the Proceeding", dated Aug. 29, 2013.
IPR2013-00128, "Illumina Motion for Counsel to Withdraw From the Proceeding to Permit Substitution of Counsel", dated Aug. 30, 2013.
IPR2013-00128, "Decision Motion to Withdraw", dated Sep. 10, 2013.
IPR2013-00128, "Declaration of William R. Zimmerman in Support of Motion to Appear Pro Hac Vice on Behalf of Patent Owner Illumina Cambridge Ltd.", dated Sep. 11, 2013.
IPR2013-00128, "Illumina's First Supplemental Mandatory Notices", dated Sep. 11, 2013.
IPR2013-00128, "Illumina Cambridge Limited's Updated Power of Attorney in an Inter Partes Review", dated Sep. 16, 2013.
IPR2013-00128, "Order Conduct of the Proceeding", dated Sep. 16, 2013.
IPR2013-00128, "Illumina's Second Supplemental Mandatory Notices", dated Sep. 17, 2013.
IPR2013-00128, "Intelligent Bio-System, Inc.'s Current Exhibit List", dated Sep. 17, 2013.
IPR2013-00128, "Transcript of Initial Conference Call Held on Aug. 29, 2013", dated Sep. 17, 2013.
IPR2013-00128, "Illumina Notice of Cross-Examination Deposition of IBS Declarant Dr. Bruce P. Branchaud", dated Sep. 19, 2013.
IPR2013-00128, "Illumina Updated Exhibit List", dated Sep. 23, 2013.
IPR2013-00128, "Motion for William R. Zimmerman to Appear Pro Hac Vice on Behalf of Patent Owner Illumina Cambridge Ltd.", dated Sep. 23, 2013.
IPR2013-00128, "Patent Owner Illumina's Additional Power of Attorney", dated Sep. 23, 2013.
IPR2013-00128, "Decision Illumina's Motion for Pro Hac Vice Admission of William R. Zimmerman", dated Oct. 1, 2013.
IPR2013-00128, "Illumina Supplemental Mandatory Notice: Additional Backup Counsel", dated Oct. 1, 2013.
IPR2013-00128, "Signed Deposition Transcript of Dr. Bruce Branchaud", dated Oct. 3, 2013.
IPR2013-00128, "Deposition Transcript of Bruce Branchaud, Ph.D. held on Oct. 3, 2013", dated Oct. 8, 2013.
IPR2013-00128, "Order Conduct of the Proceeding", dated Oct. 22, 2013.
IPR2013-00128, "Declaration of Eric Vermaas Accompanying Patent Owner's Motion to Amend", dated Oct. 24, 2013.
IPR2013-00128, "Declaration of Floyd Romesberg, Ph.D.", dated Oct. 24, 2013.
IPR2013-00128, "Illumina Motion to Seal", dated Oct. 24, 2013.
IPR2013-00128, "Illumina Updated Exhibit List", dated Oct. 24, 2013.
IPR2013-00128, "Illumina's Motion to Amend", dated Oct. 24, 2013.
IPR2013-00128, "List of Documents Considered by Floyd Romesberg, Ph.D., in Preparing Declaration", dated Oct. 24, 2013.
IPR2013-00128, "U.S. Pat. No. 7,057,026 File History", dated Oct. 24, 2013.
IPR2013-00128, "Declaration of Jason P. Grier in Support of Petitioner's Motion for Admission Pro Hac Vice of Jason P. Grier", dated Dec. 23, 2013.
IPR2013-00128, "Intelligent Bio-System, Inc.'s Current Exhibit List", dated Dec. 23, 2013.
IPR2013-00128, "Intelligent Bio-Systems' Notice of Cross-Examination Deposition of Illumina's Declarant Dr. Floyd Romesberg", dated Dec. 23, 2013.
IPR2013-00128, "Intelligent Bio-Systems' Notice of Cross-Examination Deposition of Illumina's Declarant Mr. Eric Vermaas", dated Dec. 23, 2013.

(56) References Cited

OTHER PUBLICATIONS

IPR2013-00128, "Petitioner's Motion for Admission Pro Hac Vice of Jason P. Grier", dated Dec. 23, 2013.
IPR2013-00128, "Decision IBS's Motion for Pro Hac Vice Admission of Jason P. Grier", dated Jan. 10, 2014.
IPR2013-00128, "Transcript of Video Deposition of Eric Vermaas", Jan. 14, 2014.
IPR2013-00128, "Intelligent Bio-System, Inc.'s Current Exhibit List Under 37 C.F.R. § 42.63", dated Jan. 24, 2014.
IPR2013-00128, "Intelligent Bio-System, Inc.'s Current Exhibit List", Jan. 24, 2014.
IPR2013-00128, "Petitioner Intelligent Bio-Systems, Inc.'s Motion to Seal", Jan. 24, 2014.
IPR2013-00128, "Petitioner Intelligent Bio-Systems, Inc.'s Opposition to Illumina's Motion to Amend", Jan. 24, 2014.
IPR2013-00128, "Second Declaration of Dr. Bruce Branchaud in Support of Intelligent Bio-Systems, Inc.'s Opposition to Illumina's Motion to Amend", dated Jan. 24, 2014.
IPR2013-00128, "Substitute Declaration of Eric Vermaas Accompanying Patent Owner's Motion to Amend—Redacted", dated Jan. 24, 2014.
IPR2013-00128, "Substitute Declaration of Floyd Romesberg, Ph.D., in Support of Patent Owner's Motion to Amend", Jan. 24, 2014.
IPR2013-00128, "Transcript of Video Deposition of Floyd Romesberg, Ph.D.", Jan. 24, 2014.
IPR2013-00128, "Supplementary Information for Exhibit 1032", dated Jan. 27, 2014.
IPR2013-00128, "Illumina Notice of Cross-Examination Deposition of IBS Declarant Dr. Bruce P. Branchaud", Jan. 31, 2014.
IPR2013-00128, "Order Conduct of the Proceeding", Jan. 31, 2014.
IPR2013-00128, "Patent Owner's Unopposed Motion to File Substitute Declarations of Eric Vermaas and Floyd Romesberg, Ph.D., and to File Substitute Motion to Amend", Jan. 31, 2014.
IPR2013-00128, "Branchaud Second Depo Transcript", Dated Feb. 11, 2014.
IPR2013-00128, "Decision Patent Owner's Motion to File Substitute Declarations and Substitute Motion to Amend", dated Feb. 19, 2014.
IPR2013-00128, "Illumina Updated Exhibit List", dated Feb. 19, 2014.
IPR2013-00128, "Illumina's Substitute Motion to Amend Under 37 C.F.R. § 42.121", dated Feb. 19, 2014.
IPR2013-00128, "Redlined Version—Illumina Motion to Amend", dated Feb. 19, 2014.
IPR2013-00128, "Redlined Version—Redacted Vermaas Declaration", dated Feb. 19, 2014.
IPR2013-00128, "Redlined Version—Romesberg Declaration", dated Feb. 19, 2014.
IPR2013-00128, "Substitute Declaration of Eric Vermaas Accompanying Patent Owner's Motion to Amend", dated Feb. 19, 2014.
IPR2013-00128, "Substitute Declaration of Floyd Romesberg, Ph.D., In Support of Patent Owner's Motion to Amend", dated Feb. 19, 2014.
IPR2013-00128, "Vermaas signature page and errata for Jan. 13, 2014 depo transcript", dated Feb. 19, 2014.
IPR2013-00128, "Romesberg signature page and errata for Jan. 14, 2014 depo transcriipt", dated Feb. 23, 2014.
IPR2013-00128, "File history excerpts from U.S. Appl. No. 10/285,010", dated Feb. 24, 2014.
IPR2013-00128, "Illumina Updated Exhibit List", dated Feb. 24, 2014.
IPR2013-00128, "Patent Owner Illumina's Reply to Petitioner's Opposition to Illumina's Motion to Amend", dated Feb. 24, 2014.
IPR2013-00128, "Intelligent Bio-System's Objections to Illumina's Exhibits Submitted With Its Reply to Petitioner's Opposition to Illumina's Motion to Amend", dated Mar. 3, 2014.
IPR2013-00128, "Declaration of Adrienne Stephens", dated Mar. 17, 2014.
IPR2013-00128, "Illumina Updated Exhibit List", dated Mar. 18, 2014.
IPR2013-00128, "Illumina's Motion to Exclude IBS Evidence", dated Mar. 18, 2014.
IPR2013-00128, "Illumina's Request for Oral Argument", dated Mar. 18, 2014.
IPR2013-00128, "Intelligent Bio-System, Inc.'s Current Exhibit List Under 37 C.F.R. § 42.63", dated Mar. 18, 2014.
IPR2013-00128, "Petitioner Intelligent Bio-Systems, Inc.'s Motion to Exclude Evidence", dated Mar. 18, 2014.
IPR2013-00128, "Petitioner Intelligent Bio-Systems, Inc.'s Request for Oral Argument", dated Mar. 18, 2014.
IPR2013-00128, "Branchaud Signature page and Errata for Feb. 11, 2014 Deposition Transcript", dated Mar. 21, 2014.
IPR2013-00128, "Illumina Appendix of Authority for Its Opposition to IBS Motion to Exclude Evidence", dated Mar. 31, 2014.
IPR2013-00128, "Intelligent Bio-System, Inc.'s Current Exhibit List Under 37 C.F.R. § 42.63", dated Mar. 31, 2014.
IPR2013-00128, "Intelligent Bio-Systems, Inc.'s Opposition to Illumina's Motion to Exclude IBS Evidence", dated Mar. 31, 2014.
IPR2013-00128, "Order Trial Hearing", dated Mar. 31, 2014.
IPR2013-00128, "Petitioner Intelligent Bio-Systems, Inc.'s Supplemental Mandatory Notice: Additional Backup Counsel", dated Apr. 4, 2014.
IPR2013-00128, "Power of Attorney and Certificate of Service", dated Apr. 4, 2014.
IPR2013-00128, "Illumina Appendix of Authority for Its Reply to IBS Opposition to Illumina Motion to Exclude Evidence", dated Apr. 7, 2014.
IPR2013-00128, "Illumina Reply to IBS Opposition to Motion to Exclude", dated Apr. 7, 2014.
IPR2013-00128, "Petitioner Intelligent Bio-Systems, Inc.'s Reply to Illumina's Opposition to Intelligent Bio-Systems, Inc.'s Motion to Exclude Evidence", dated Apr. 7, 2014.
IPR2013-00128, "Order Conduct of the Proceeding", dated Apr. 11, 2014.
IPR2013-00128, "Inter Partes Review—Petitioner Power of Attorney", dated Apr. 15, 2014.
IPR2013-00128, "Intelligent Bio-System, Inc.'s Current Exhibit List Under 37 C.F.R. § 42.63", dated Apr. 16, 2014.
IPR2013-00128, "Intelligent Bio-Systems, Inc.'s Demonstratives for Apr. 23, 2014 Oral Argument", dated Apr. 16, 2014.
IPR2013-00128, "Illumina Demonstratives for Oral Argument", dated Apr. 21, 2014.
IPR2013-00128, "Illumina Notice of Filing Its Demonstratives for Oral Hearing", dated Apr. 21, 2014.
IPR2013-00128, "Illumina Updated Exhibit List", dated Apr. 21, 2014.
IPR2013-00128 # 1, "Proceedings", Apr. 23, 2014.
IPR2013-00128 # 2, "Decision, Motion to Seal", Jun. 4, 2014.
IPR2013-00128 # 3, "Petitioner Intelligent Bio-Systems, Inc.'s Updated Mandatory Notice of Counsel", Jun. 6, 2014.
IPR2013-00128 # 4, "Final Written Decision", Jul. 25, 2014.
IPR2013-00128 # 5, "Decision, Request to Preserve Recording Pending Appeal", Sep. 10, 2014.
IPR2013-00128 # 6, "Renewed Motion for Attorneys to Withdraw as Backup Counsel for Illumina", Sep. 23, 2014.
IPR2013-00128 # 7, "Illumina Notice of Appeal in the U.S. Court of Appeals for the Federal Circuit", Sep. 24, 2014.
IPR2013-00128 # 8, "Decision, Motion to Withdraw", Oct. 7, 2014.
IPR2013-00128 # 9, "Petitioner Intelligent Bio-Systems, Inc.'s Supplemental Mandatory Notice: Additional Backup Counsel", Jun. 3, 2014.
IPR2013-00128 # 10, "Illumina Revocation of Power of Attorney for James G. Morrow and James D. Borchardt", Oct. 27, 2014.
IPR2013-00128, "Excerpts from the '026 file history", 2004-2005.
IPR2013-00128, "ScanArray Express Brochure", 2002, 11 pages.
IPR2013-00266, *"The Trustees of Columbia University in the City of New York v. Illumina, Inc."*, 1:12-cv-00376-GMS (D.Del.), Columbia's Amended Complaint, Doc. 5, dated Apr. 11, 2012.
IPR2013-00266, "Petition for Inter Partes Review of U.S. Pat. No. 7,713,698", dated Sep. 16, 2012.
IPR2013-00266, "Petition for Inter Partes Review of U.S. Pat. No. 7,790,869", dated Sep. 16, 2012.

(56) References Cited

OTHER PUBLICATIONS

IPR2013-00266, "Illumina's Second Supplemental Mandatory Notices", dated Sep. 17, 2013.
IPR2013-00266, "Petition for Inter Partes Review of U.S. Pat. No. 8,088,575", dated Oct. 3, 2012.
IPR2013-00266, "Proposed Protective Order", dated Dec. 21, 2012.
IPR2013-00266, "*The Trustees of Columbia University in the City of New York v. Illumina, Inc.*", 1:12-cv-00376-GMS (D.Del.) Columbia's Answer to Illumina's Amended Counterclaims for Declaratory Judgment, Doc. 72, Jan. 7, 2013.
IPR2013-00266, "Illumina Notice of Cross-Examination Deposition of IBS Declarant Dr. Bruce Branchaud", dated Mar. 4, 2013.
IPR2018-00266, "Declaration of Dr. Bruce P. Branchaud in Support of Petition for Inter Partes Review of U.S. Pat. No. 8,158,346", dated May 3, 2013.
IPR2013-00266, "Excerpts from the '346 Patent File History", dated May 4, 2013.
IPR2013-00266, "Exhibit List", dated May 4, 2013.
IPR2013-00266, "Inter Partes Review—Petitioner Power of Attorney", dated May 4, 2013.
IPR2013-00266, "Petition for Inter Partes Review of U.S. Pat. No. 8,158,346", dated May 4, 2013.
IPR2013-00266, "Notice of Filing Date Accorded to Petition and Time for Filing Patent Owner Preliminary Response", dated May 8, 2013.
IPR2013-00266, "Illumina Cambridge Limited Mandatory Notices", dated May 24, 2013.
IPR2013-00266, "Illumina Cambridge Limited's Power of Attorney in an Inter Partes Review", dated May 24, 2013.
IPR2013-00266, "Declaration of Robert R. Baron, Jr. in Support of Petitioner's Motion for Admission Pro Hac Vice of Robert R. Baron, Jr.", dated Jul. 19, 2013.
IPR2013-00266, "Petitioner's Motion for Admission Pro Hac Vice of Robert R. Baron, Jr", dated Jul. 19, 2013.
IPR2013-00266, "Illumina Cambridge Ltd Preliminary Response", dated Aug. 5, 2013.
IPR2013-00266, "Decision Intelligent Bio-Systems' Motion for Pro Hac Vice Admission of Robert R. Baron, Jr.", dated Aug. 9, 2013.
IPR2013-00266, "Order Conduct of Proceeding", dated Aug. 29, 2013.
IPR2013-00266, "Illumina Motion for Counsel to Withdraw From the Proceeding to Permit Substitution of Counsel", dated Aug. 30, 2013.
IPR2013-00266, "Decision Motion to Withdraw", dated Sep. 10, 2013.
IPR2013-00266, "Illumina's First Supplemental Mandatory Notices", dated Sep. 11, 2013.
IPR2013-00266, "Illumina Cambridge Limited's Updated Power of Attorney in an Inter Partes Review", dated Sep. 16, 2013.
IPR2013-00266, "Excerpts from Branchaud Deposition Transcript in related IPR2013-00128", dated Oct. 3, 2013.
IPR2013-00266, "Decision Institution of Inter Partes Review", dated Oct. 28, 2013.
IPR2013-00266, "Scheduling Order", dated Oct. 28, 2013.
IPR2013-00266, "Intelligent Bio-Systems Inc.'s List of Proposed Motions", dated Nov. 14, 2013.
IPR2013-00266, "Patent Owner Illumina's Proposed Motions", dated Nov. 14, 2013.
IPR2013-00266, "Declaration of William R. Zimmerman in Support of Motion to Appear Pro Hac Vice on Behalf of Patent Owner Illumina Cambridge Ltd.", dated Nov. 21, 2013.
IPR2013-00266, "Illumina Updated Exhibit List", dated Nov. 21, 2013.
IPR2013-00266, "Motion for William R. Zimmerman to Appear Pro Hac Vice on Behalf of Patent Owner Illumina Cambridge Ltd", dated Nov. 21, 2013.
IPR2013-00266, "Patent Owner Illumina's Additional Power of Attorney", dated Nov. 21, 2013.
IPR2013-00266, "Order Conduct of the Proceeding", dated Nov. 26, 2013.

IPR2013-00266, "Decision Illumina's Motion for Pro Hac Vice Admission of William R. Zimmerman", Dated Dec. 7, 2013.
IPR2013-00266, "Redacted Declaration of Eric Vermaas Accompanying Patent Owner's Motion to Amend", dated Dec. 20, 2013.
IPR2013-00266, "Declaration of Jason P. Grier in Support of Petitioner's Motion for Admission Pro Hac Vice of Jason P. Grier", dated Dec. 23, 2013.
IPR2013-00266, "Intelligent Bio-System, Inc.'s Current Exhibit List", dated Dec. 23, 2013.
IPR2013-00266, "Petitioner's Motion for Admission Pro Hac Vice of Jason P. Grier", dated Dec. 23, 2013.
IPR2013-00266, "Curriculum Vitae Floyd Eric Romesberg", dated Dec. 30, 2013.
IPR2013-00266, "Declaration of Floyd Romesberg, Ph.D., in Support of Patent Owner's Motion to Amend", dated Dec. 30, 2013.
IPR2013-00266, "Illumina Motion to Seal", dated Dec. 30, 2013.
IPR2013-00266, "Illumina Updated Exhibit List", dated Dec. 30, 2013.
IPR2013-00266, "Illumina's Motion to Amend", dated Dec. 30, 2013.
IPR2013-00266, "List of Documents Considered by Floyd Romesberg, Ph.D., in Preparing Declaration", Dec. 30, 2013.
IPR2013-00266, "Decision IBS's Motion for Pro Hac Vice Admission of Jason P. Grier", dated Jan. 10, 2014.
IPR2013-00266, "Video Deposition of Eric Vermaas in IPR2013-00128", dated Jan. 13, 2014.
IPR2013-00266, "Video Deposition of Floyd Romesberg, Ph.D. in IPR2013-00128", dated Jan. 14, 2014.
IPR2013-00266, "Second Declaration of Bruce Branchaud in related IPR2013-00128", dated Jan. 24, 2014.
IPR2013-00266, "Intelligent Bio-System, Inc.'s Current Exhibit List Under 37 C.F.R. § 42.63", dated Feb. 28, 2014.
IPR2013-00266, "Petitioner Intelligent Bio-Systems, Inc.'s Motion to Seal Under 37 C.F.R. § 42.54", dated Feb. 28, 2014.
IPR2013-00266, "Petitioner Intelligent Bio-Systems, Inc.'s Opposition to Illumina's Motion to Amend", dated Feb. 28, 2014.
IPR2013-00266, "Second Declaration of Dr. Bruce Branchaud in Support of Intelligent Bio-Systems, Inc.'s Opposition to Illumina's Motion to Amend", dated Feb. 28, 2014.
IPR2013-00266, "Illumina Objections to the Admissibility of IBS Evidence Served on Feb. 28, 2014", dated Mar. 7, 2014.
IPR2013-00266, "Branchaud Deposition Transcript", dated Mar. 11, 2014.
IPR2013-00266 "Second Declaration of Floyd Romesberg, Ph.D.", *Intelligent Bio-Systems, Inc. v. Illumina Cambridge Ltd.*, Case IPR2013-00266 (LMG), U.S. Pat. No. 8,158,346, Mar. 21, 2014, 20 pages.
IPR2013-00266, "Illumina Updated Exhibit List", dated Mar. 21, 2014.
IPR2013-00266, "Patent Owner Illumina's Reply to Petitioner's Opposition to Illumina's Motion to Amend", dated Mar. 21, 2014.
IPR2013-00266, "Second Declaration of Floyd Romesberg, Ph.D.", dated Mar. 21, 2014.
IPR2013-00266, "Second Declaration of Jason P. Grier", dated Mar. 21, 2014.
IPR2013-00266, "Intelligent Bio-System's Objections to Illumina's Exhibits Submitted With Its Reply to Petitioner's Opposition to Illumina's Motion to Amend", Mar. 28, 2014.
IPR2013-00266, "Intelligent Bio-Systems' Notice of Cross-Examination Deposition of Illumina's Declarant Dr. Floyd Romesberg", dated Apr. 3, 2014.
IPR2013-00266, "Inter Partes Review—Petitioner Power of Attorney", dated Apr. 4, 2014.
IPR2013-00266, "Order Revised Scheduling Order 37 C.F.R. § 42.5", dated Apr. 4, 2014.
IPR2013-00266, "Petitioner Intelligent Bio-Systems, Inc.'s Supplemental Mandatory Notice: Additional Backup Counsel", dated Apr. 4, 2014.
IPR2013-00266, "Romesberg Errata and Signature Page", dated Apr. 10, 2014.
IPR2013-00266, "Video Deposition of Floyd Romesberg, Ph.D.", dated Apr. 10, 2014.

(56) References Cited

OTHER PUBLICATIONS

IPR2013-00266, "Illumina Motion to Exclude IBS Evidence", dated Apr. 18, 2014.
IPR2013-00266, "Illumina Request for Oral Argument", dated Apr. 18, 2014.
IPR2013-00266, "Illumina Updated Exhibit List", dated Apr. 18, 2014.
IPR2013-00266, "Intelligent Bio-System, Inc.'s Current Exhibit List Under 37 C.F.R. § 42.63", dated Apr. 18, 2014.
IPR2013-00266, "Petitioner Intelligent Bio-Systems, Inc.'s Motion for Observations on the Cross-Examination Testimony of Floyd Romesberg, Ph.D.", dated Apr. 18, 2014.
IPR2013-00266, "Petitioner Intelligent Bio-Systems, Inc.'s Motion to Exclude Evidence", dated Apr. 18, 2014.
IPR2013-00266, "Petitioner Intelligent Bio-Systems, Inc.'s Request for Oral Argument", dated Apr. 18, 2014.
IPR2013-00266, "Order Trial Hearing", Apr. 29, 2014.
IPR2013-00266, "Illumina Appendix of Authority", dated May 2, 2014.
IPR2013-00266, "Illumina Opposition to IBS Motion to Exclude Illumina Evidence", dated May 2, 2014.
IPR2013-00266, "Illumina Response to IBS Mot. for Observations on Romesberg Testimony", dated May 2, 2014.
IPR2013-00266, "Intelligent Bio-System, Inc.'s Current Exhibit List Under 37 C.F.R. § 42.63", dated May 2, 2014.
IPR2013-00266, "Intelligent Bio-Systems, Inc.'s Opposition to Illumina's Motion to Exclude IBS Evidence", dated May 2, 2014.
IPR2013-00266, "Illumina Reply to IBS Opposition to Motion to Exclude", dated May 9, 2014.
IPR2013-00266, "Errata Sheet for Bruce Branchaud, Ph.D. Deposition Taken: Mar. 11, 2014", dated May 16, 2014.
IPR2013-00266, "Intelligent Bio-System, Inc.'s Current Exhibit List Under 37 C.F.R. § 42.63", dated May 16, 2014.
IPR2013-00266, "Illumina's Third Supplemental Mandatory Notice Re Backup Counsel—37 C.F.R. § 42.8 (a)(3)", dated May 21, 2014.
IPR2013-00266, "Illumina's Additional Power of Attorney", dated May 22, 2014.
IPR2013-00266, "Illumina's Notice of Filing Its Demonstratives (Exhibit 2060) for May 28, 2014 Oral Argument", dated May 22, 2014.
IPR2013-00266, "Illumina's Updated Exhibit List", dated May 22, 2014.
IPR2013-00266, "Intelligent Bio-System, Inc.'s Current Exhibit List Under 37 C.F.R. § 42.63", dated May 22, 2014.
IPR2013-00266, "Intelligent Bio-System, Inc.'s Notice of Filing Its Demonstratives (Ex. 1045) for May 28, 2014 Oral Argument", dated May 22, 2014.
IPR2013-00266, "Demonstrative Exhibits of Intelligent Bio-Systems, Inc. for Oral Hearing", dated May 28, 2014.
IPR2013-00266, "Illumina's Demonstratives for Oral Argument", dated May 28, 2014.
IPR2013-00266 # 1, "Petitioner Intelligent Bio-Systems, Inc.'s Updated Mandatory Notice of Counsel", Jun. 6, 2014.
IPR2013-00266 # 2, "Decision, Motion to Seal", Jun. 16, 2014.
IPR2013-00266 # 3, "Proceedings", Jul. 8, 2014.
IPR2013-00266 # 4, "Renewed Motion for Attorneys to Withdraw as Backup Counsel for Illumina", Jul. 29, 2014.
IPR2013-00266 # 5, "Decision, Motion to Withdraw", Oct. 7, 2014.
IPR2013-00266 # 6, "Illumina Revocation of Power of Attorney for James G. Morrow and James D. Borchardt", Oct. 27, 2014.
IPR2013-00266 # 7, "Final Written Decision", Oct. 28, 2014.
IPR2013-00266 # 8, "Erratum", Oct. 28, 2014.
IPR2013-0266 "Illumina Notice of Appeal in the U.S. Court of Appeals for the Federal Circuit", Nov. 26, 2014.
IPR2013-00324, "Declaration of Dr. Bruce P. Branchaud in Support of Petition for Inter Partes Review of U.S. Pat. No. 7,057,026", dated Jun. 4, 2013.
IPR2013-00324, "Excerpts from the '026 file history", dated Jun. 4, 2013.
IPR2013-00324, "Exhibit List", dated Jun. 4, 2013.
IPR2013-00324, "Inter Partes Review—Petitioner Power of Attorney", dated Jun. 4, 2013.
IPR2013-00324, "Notice of Filing Date Accorded to Petition and Time for Filing Patent Owner Preliminary Response", dated Jun. 4, 2013.
IPR2013-00324, "Petition for Inter Partes Review of U.S. Pat. No. 7,057,026", dated Jun. 4, 2013.
IPR2013-00324, "Notice of Filing Date Accorded to Petition and Time for Filing Patent Owner Preliminary Response", dated Jun. 6, 2013.
IPR2013-00324, "Illumina Cambridge Limited Mandatory Notices", dated Jun. 24, 2013.
IPR2013-00324, "Illumina Cambridge Limited's Power of Attorney in an Inter Partes Review", dated Jun. 24, 2013.
IPR2013-00324, "Declaration of Robert R. Baron, Jr. in Support of Petitioner's Motion for Admission Pro Hac Vice of Robert R. Baron, Jr.", dated Jul. 19, 2013.
IPR2013-00324, "Intelligent Bio-System, Inc.'s Current Exhibit List", dated Jul. 19, 2013.
IPR2013-00324, "Petitioner's Motion for Admission Pro Hac Vice of Robert R. Baron, Jr.", dated Jul. 19, 2013.
IPR2013-00324, "Decision Intelligent Bio-Systems' Motion for Pro Hac Vice Admission of Robert R. Baron, Jr.", dated Aug. 9, 2013.
IPR2013-00324, "Order Conduct of the Proceeding", dated Aug. 29, 2013.
IPR2013-00324, "Illumina Motion for Counsel to Withdraw From the Proceeding to Permit Substitution of Counsel", dated Aug. 30, 2013.
IPR2013-00324, "Illumina Notice of Waiver of Patent Owner Preliminary Response", dated Sep. 9, 2013.
IPR2013-00324, "Decision Motion to Withdraw", dated Sep. 10, 2013.
IPR2013-00324, "Illumina's First Supplemental Mandatory Notices", dated Sep. 11, 2013.
IPR2013-00324, "Illumina Cambridge Limited's Updated Power of Attorney in an Inter Partes Review", dated Sep. 16, 2013.
IPR2013-00324, "Illumina's Second Supplemental Mandatory Notices", dated Sep. 17, 2013.
IPR2013-00324, "Decision Denying Institution of Inter Partes Review", dated Nov. 21, 2013.
IPR2013-00324 # 1, "Intelligent Bio-Systems, Inc. Request for Refund of Post-Institution Fee", Mar. 3, 2014.
IPR2013-00324 # 2, "Notice of Refund", Mar. 4, 2014.
IPR2013-00517, "U.S. Appl. No. 09/684,670", dated Oct. 6, 2000.
IPR2013-00517, "Press Release—Illumina to acquire Solexa", dated 2006.
IPR2013-00517, "Research Plan", dated Feb. 2, 2006.
IPR2013-00517, "Ju Proposal", dated Nov. 29, 2006.
IPR2013-00517, "Email from msm2137 to Jingyue Ju", dated Mar. 8, 2007.
IPR2013-00517, "Ju Lab Thesis Proposal", dated Mar. 19, 2007.
IPR2013-00517, "Email chain from Jerzy Olenik to msm2137", dated Jun. 3, 2007.
IPR2013-00517, "Email chain from Steven Gordon to Jeffrey Arnold", dated Jun. 3, 2007.
IPR2013-00517, "Dae H. Kim Thesis Proposal Presentation", dated Jun. 28, 2007.
IPR2013-00517, "Email Chain from Jerzy Olejnik to z179", dated Jun. 29, 2007.
IPR2013-00517, "Email from Jerzy Olejnik to Stephen Buchwald and Steven Gordon", dated Aug. 10, 2007.
IPR2013-00517, "Invention Disclosure Form", dated Aug. 17, 2007.
IPR2013-00517, "Email chain from Jerzy Olejnik to Andrew Gardner", dated Oct. 2, 2007.
IPR2013-00517, "Email chain from Steven Gordon to Jingyue Ju", dated Oct. 29, 2007.
IPR2013-00517, "Email chain from Jim Russo to hc2278, Jia guo, Dae Kim, 1x2109, Zengmin Li, qm6, 1y2141, Jingyue Ju, Christine Rupp, Petra Lee Forde, Irina Morozova and John Edwards", dated Nov. 4, 2007.
IPR2013-00517, "Ju Proposal", dated Nov. 6, 2007.
IPR2013-00517, "Email chain from Jerzy Olenik to hc228 and Shiv Kumar", dated Feb. 1, 2008.

(56) References Cited

OTHER PUBLICATIONS

IPR2013-00517, "Email from Bert Vogelstein to mysworld1982, dj222 and jrel3", dated Mar. 3, 2008.
IPR2013-00517, "Email from Bert Vogelstein to jre, Devin, jw2231, Jingyue Ju, Nickolas Papadopoulos and K8", dated Mar. 11, 2008.
IPR2013-00517, "Lin Yu 3rd Year Research Presentation", dated May 2, 2008.
IPR2013-00517, "Intelligent Bio-Systems, Inc., Custom Synthesis of Nucleotide Analogs", dated May 6, 2008.
IPR2013-00517, "Email from Jingyue Ju to Jingue Ju and Christine Rupp", dated Jun. 5, 2008.
IPR2013-00517, "Draft to Cao article", dated Sep. 18, 2008.
IPR2013-00517, "Yu, Sequencing by Synthesis with Cleavable Fluorescent Nucleotide Reversible Terminators (C-F-NRTs)", dated Oct. 20, 2008.
IPR2013-00517, "Email from Jerzay Olejnik to Evan Guggenheim, Visa Visalakshi, Selase Metewo Enuameh, Mong Sano Marma, Huanyan Cao, Lei O'Malley and Alisha Perelta", dated Nov. 11, 2008.
IPR2013-00517, "Email from Huanyan Cao to Huanyan Cao, Jerzy Olejnik, Mong Sano Marma, Waldemar Szczepanik and Wojciech Czardybon", dated Mar. 4, 2009.
IPR2013-00517, "Notice of Allowance in U.S. Appl. No. 11/301,578", dated Apr. 30, 2009.
IPR2013-00517, "Intelligent Bio-Systems, Inc., Cleavage", dated Aug. 2009.
IPR2013-00517, "Intelligent Bio-Systems, Inc., Nucleotides", dated Jun. 15, 2011.
IPR2013-00517, "Email from Shiv Kumar to Jerzy Olejnik and Jinguyue Ju", dated Jul. 5, 2012.
IPR2013-00517, "Intelligent Bio-Systems, Inc., Custom Synthesis of Nucleotide Analogs", dated Aug. 1, 2012.
IPR2013-00517, "Petition for Inter Partes Review of U.S. Pat. No. 7,713,698", dated Sep. 16, 2012.
IPR2013-00517, "Petition for Inter Partes Review of U.S. Pat. No. 7,790,869", dated Sep. 16, 2012.
IPR2013-00517, "Petition for Inter Partes Review of U.S. Pat. No. 8,088,575", dated Oct. 3, 2012.
IPR2013-00517, "[Proposed] Protective Order", dated Dec. 21, 2012.
IPR2013-00517, "Automated forward and reverse ratcheting of DNA in a nanopore at 5-A precision", dated Jan. 7, 2013.
IPR2013-00517, "Translation Affadavit for Loubinoux", Mar. 18, 2013.
C.A. No. 12-376 (GMS), Videotaped Deposition of Dr Xiaohai Liu, dated Mar. 20, 2013.
IPR2013-00517, "Excerpts from the Deposition Transcript of Dr. Xiaohai Liu", dated Mar. 20, 2013.
IPR2013-00517, "Qiagen's Dietrich Hauffe on Bringing Next-Generation Sequencing to clinical Research and Molecular Dx", Interview; http://www.genomeweb.com/print/1254496, dated Jul. 7, 2013.
IPR2013-00517, "Response to Office Action in U.S. Appl. No. 13/305,415", dated Aug. 14, 2013.
IPR2013-00517, "Declaration of Dr. Bruce P. Branchaud in Support of Petition for Inter Partes Review of U.S. Pat. No. 7,566,537", dated Aug. 16, 2013.
IPR2013-00517, "Exhibit List", dated Aug. 19, 2013.
IPR2013-00517, "Inter Partes Review—Petitioner Power of Attorney", dated Aug. 19, 2013.
IPR2013-00517, "Petition for Inter Partes Review of U.S. Pat. No. 7,566,537", dated Aug. 19, 2013.
IPR2013-00517, "Notice of Filing Date Accorded to Petition and Time for Filing Patent Owner Preliminary Response", dated Aug. 26, 2013.
IPR2013-00517, "Intelligent Bio-Systems, Inc.'s Response to Notice of Filing Date Accorded to Petition and Time for Filing Patent Owner Preliminary Response", dated Aug. 30, 2013.
IPR2013-00517, "Revised Petition for Inter Partes Review of U.S. Pat. No. 7,566,537", dated Aug. 30, 2013.
IPR2013-00517, "Patent Owner Illumina's Power of Attorney", dated Sep. 9, 2013.
IPR2013-00517, "Patent Owner Submission of Mandatory Notice Information", dated Sep. 9, 2013.
IPR2013-00517, "Transcript of Videotaped Deposition of .cndot. Bruce Branchaud, Ph.D. in IPR-2013-00128", dated Oct. 3, 2013.
IPR2013-00517, "Illumina Notice of Waiver of Patent Owner Preliminary Response", dated Nov. 26, 2013.
IPR2013-00517, "Decision IBS's Motion for Pro Hac Vice Admission of Jason P. Grier", dated Dec. 23, 2013.
IPR2013-00517, "Declaration of Jason P. Grier in Support of Petitioner's Motion for Admission Pro Hac Vice of Jason P. Grier", dated Dec. 23, 2013.
IPR2013-00517, "Declaration of Robert R. Baron, Jr. in Support of Petitioner's Motion for Admission Pro Hac Vice of Robert R. Baron, Jr.", dated Dec. 23, 2013.
IPR2013-00517, "Intelligent Bio-System, Inc.'s Current Exhibit List", dated Dec. 23, 2013.
IPR2013-00517, "Petitioner's Motion for Admission Pro Hac Vice of Jason P. Grier", dated Dec. 23, 2013.
IPR2013-00517, "Petitioner's Motion for Admission Pro Hac Vice of Robert R. Baron, Jr.", dated Dec. 23, 2013.
IPR2013-00517, "Decision IBS's Motion for Pro Hac Vice Admission of Jason P. Grier", dated Jan. 10, 2014.
IPR2013-00517, "Decision IBS's Motion for Pro Hac Vice Admission of Robert R. Baron, Jr.", dated Jan. 10, 2014.
IPR2013-00517, "Transcript of Videotaped Deposition of Bruce P. Branchaud in IPR-2013-000128", dated Feb. 11, 2014.
IPR2013-00517, "Decision—Institution of Inter Partes Review—37 CFR 42.108", dated Feb. 13, 2014.
IPR2013-00517, "Declaration of William R. Zimmerman in Support of Motion to Appear Pro Hac Vice on Behalf of Patent Owner Illumina Cambridge Ltd.", dated Feb. 13, 2014.
IPR2013-00517, "Scheduling Order", dated Feb. 13, 2014.
IPR2013-00517, "Intelligent Bio-Systems Inc.'s List of Proposed Motions", dated Feb. 27, 2014.
IPR2013-00517, "Patent Owner Illumina's Proposed Motions", dated Feb. 27, 2014.
IPR2013-00517, "Order—Conduct of the Proceedings", dated Mar. 6, 2014.
IPR2013-00517, "Transcript of Videotaped Deposition of Bruce P. Branchaud in IPR2013-00266", dated Mar. 11, 2014.
IPR2013-00517, "Illumina Exhibit List", dated Mar. 13, 2014.
IPR2013-00517, "Motion for William R. Zimmerman to Appearpro Hac Vice on Behalf of Patent Owner Illumina Cambridge Ltd.", dated Mar. 13, 2014.
IPR2013-00517, "Illumina Notice of Cross-Examination Deposition of IBS Declarant Dr. Bruce P. Branchaud", dated Mar. 25, 2014.
IPR2013-00517, "Order—Patent Owner's Motion for William R Zimmerman to Appear Pro Hac Vice", dated Apr. 2, 2014.
IPR2013-00517, "Inter Partes Review—Petitioner Power of Attorney", dated Apr. 4, 2014.
IPR2013-00517, "Petitioner Intelligent Bio-Systems, Inc.'s Supplemental Mandatory Notice: Additional Backup Counsel", dated Apr. 4, 2014.
IPR2013-00517, "Notice of Stip to Change Due Dates 1 and 2", dated Apr. 7, 2014.
IPR2013-00517, "Videotaped Deposition of: Bruce P. Branchaud, Ph.D.", dated Apr. 8, 2014.
IPR2013-00517, "Curriculum Vitae Dr. Kevin Burgess", dated May 5, 2014.
IPR2013-00517, "Declaration of Floyd Romesberg, Ph.D.", dated May 5, 2014.
IPR2013-00517, "Declaration of Kevin Burgess, Ph.D.", dated May 5, 2014.
IPR2013-00517, "Declaration of Rosalyn M. Espejo Regarding Fed. R. Evid. 902(11) Certification of Records", dated May 5, 2014.
IPR2013-00517, "Illumina Additional Power of Attorney", dated May 5, 2014.
IPR2013-00517, "Illumina Motion to Seal Under 37 C.F.R. § 42.54", dated May 5, 2014.
IPR2013-00517, "Illumina Updated Exhibit List", dated May 5, 2014.

(56) References Cited

OTHER PUBLICATIONS

IPR2013-00517, "Illumina Updated Mandatory Notice Regarding Designated Counsel", dated May 5, 2014.
IPR2013-00517, "Note regarding Ju's Chemistry", dated May 5, 2014.
IPR2013-00517, "Order Conduct of the Proceedings 37 .F.R. § 42.5", dated May 6, 2014.
IPR2013-00517, "Order Conduct of the Proceedings 37 .F.R. § 42.5", dated May 7, 2014.
IPR2013-00517, "Petitioner Intelligent Bio-Systems, Inc.'s Supplemental Mandatory Notice: Additional Backup Counsel", filed Jun. 3, 2014.
IPR2013-00517 "Video Deposition of Floyd Romesberg, Ph.D.", *Intelligent Bio-Systems, Inc.* vs. *Illumina Cambridge, Ltd.*, No. IPR2013-00517, U.S. Pat. No. 7,566,537, Jul. 8, 2014, 190 pages.
IPR2013-00517 "Declaration of Dr. Michael Metzker in Support of Intelligent Bio-Systems, Inc.'s Reply to Illumina's Patent Owner Response", *Intelligent Bio-Systems, Inc.* v. *Illumina Cambridge Limited*, Case IPR2013-00517 (LMG), U.S. Pat. No. 7,566,537, Exhibit No. 1046, Jul. 28, 2014, 33 pages.
IPR2013-00517 "Second Declaration of Dr. Bruce Branchaud in Support of Intelligent Bio-Systems, Inc.'s Reply to Illumina's Patent Owner Response", *Intelligent Bio-Systems, Inc.* v. *Illumina Cambridge Limited*, U.S. Pat. No. 7,566,537, Exhibit No. 1031, Jul. 28, 2014, 22 pages.
IPR2013-00517, "Decision Motion to Seal", Jan. 29, 2015.
IPR2013-00517, "Record of Oral Hearing held Friday, Oct. 10, 2014", dated Feb. 2, 2015.
IPR2013-00517, "Joint Revised Motion to Seal", Feb. 5, 2015.
IPR2013-00517, "Decision Motion to Seal", Feb. 10, 2015.
IPR2013-00517, "Final Written Decision", dated Feb. 11, 2015.
IPR2013-00517, "Petitioner Intelligent Bio-Systems, Inc.'s Notice of Appeal", Apr. 8, 2015.
IPR2013-00517, "Order Conduct of the Proceeding", Apr. 16, 2015.
IPR2013-00517 # 1, "Petitioner Intelligent Bio-Systems, Inc.'s Supplemental Mandatory Notice: Additional Backup Counsel", Jun. 3, 2014.
IPR2013-00517 # 2, "Power of Attorney", Jun. 3, 2014.
IPR2013-00517 # 3, "Petitioner Intelligent Bio-Systems, Inc.'s Corrected Supplemental Mandatory Notice: Additional Backup Counsel", Jun. 3, 2014.
IPR2013-00517 # 4, "Petitioner Intelligent Bio-Systems, Inc.'s Response to Illumina's Motion to Seal", Jun. 5, 2014.
IPR2013-00517 # 5, "Petitioner Intelligent Bio-Systems, Inc.'s Updated Mandatory Notice of Counsel", Jun. 3, 2014.
IPR2013-00517 # 6, "Notice of Stipulation to Change Due Date 2", Jun. 23, 2014.
IPR2013-00517 # 7, "Intelligent Bio-System's Notice of Cross-Examination Deposition of Illumina's Declarant Dr. Floyd Romesberg", Jun. 26, 2014.
IPR2013-00517 # 8, "Intelligent Bio-Systems' Notice of Cross-Examination Deposition of Illumina's Declarant Dr. Kevin Burgess", Jun. 27, 2014.
IPR2013-00517 # 9, "Declaration of Derek C. Walter in Support of Motion to Appear Pro Hac Vice on Behalf of Patent Owner Illumina Cambridge Ltd.", Jun. 23, 2014.
IPR2013-00517 # 10, "Illumina Updated Exhibit List", Jul. 7, 2014.
IPR2013-00517 # 11, "Motion for Derek C. Walter to Appear Pro Hac Vice on Behalf of Patent Owner Illumina Cambridge Ltd.", Jul. 7, 2014.
IPR2013-00517 # 12, "Illumina Reply to IBS Opposition to Illumina Motion to File Under Seal", Jul. 7, 2014.
IPR2013-00517 # 13, "Illumina Updated Mandatory Notice Adding Sheila N. Swaroop as Additional Backup Counsel", Jul. 7, 2014.
IPR2013-00517 # 14, "Illumina Additional Power of Attorney", Jul. 11, 2014.
IPR2013-00517 # 15, "Decision Illumina's Motion for Pro Hac Vice Admission of Derek C. Walter", Jul. 15, 2014.
IPR2013-00517 # 16, "Illumina Updated Mandatory Notice Adding Derek C. Walter as Additional Backup Counsel", Jul. 18, 2014.
IPR2013-00517 # 17, "Liu Transcript p. 295, Exhibit 1022", Jul. 28, 2014.
IPR2013-00517 # 18, "Biophysical Society, Abstracts, Sixth Annual Meeting", Feb. 14-16, 1962.
IPR2013-00517 # 19, Ireland, et al., "Approach to the Total Synthesis of Chlorothricolide: Synthesis of (+)-19,20-Dihydro-24-O-metylchlorothricolide. Methyl Ester, Ethyl Carbonate", J. Org. Chem. 51, 1986, Jul. 28, 2014, 685-648.
IPR2013-00517 # 20, Kamal et al., "A Mild and Rapid Regeneration of Alcohols from their Allylic Ethers by Chlorotrimethylsilane/Sodium Iodide", Tetrahedrom Letters 40, 1999, Jul. 28, 2014, 31-372.
IPR2013-00517 # 21, "Videotaped Deposition of Kevin Burgess, Ph.D., taken before Greg S. Weiland, CSr, RMR, CRR, pursuant to the Applicable Rules Pertaining to the Taking of Depositions", Jul. 28, 2014.
IPR2013-00517 # 22, "Video Deposition of Floyd Romesberg, Ph.D.", Jul. 8, 2014.
IPR2013-00517 # 23, "Prosecution History Excerpt, Restriction Requirement", Jul. 12, 2007.
IPR2013-00517 # 24, "The American Heritage College Dictionary, Third Edition", Jul. 28, 2014.
IPR2013-00517 # 25, Faucher et al., "Tris(2-Carboxyethyl)phosphine (TCEP) for the Reduction of Sulfoxides, Sulfonylchlorides, N-Oxides, and Azides", Synthetic Communications vol. 33, No. 22, 2003, 3503-3511.
IPR2013-00517 # 26, Variagenics, Inc., "WO 02/21098", Mar. 14, 2002.
IPR2013-00517 # 27, Saxon et al., "Cell Surface Engineering by a Modified Staudinger Reaction", Science vol. 287, Mar. 17, 2000.
IPR2013-00517 # 28, Furniss et al., "Vogel's Textbook of Practical Organic Chemistry, Fifth Edition", 1989.
IPR2013-00517 # 29, Gololobov et al., "Recent Advances in the Staudinger Reaction", Tetrahedron, vol. 48, No. 8, 1992, 1353-1406.
IPR2013-00517# 30, "Second Declaration of Dr. Bruce Branchaud in Support of Intelligent Bio-Systems, Inc.'s Reply to Illumina's Patent Owner Response", Jul. 28, 2014.
IPR2013-00517 # 31, Hyman, "U.S. Pat. No. 5,602,000", Feb. 11, 1997.
IPR2013-00517 # 32, Chen, "DNA polymerases drive DNA sequencing-by-synthesis technologies: both past and present", Frontiers in Microbiology, Review Article,, Jun. 24, 2014.
IPR2013-00517 # 33, Chang et al., "Molecular Biology of Terminal Transferase", CRC Critical Reviews in Biochemistry, vol. 21, Issue 1, Jul. 28, 2014, 27-52.
IPR2013-00517 # 34, Mag et al., "Synthesis and selective cleavage of oligodeoxyribonucleotides containing non-chiral internucleotide phosphoramidate linkages", Nucleic Acids Research, vol. 17, No. 15, 1989.
IPR2013-00517 # 35, Laidler et al., "Chemical Kinetics, Third Edition", 1987, 10-11.
IPR2013-00517 # 36, "Park IP Translations", Jun. 30, 2014.
IPR2013-00517 # 37, Knouzi et al., "English Translation", Aug. 2, 1985.
IPR2013-00517 # 38, Knouzi et al., "Reduction d'azides par la triphenylphosphine en presence d'eau: une methode generale et chimioselective d'acces auz amines primaires", Feb. 8, 1985, 815-819.
IPR2013-00517 # 39, Smith et al., "US Patent Application Publication No. 2006/0240439", Oct. 26, 2006.
IPR2013-00517 # 40, Bentley, "Supplemental Information", Nature, doi: 10.1038/nature07517, Jul. 28, 2014.
IPR2013-00517 # 41, Kirby, "A New Method for the Isolation of Deoxyribonucleic Acids: Evidence on the Nature of Bonds between Deoxyribonucleic Acid and Protein", Renal Clearance of 17-oxo Steroid Conjugates, vol. 66, 1957, 495-504.
IPR2013-00517 # 42, Efimov et al., "An Azidomethyl Protective Group in the Synthesis of Oligoribonucleotides by the Phosphotriester Method", Letters to the Editor, Russian Journal of Bioorganic Chemistry, vol. 35, No. 2, 2009, 250-253.

(56) References Cited

OTHER PUBLICATIONS

IPR2013-00517 # 43, Levine et al., "The Relationship of Structure to the Effectiveness of Denaturing Agents for Deoxyribonucleic Acid", Biochemistry, vol. 2, No. 1, Jan.-Feb. 1963, 168-175.
IPR2013-00517 # 44, Leberton et al., "Structure-Immunosuppressive Activity Relationships of New Analogues of 15-Deoxyspergualin. 2. Structural Modifications of the Spermidine Moiety", J. Med. Chem. 42, 1999, 4749-4763.
IPR2013-00517 # 45, "Declaration of Dr. Michael Metzker in Support of Intelligent Bio-Systems, Inc.'s Reply to Illumina's Patent Owner Response", Jul. 28, 2014.
IPR2013-00517 # 46, "Petitioner Intelligent Bio-Systems, Inc.'s Motion to Seal Under 37 C.F.R. 42.54", Jul. 28, 2014.
IPR2013-00517 # 47, "Intelligent Bio-System, Inc.'s Current Exhibit List Under 37 C.F.R., 42.63", Jul. 28, 2014.
IPR2013-00517 # 48, "Petitioner Intelligent Bio-Systems' Reply to Illumina's Patent Owner Response", Jul. 28, 2014.
IPR2013-00517 # 49, "Order Conduct of the Proceeding", Jul. 29, 2014.
IPR2013-00517 # 50, "Illumina Notice of Cross-Examination Deposition of IBS Declarant Dr. Michael L. Metzker", Aug. 1, 2014.
IPR2013-00517 # 51, "Illumina Notice of Cross-Examination Deposition of IBS Declarant Dr. Bruce P. Branchaud", Aug. 12, 2014.
IPR2013-00517 # 52, "Patent Owner's email for request for Authorization to File IBS v Illumina", Aug. 20, 2014.
IPR2013-00517 # 53, "Intelligent Bio-System's Objections to Illumina's Exhibits Marked at Dr. Branchaud's Deposition", Sep. 2, 2014.
IPR2013-00517 # 54, "Intelligent Bio-System's Objections to Illumina's Exhibits Marked at Dr. Metzker's Deposition", Aug. 19, 2014.
IPR2013-00517 # 55, "Intelligent Bio-System's Objections to Illumina's Exhibits Submitted with its Patent Owner Response", May 19, 2014.
IPR2013-00517 # 56, "Intelligent Bio-System, Inc.'s Current Exhibit List Under 37 C.F.R., 42.63", Sep. 2, 2014.
IPR2013-00517 # 57, "Petitioner Intelligent Bio-Systems, Inc.'s Request for Oral Argument", Sep. 2, 2014.
IPR2013-00517 # 58, "Petitioner Intelligent Bio-Systems, Inc.'s Motion to Exclude Evidence", Sep. 2, 2014.
IPR2013-00517 # 59, "Illumina's Motion for Observations on the Cross-Examination Testimony of Bruce Branchaud, Ph.D. and Michael Metzker, Ph.D.", Sep. 2, 2014.
IPR2013-00517 # 60, "Illumina Motion to Seal Under 37 C.F.R. 42.54", Sep. 2, 2014.
IPR2013-00517 # 61, "Illumina's Motion to Exclude evidence Pursuant to 37 C.R.F., 42.64(c)", Sep. 2, 2014.
IPR2013-00517 # 62, "Illumina Request for Oral Argument", Sep. 2, 2014.
IPR2013-00517 # 63, "Illumina Updated Exhibit List", Sep. 2, 2014.
IPR2013-00517 # 64, "Videotaped sworn testimony of Bruce P. Branchaud, Ph.D.", Sep. 2, 2014.
IPR2013-00517 # 65, "Videotaped Deposition of Michael L. Metzker, Ph.D.", Aug. 12, 2014.
IPR2013-00517 # 66, "Illumina Objections to Admissibility of IBS Evidence Served With Reply", Aug. 4, 2014.
IPR2013-00517 # 67, Reardon et al., "Reduction of 3'-Azido-3"-deoxythymidine (AZT) and AZT Nucleotides by Thiols", The Journal of Biological Chemistry, vol. 269, No. 23, Jun. 10, 1994, 15999-16008.
IPR2013-00517 # 68, Sebastian et al., "Dendrimers with N,N-Disubstituted Hydrazines as End Groups, Useful Precursors for the Synthesis of Water-Soluble Dendrimers Capped with Carbohydrate, Carboxylic or Boronic Acid Derivatives", Tetrahedron 56, 2000, 6269-6277.
IPR2013-00517 # 69, Aldrich, "Fine Chemicals", Aldrich Chemical Company, Inc, 1986.
IPR2013-00517 # 70, Wu et al., "Termination of DNA synthesis by N6-alkylated, not 3'O-alkylated, photocleavable 2'-deoxyadenosine triphosphates", Nucleic Acids Research, vol. 35, No. 19, 2007, 6339-6349.
IPR2013-00517 # 71, "Initial sequencing and analysis of the human genome", Nature, vol. 409, 2001, 850-921.
IPR2013-00517 # 72, Gardner et al., "Rapid incorporation kinetics and improved fidelity of a novel class of 3'-OH unblocked reversible terminators", Nucleic Acids Research, vol. 40, No. 15, May 8, 2012, 7404-7415.
IPR2013-00517 # 73, Mussini et al., "Criteria for Standardization of pH Measurements in Organic Solvents and Water + Organic Solvent Mixtures of Moderate to High Permittivities", Pure & Appl. Chem., vol. 57, No. 6, 1985, 865-876.
IPR2013-00517 # 74, O'Neil, et al., "The Merck Index, an Encyclopedia of Chemicals, Drugs, and Biologicals, Thirteenth Edition", 2001.
IPR2013-00517 # 75, Metzker, "US Publication No. 2003/0180769", Sep. 25, 2003.
IPR2013-00517 # 76, Hanlon, "The importance of London dispersion forces in the maintenance of the deoxyribonuleic acid helix", Biochemical and Biophysical Research Communications, vol. 23, No. 6, 1966.
IPR2013-00517 # 77, Treinin, "General and theoretical aspects, Chapter I, The Chemistry of the Azido Group, Edited by Saul Patai", 1971.
IPR2013-00517 # 78, Tsai et al., "Versatile and Efficient Synthesis of a New Class of Aza-Based Phosphinic Amide Ligands via Unusual P—C Cleavage", Helvetica Chimica Acta, vol. 89, 2006, 3007-3017.
IPR2013-00517 # 79, Metzker, "Sequencing technologies—the next generation", Nature Reviews, Genetics, vol. 11, Jan. 2010, 31-46.
IPR2013-00517 # 80, "Intelligent Bio-Systems, Inc.'s Opposition to Illumina's Motion to Exclude Evidence", Sep. 15, 2014.
IPR2013-00517 # 81, "IBS's response to Illumina's motion for observations on the cross-examination testimony of Bruce Branchaud, Ph.D., and Michael Metzker, Ph.D.", Sep. 15, 2014.
IPR2013-00517 # 82, "Answer and Counterclaims of Defendant Intelligent Bio-Systems, Inc.", Sep. 18, 2013.
IPR2013-00517 # 83, "Declaration of Rosalyn M. Espejo Regarding Fed.R. Evid. 902(11) Certification of Records", Jun. 2, 2014.
IPR2013-00517 # 84, "Illumina Updated Exhibit List", Sep. 15, 2014.
IPR2013-00517 # 85, "Illumina's Opposition to IBS Motion to Exclude Evidence", Sep. 15, 2014.
IPR2013-00517 # 86, "Illumina Motion to Seal Under 37 C.F.R. 42.54", Sep. 15, 2014.
IPR2013-00517 # 86, "Order, Trial Hearing", Sep. 17, 2014.
IPR2013-00517 # 88, "Illumina's Reply to IBS's Opposition to Illumina's Motion to Exclude", Sep. 22, 2014.
IPR2013-00517 # 89, "Emails re IBS withdrawing its hearsay objections", Jul. 31, 2014.
IPR2013-00517 # 90, "Errata Sheet for Bruce Branchaud, Ph.D. Deposition", Taken: Aug. 26, 2014.
IPR2013-00517 # 91, "Errata Sheet for Michael L. Metzker, Ph.D. Deposition", Taken: Aug. 12, 2014.
IPR2013-00517 # 92, "Petitioner Intelligent Bio-Systems, Inc.'s Reply to Illumina's Opposition to Intelligent Bio-Systems, Inc.'s Motion to Exclude Evidence", Sep. 22, 2014.
IPR2013-00517 # 93, "Intelligent Bio-System, Inc.'s Current Exhibit List Under 37 C.F.R. 42.63", Sep. 22, 2014.
IPR2013-00517 # 94, Judge Lora M. Green et al., "Illumina's Demonstratives for Oral Hearing", Oct. 10, 2014.
IPR2013-00517 # 95, "Illumina Updated Exhibit List", Oct. 3, 2014.
IPR2013-00517 # 96, "Illumina Notice of Filing and Serving Its Demonstratives (Ex. 2156) for Oral Argument", Oct. 3, 2014.
IPR2013-00517 # 97, "Illumina Additional Power of Attorney for Jeff Costakos", Oct. 3, 2014.
IPR2013-00517 # 98, "Illumina Updated mandatory Notice Adding Jeffrey N. Costakos as Additional Backup Counsel", Oct. 3, 2014.
IPR2013-00517 # 99, Judge Lora M. Green et al., "Demonstrative Exhibits of Intelligent Bio-Systems, Inc. for Oral Hearing", Oct. 10, 2014.
IPR2013-00517 # 100, "Intelligent Bio-System, Inc.'s Notice of Filing Its Demonstratives (Ex. 1062) for Oct. 10, 2014 Oral Argument", Oct. 3, 2014.

(56) References Cited

OTHER PUBLICATIONS

IPR2013-00517 # 101, "Intelligent Bio-System, Inc.'s Current Exhibit List Under 37 C.F.R. 42.63", Oct. 3, 2014.
IPR2013-00517 # 102, Intelligent Bio-Systems, Inc.'s Answer, Affirmative Defenses & Counterclaims to Illumina, Inc. and Illumina Cambridge Ltd.'s Second Amended Counterclaims to Amended Complaint, dated Jan. 7, 2013.
IPR2013-00517 # 124, "Inter Partes Review—Petitioner Power of Attorney", dated Apr. 4, 2014.
IPR2013-00518, "Petition for Inter Partes Review of U.S. Pat. No. 7,790,869", dated Sep. 16, 2012.
IPR2013-00518, "District Court Protective Order", dated Dec. 21, 2012.
IPR2013-00518, "Excerpts from the file history of European Patent Application No. 02781434.2", dated Aug. 9, 2013.
IPR2013-00518, "Excerpts from the '537 Patent File History", dated Aug. 19, 2013.
IPR2013-00518, "Exhibit List", dated Aug. 19, 2013.
IPR2013-00518, "Inter Partes Review—Petitioner Power of Attorney", dated Aug. 19, 2013.
IPR2013-00518, "Petition for Inter Partes Review of U.S. Pat. No. 7,566,537", dated Aug. 19, 2013.
IPR2013-00518, "Notice of Filing Date Accorded to Petition and Time for Filing Patent Owner Preliminary Response", dated Aug. 26, 2013.
IPR2013-00518, "Patent Owner Illumina's Power of Attorney", dated Sep. 9, 2013.
IPR2013-00518, "Patent Owner Submission of Mandatory Notice Information", dated Sep. 9, 2013.
IPR2013-00518, "Petition for Inter Partes Review of U.S. Pat. No. 7,713,698", dated Sep. 16, 2013.
IPR2013-00518, "Petition for Inter Partes Review of U.S. Pat. No. 8,088,575", dated Oct. 3, 2013.
IPR2013-00518, "Illumina Notice of Waiver of Patent Owner Preliminary Response", dated Nov. 26, 2013.
IPR2013-00518, "Declaration of Jason P. Grier in Support of Petitioner's Motion for Admission Pro Hac Vice of Jason P. Grier", dated Dec. 23, 2013.
IPR2013-00518, "Declaration of Robert R. Baron, Jr. In Support of Petitioner'S Motion for Admission Pro Hac Vice of Robert R. Baron, Jr.", dated Dec. 23, 2013.
IPR2013-00518, "Intelligent Bio-System, Inc.'s Current Exhibit List", dated Dec. 23, 2013.
IPR2013-00518, "Petitioner's Motion for Admission Pro Hac Vice of Jason P. Grier", dated Dec. 23, 2013.
IPR2013-00518, "Petitioner's Motion for Admission Pro Hac Vice of Robert R. Baron, Jr.", dated Dec. 23, 2013.
IPR2013-00518, "Decision IBS's Motion for Pro Hac Vice Admission of Jason P. Grier", dated Jan. 10, 2014.
IPR2013-00518, "Decision IBS's Motion for Pro Hac Vice Admission of Robert R. Baron, Jr.", dated Jan. 10, 2014.
IPR2013-00518 "Video Deposition of Floyd Romesberg, Ph.D.", dated Jan. 14, 2014.
IPR2013-00518, "Video Deposition of Eric Vermaas Jan. 13, 2014", dated Jan. 17, 2014.
IPR2013-00518, "Excerpts from File History EP App. No. 02781434. 2", dated Jan. 24, 2014.
IPR2013-00518, "IBS's Opposition to Illumina's Motion to Amend", dated Jan. 24, 2014.
IPR2013-00518, "Petitioner Intelligent Bio-Systems, Inc.'s Motion to Seal Under 37 C.F.R. § 42.54", dated Jan. 24, 2014.
IPR2013-00518, "Substitute Declaration of Floyd Romesberg, Ph.D., In Support of Patent Owner's Motion to Amend", dated Jan. 24, 2014.
IPR2013-00518, "Order—Conduct of the Proceeding 37 C.F.R. § 42.5", dated Jan. 31, 2014.
IPR2013-00518, "Decision—Institution of Inter Partes Review—37 CFR 42.108", dated Feb. 13, 2014.
IPR2013-00518, "Illumina Exhibit List", dated Feb. 13, 2014.
IPR2013-00518, "Scheduling Order", dated Feb. 13, 2014.
IPR2013-00518, "Intelligent Bio-Systems Inc.'s List of Proposed Motions", dated Feb. 27, 2014.
IPR2013-00518, "Patent Owner Illumina's Proposed Motions", dated Feb. 27, 2014.
IPR2013-00518, "Order—Conduct of the Proceedings", dated Mar. 6, 2014.
IPR2013-00518, "Declaration of William R. Zimmerman in Support of Motion to Appear Pro Hac Vice on Behalf of Patent Owner Illumina Cambridge Ltd.", dated Mar. 11, 2014.
IPR2013-00518, "Motion for William R. Zimmerman to Appear Pro Hac Vice on Behalf of Patent Owner Illumina Cambridge Ltd.", dated Mar. 13, 2014.
IPR2013-00518, "Illumina Notice of Cross-Examination Deposition of IBS Declarant Dr. Bruce P. Branchaud", dated Mar. 25, 2014.
IPR2013-00518, "Order—Patent Owner's Motion for William R. Zimmerman to Appear Pro Hac Vice", dated Apr. 2, 2014.
IPR2013-00518, "Inter Partes Review—Petitioner Power of Attorney", dated Apr. 4, 2014.
IPR2013-00518, "Petitioner Intelligent Bio-Systems, Inc.'s Supplemental Mandatory Notice: Additional Backup Counsel", dated Apr. 4, 2014.
IPR2013-00518, "Notice of Stipulation to Change Due Dates 1 and 2", dated Apr. 7, 2014.
IPR2013-00518, "Illumina Request for Adverse Judgment Under 37 CFR § 42.73(b)(2)", dated May 5, 2014.
IPR2013-00518 # 1, "Judgment, Request for Adverse Judgment", May 6, 2014.
Revised Petition for Inter Partes Review of U.S. Pat. No. 7,057,026, dated Feb. 7, 2013.
Final Written Decision of the PTAB regarding Inter Partes Review of U.S. Pat. No. 7,057,026 dated Jul. 25, 2014.
Petition for Inter Partes Review of U.S. Pat. No. 7,566,537 dated Aug. 30, 2013.
Final Written Decision of the PTAB regarding Inter Partes Review of U.S. Pat. No. 7,566,537 dated Feb. 11, 2015.
Final Written Decision of the Ptab regarding Inter Partes Review of U.S. Pat. No. 8,158,346 dated Oct. 28, 2014.
Petition for Inter Partes Review of U.S. Pat. No. 8,158,346 dated May 4, 2013.
Petition for Inter Partes Review of U.S. Pat. No. 7,566,537 B2, IPR2017-02172, filed Oct. 5, 2017.
Ex. No. 1001, IPR2017-02172, Shankar Balasubramanian et al., U.S. Pat. No. 7,566,537 B2 (Jul. 28, 2009) ("'537").
Ex. No. 1002 IPR2017-02172, Excerpts of File History of U.S. Appl. No. 11/301,478.
Ex. No. 1003, IPR2017-02172, Roger Y. Tsien et al., WO 91/06678 A1 (published May 16, 1991) ("Tsien").
Ex. No. 1004, IPR2017-02172, William J. Dower et al., U.S. Pat. No. 5,547,839 (Aug. 20, 1996) ("Dower").
Ex. No. 1005, IPR2017-02172, Protective Groups in Organic Synthesis (Theodora W. Greene & Peter G.M. Wuts eds., 3rd ed. 1999 excerpts ("Greene & Wuts").
Ex. No. 1006, IPR2017-02172, Bernard Loubinoux et al., Protection of Phenols by the Azidomethylene Group Application to the Synthesis of Unstable Phenols, Tetrahedron 44:6055-64 (1988), including translation, supporting affidavit and original publication ("Loubinoux").
Ex. No. 1007, IPR2017-02172, James M. Prober et al., A System for Rapid DNA Sequencing with Fluorescent Chain-Terminating Dideoxynucleotides, Science 238:336-41 1987 ("Prober").
Ex. No. 1008, IPR2017-02172, Sergey Zavgorodny et al., I-Alkylthioalkylation of Nucleoside Hydroxyl Functions and Its Synthetic Applications, Tetrahedron Letters 32:7593-96 1991 ("Zavorodn").
Ex. No. 1009, IPR2017-02172, S.G. Zavgorodny et al., S,X-Acetals in Nucleoside Chemistry, III, Synthesis of 2c and 3'-O-Azidomethyl Derivatives of Ribonucleosides, Nucleosides, Nucleotides & Nucleic Acids 19:1977-91 (2000) ("Zavgorodny 2000").
Ex. No. 1010, IPR2017-02172, J.D. Watson & F.H.C. Crick, Molecular Structure of Nucleic Acids, Nature 171:737-38 1953.
Ex. No. 1011, IPR2017-02172, Steven M. Carr, Deoxyribose versus Ribose Sugars (2014), at https://www.mun.ca/biology/scarrlRibose_sugar.html (downloaded Sep. 25, 2017).

(56) References Cited

OTHER PUBLICATIONS

Ex. No. 1012, IPR2017-02172, Michael L. Metzker, Emerging Technologies in DNA Sequencing, Genome Res. 15: 1767-76 2005 ("Metzker 2005").
Ex. No. 1013, IPR2017-02172, A. Kornberg et al., Enzymatic Synthesis of deoxyribonucleic acid, Biochim. Biophys. Acta 21:197-198 1956 ("Kornberg").
Ex. No. 1014, IPR2017-02172, Bruce Merrifield, Solid Phase Synthesis, Science 232:341-47 (1986) ("Merrifield").
Ex. No. 1015, IPR2017-02172, William C. Copeland et al., Human DNA Polymerases α and β Are Able to Incorporate Anti-HIV Deoxynucleotides Into DNA, J. Biol. Chem. 267:21459-64 (1992) ("Copeland 1992").
Ex. 1016, IPR2017-02172, Hamilton O. Smith & K.W. Wilcox, A Restriction Enzyme from Hemophilus influenzae. 1. Purification and General Properties, J. Mol. Biol. 51:379-91 (1970).
Ex. 1017, IPR2017-02172, Thomas J. Kelly, Jr. & Hamilton O. Smith, A restriction enzyme from Hemophilus influenzae. II. Base sequence of the recognition site, J. Mol. Biol. 51:393-409 (1970).
Ex. 1018, IPR2017-02172, F. Sanger & A.R. Coulson, A Rapid Method for Determining Sequences in DNA by Primed Synthesis with DNA Polymerase, J. Mol. Biol. 94: 441-48 (1975) ("Sanger & Coulson").
Ex. 1019, IPR2017-02172, Allan M. Maxam & Walter Gilbert, A New Method for Sequencing DNA, Proc. Natl. Acad. Sci. USA 74:560-64 (1977) ("Maxam & Gilbert").
Ex. 1020, IPR2017-02172, F. Sanger et al., DNA Sequencing with Chain-Termination Inhibitors, Proc. Natl. Acad. Sci. USA 74:5463-67 (1977) ("Sanger").
Ex. 1021, IPR2017-02172, Radoje Drmanac et al., Sequencing of Megabase Plus DNA by Hybridization, Genomics 4:114-28 (1989) ("Drmanac").
Ex. 1022, IPR2017-02172, Edwin Southern & William Cummings, U.S. Pat. No. 5,770,367 (Jun. 23, 1998).
Ex. 1023, IPR2017-02172, Aldrich Handbook of Fine Chemicals and Lab Ora Tory Equipment 2000-2001 (Sigma Aldrich Co. 2000).
Ex. 1024, IPR2017-02172, Bruno Canard & Robert S. Sarfati, DNA Polymerase Fluorescent Substrates with Reversible 3'-tags, Gene 148:1-6 (1994) ("Canard 1994").
Ex. 1025, IPR2017-02172, Robert A. Stockman, Book Review, J. Am. Chem. Soc. 122:426-26 (reviewing—Greene & Wuts) (2000).
Ex. 1026, IPR2017-02172, Joyce, C.M. Choosing the right sugar: How polymerases select a nucleotide substrate, Proc. Natl. Acad. Sci. USA 94:1619-1622 (Mar. 1997).
Ex. 1027, IPR2017-02172, Jari Hovinen et al., Synthesis of 3'-O-(w-Aminoalkoxymethyl)thymidine 5'-Triphosphates, Terminators of DNA Synthesis that Enable 3'-Labelling, J. Chem. Soc. Perkin Trans. 1:211-17 (1994).
Ex. 1028, IPR2017-02172, Yuri G. Gololobov & Leonid F. Kasukhin, Recent Advances in the Staudinger Reaction, Tetrahedron 48: 1353-406 (1992) ("Gololobov 1992").
Ex. 1029, IPR2017-02172, Eliana Saxon & Carolyn R. Bertozzi, Cell Surface Engineering by a Modified Staudinger Reaction, Science 287:2007-10 (2000) ("Saxon & Bertozzi").
Ex. 1030, IPR2017-02172, D.H. Dube and C.R. Bertozzi, Metabolic oligosaccharide engineering as a tool for glycobiology, Curr. Opin. Chem. Biol. 7:616-625 (2003).
Ex. 1031, IPR2017-02172, Eliana Saxon & Carolyn R. Bertozzi, U.S. Pub. 2002/0016003 AI, Chemoselective Ligation (published Feb. 7, 2002).
Ex. 1032, IPR2017-02172, Eliana Saxon et al., Investigating Cellular Metabolism of Synthetic Azidosugars with the Staudinger Ligation, 1. Am. Chem. Soc. 124:14893-902 (2002).
Ex. 1033, IPR2017-02172, Saul Kit, Deoxyribonucleic Acids, Annu. Rev. Biochem. 32:43-82 (1963) ("Kit").
Ex. 1034, IPR2017-02172, Che-Hung Lee et al., Unwinding of Double-stranded DNA Helix by Dehydration, Proc. Natl. Acad. Sci. USA 78:2838-42 (1981) ("Lee").
Ex. 1035, IPR2017-02172, Gordon et al., Abstract, Biophysical Society 6th Annual Meeting (Washington, 1962).

Ex. 1036, IPR2017-02172, Lawrence Levine et al., The Relationship of Structure to the Effectiveness of Denaturing Agents for Deoxyribonucleic Acid, Biochem. 2:168-75 (1963).
Ex. 1037, IPR2017-02172, Derek L. Stemple et al., U.S. Pat. No. 7,270,951 B1 (Sep. 18, 2007) ("Stemple III").
Ex. 1038, IPR2017-02172, Jingyue Ju et al., U.S. Pat. No. 6,664,079 B2 (Dec. 16, 2003) ("Ju").
Ex. 1039, IPR2017-02172, David Bentley et al., Accurate Whole Human Genome Sequencing Using Reversible Terminator Chemistry, Nature 456:53-59 (2008) ("Bentley").
Ex. 1040, IPR2017-02172, Elaine R. Mardis, A Decade's Perspective on DNA Sequencing Technology, Nature 470:198-203 (2011) ("Mardis").
Ex. 1041, IPR2017-02172, Michael L., Metzker, et al., Termination of DNA synthesis by novel 3'-modified deoxyribonucleoside 5'-triphosphates, Nuc. Acids Res. 22:4259-67 (1994) ("Metzker 1994").
Ex. 1042, IPR2017-02172, Bruno Canard et al., Catalytic Editing Properties of DNA Polymerases, Proc. Natl. Acad. Sci. USA 92: 10859-63 (1995) ("Canard 1995").
Ex. 1043, IPR2017-02172, Fabrice Guillier et al., Linkers and Cleavage Strategies in Solid-Phase Organic Synthesis and Combinatorial Chemistry, Chem. Rev. 100, 100 :2091-157 (2000) ("Guillier").
Ex. 1044, IPR2017-02172, Y.G. Gololobov et al., Sixty years of Staudinger reaction, Tetrahedron 37:437-72 (1981) ("Gololobov 1981").
Ex. 1045, IPR2017-02172, Kevin Davies, The British Invasion, in The $1,000 Genome: The Revolution in DNA Sequencing and the New Era of Personalized Medicine 102-15 (Ch. 5), 298-99 (Ch. 5 Notes) (2010) ("Davies").
Ex. 1046, IPR2017-02172, Vincent P. Stanton et al., WO 02/21098 A2 (published Sep. 5, 2000) ("Stanton").
Ex. 1047, IPR2017-02172, Seela, U.S. Pat. No. 4,804,748 (Feb. 14, 1989).
Ex. 1048, IPR2017-02172, Declaration of Michael Cohen (Sep. 28, 2017) Exhibit A: Filed as Ex. 1049 Exhibit B: Screenshot from the OCLC World Cat database Exhibit C: Definition of "date entered" from OCLC website Exhibit D: Screenshot of University of Wisconsin-Madison Library System Catalog Exhibit E: Spreadsheet of data extracted from Voyager Integrated Library System.
Ex. 1049, IPR2017-02172, Exhibit A to Declaration of Michael Cohen: Travis Young, A Strategy for the Synthesis of Sulfated Peptides, A dissertation submitted in partial fulfillment of the requirements for the degree of Doctor of Philosophy (Chemistry) at the University of Wisconsin-Madison (2001).
Ex. 1050, IPR2017-02172, Declaration of Thomas Hyatt (Sep. 28, 2017) (Attachment filed as Ex. 1051).
Ex. 1051, IPR2017-02172, Attachment to Declaration of Thomas Hyatt: Travis Young, A Strategy for the Synthesis of Sulfated Peptides, A dissertation submitted in partial fulfillment of the requirements for the degree of Doctor of Philosophy (Chemistry) at the University of Wisconsin-Madison (2001) ("Young").
Ex. 1052, IPR2017-02172, Declaration of Bonnie Phan (Sep. 28, 2017) Exhibit A: Dissertation Abstracts International, vol. 62, No. 7 (2002) (excerpts) Exhibit B: Guidelines to counsel & researchers seeking discovery from Stanford University Libraries, at https://library.stanford.edu/using/ special-policies/ guidelines-counsel-researchers-seeking -discovery-stanford-university (printed Sep. 28, 2017).
Ex. 1053, IPR2017-02172, Pentti Oksman et al., Solution Conformations and Hydrolytic Stability of 2'- and 3'-Substituted 2',3'-Dideoxyribonucleosides, Including some Potential Inhibitors of Human Immunodeficiency Virus, J. of Physical Organic Chem. 5:741-47 (1992) ("Oksman").
Ex. 1054, IPR2017-02172, Eric F.V. Scriven et al., Azides: Their Preparation and Synthetic Uses, Chemical Reviews 88:297-368 (1988).
Ex. 1055, IPR2017-02172, Peter C. Cheeseman, U.S. Pat. No. 5,302,509 (Apr. 12, 1994) ("Cheeseman").
Ex. 1056, IPR2017-02172, M. Vaultier et al., General Method to Reduce Azides to Primary Amines by Using the Staudinger Reaction, Tetrahedron Letters 24:763-64 (1983). including translation, supporting affidavit and original publication ("Vaultier").

(56) References Cited

OTHER PUBLICATIONS

Ex. 1057, IPR2017-02172, John A. Burns et al., Selective Reduction of Disulfides by Tris(2-carboxyethyltphosphine, J. of Organic Chem. 56:2648-2650 (1991).
Ex. 1058, IPR2017-02172, Anthony L. Handlon & Norman 1. Oppenheimer, Thiol Reduction of 3'-Azidothymidine to 3'-Aminothymidine: Kinetics and Biomedical Implications, Pharm. REs. 5:297-99 (1988) ("Handlon").
Ex. 1059, IPR2017-02172, Mark D. Uehling, Wanted: The $1000 Genome, Bio-IT World (Nov. 15, 2002), http://www.bio-itworld.com/archiveIII1202/genome (printed Oct. 2, 2017).
Ex. 1060, IPR2017-02172, Kevin Davies, 13 years ago, a beer summit in an English pub led to the birth of Solexa and—for now at least—the world's most popular second-generation sequencing technology, Bio-IT World (Sep. 28, 2010), http://www.bio-itworld.com/20 1 Olissues/sept-oct/solexa.html (printed Aug. 2, 2017).
Ex. 1061, IPR2017-02172, Wikipedia, Shankar Balasubramanian, https://en.wkipedia.org/wiki/Shankar_ Balasubramanian (last visited Aug. 2, 2017).
Ex. 1062, IPR2017-02172, Past Group Members—Balasubramanian Group, http://www.balasubramanian.co.uklpast-group-members (printed Aug. 2, 2017).
Ex. 1063, IPR2017-02172, Sarah Houlton, Profile: Flexibility on the move, Chemistry World (Nov. 29, 2010) https://www.chemistryworld.com/news/profile-flexibility-on-the-move/3003307.article (printed Aug. 2, 2017).
Ex. 1064, IPR2017-02172, LinkedIn, Harold Swerdlow, https://www.1inkedin.comlin/harold- swerdlow-9aa69811 (printed Aug. 2, 2017).
Ex. 1065, IPR2017-02172, LinkedIn, Xiaolin Wu, https://www.1inkedin.comlin/xiaolin-wu-68821313/?ppe=1 (printed Aug. 2, 2017).
Ex. 1066, IPR2017-02172, Xiaolin Wu, Synthesis of 5'-C- and 2'-O-Substituted Oligoribonucleotide Analogues and Evaluation of their Pairing Properties, A dissertation submitted in partial fulfillment of the requirements for the degree of Doctor of Nature Science at the Swiss Federal Institute of Technology (ETH) Zurich (2000).
Ex. 1067, IPR2017-02172, LinkedIn, Colin Barnes, https://www.1inkedin.comlin/colin-barnes-73678145/?ppe= 1 (printed Aug. 2, 2017).
Ex. 1068, IPR2017-02172, The Chinese Society of Chemical Science and Technology in the UK, Members of the Fourth Executive Committee, https://www.jiscmail.ac.uklcgi-bin/filearea.cgi?LMGT1=CHEM-CSCST-UK&A=get&f=/4cmmtt.htm (printed Aug. 2, 2017).
Ex. 1069, IPR2017-02172, Jonathan A. Eisen, Sequencing: The Now Generation, presentation at the Bodega Bay Applied Phylogenetics, slide 39 (Mar. 4, 2013), downloaded from http://treethinkers.org/wp-content/uploads/2013/01/EisenBodega20 13 .pdf.
Ex. 1071, IPR2017-02172, Illumina, Genome Analyzer System Specification Sheet (2007), http://www.geneworks.com.au/library/GenomeAnalyzer_SpecSheet.pdf (downloaded Oct. 2, 2017).
Ex. 1072, IPR2017-02172, A. Masoudi-Nejad et al., Emergence of Next-Generation Sequencing, Ch. 2 in Next Generation Sequencing and Sequence Assembly, 11-39,15 (2013).
Ex. 1073, IPR2017-02172, J. Bidwell et al., Cytokine gene polymorphism in human disease: on-line databases, Genes & Immunity 1:3-19 (1999) ("Bidwell").
Ex. 1074, IPR2017-02172, Pui-Yan Kwok, Methods for Genotyping Single Nucleotide Polymorphisms, Ann. Rev. Genomics Human Genetics 2:235-58 (2001) ("Kwok").
Ex. 1075, IPR2017-02172, Ann-Christine Syvanen, Accessing genetic variation: genotyping single nucleotide polymorphisms, Nature Reviews Genetics 2:920-942 (2001) ("Syvanen").
Ex. 1076, IPR2017-02172, A. A. Kraeveskii et al., Substrate inhibitors of DNA biosynthesis, Molecular Biology 21:25-29 (1987) ("Kraeveskii").
Ex. 1077, IPR2017-02172, William B. Parker et al., Mechanism of Inhibition of Human Immunodeficiency Virus Type 1 Reverse Transcriptase and Human DNA Polymerases α, β, and γ by the 5'-Triphosphates of Carbovir, 3'-Azido-3'-deoxythymidine, 2',3'-Dideoxyguanosine, and 3'-Deoxythymidine, J. Biol. Chem. 266:1754-1762 (1991) ("Parker").
Ex. 1078, IPR2017-02172, Elise Burmeister Getz et al., A comparison between the Suljhydryl reductants Tris(2-carboxyethyljphosphine and Dithiothreitol for Use in Protein Biochemistry, Analytical Biochem. 273 :73-80 (1999) ("Getz").
Ex. 1079, IPR2017-02172, William S. Mungall et al., Use of the Azido Group in the Synthesis of 5'-Terminal Aminodeoxythymidine Oligonucleotides, J. Org. Chem. 40:1659-1662 (1975) ("Mungall").
Ex. 1080, IPR2017-02172, Serge Pilard et al., A stereospecific synthesis of (+) a-conhydrine and (+β-conhydrine, Tetrahedron Letters 25:1555-56 (1984).
Ex. 1081, IPR2017-02172, R. Ranganathan et al., Facile conversion of adenosine into new 2'-substituted-2'-deoxy-arabinofuranosyladenine derivatives: stereospecific syntheses of 2'-azido-2'-deoxy-, 2'-amino-2'deoxy-, and 2'-mercapto-40 deoxy-β-D-arabinofuranosyladenines, Tetrahedron Letters 45:4341-4344 (1978).
Ex. 1082, IPR2017-02172, K.S. Kirby, A New Method for the Isolation of Deoxyribonucleic Acids: Evidence on the Nature of Bonds between Deoxyribonucleic Acid and Protein, Biochem. J. 66:495-504 (1957) ("Kirby").
Ex. 1083, IPR2017-02172, David Moore & Dennis Dowhan, 2.1.1—Manipulation of DNA in Current Protocols in Molecular Biology (Wiley, 2002) ("Moore").
Ex. 1084, IPR2017-02172, G.E. Tiller et al., Dinucleotide insertion/deletion polymorphism in intron 50 of the COL2A1 gene, Nucleic Acids Research, 19,4305 (1991) ("Tiller").
Ex. 1085, IPR2017-02172, *Kamada, Ltd.* v. *Grifols Therapeutics Inc.*, IPR2014-00899, Paper 22 (Mar. 4, 2015).
Ex. 1086, IPR2017-02172, Summary Table of Prior IPR Proceedings, filed Oct. 25, 2017.
Ex. 1087, IPR2017-02172, 2014-1547, Appellee's Brief (Dec. 29, 2014) (appeal of IPR2012-00006).
Ex. 1088, IPR2017-02172, IPR2013-00518, Paper 28, Illumina Request for Adverse Judgment (May 5, 2014).
Ex. 1089, IPR2017-02172, IPR2013-00518, Paper 29, Judgment Request for Adverse Judgment (May 6, 2014).
Ex. 1090, IPR2017-02172, IPR2013-00517, Paper 7, Revised Petition for Inter Partes Review of U.S. Pat. No. 7,566,537 (Aug. 13, 2013).
Ex. 1091, IPR2017-02172, IPR2013-00517, Paper 16, Decision—Institution of Inter Partes Review (Feb. 13, 2014).
Ex. 1092, IPR2017-02172, IPR2013-00517, Paper 32, Illumina's Patent Owner Response (May 5, 2014) (Redacted).
Ex. 1093, IPR2017-02172, IPR2013-00517, Paper 54, Petitioner IBS's Reply (Jul. 28, 2014) (Redacted).
Ex. 1094, IPR2017-02172, IPR2013-00517, Paper 87, Final Written Decision (Feb. 11, 2015).
Ex. 1095, IPR2017-02172, 2015-1693, Brief of Patent Owner-Appellee Illumina Cambridge Ltd. (Oct. 28, 2015).
Ex. 1097, IPR2017-02172, *Illumina, Inc.* v. *Qiagen, N.V* (N.D. Cal, Aug. 25, 2016) Plaintiffs Reply in Support of Motion for Preliminary Injunction.
Ex. 1098, IPR2017-02172, IPR2013-00517, Ex. 2011, Declaration of Floyd Romesberg, Ph.D. (May 5, 2014) (Redacted) ("Romesberg Decl.").
Ex. 1099, IPR2017-02172, IPR2013-00517, Ex. 2089, Declaration of Dr. Kevin Burgess (May 5, 2014) (Redacted) ("Burgess Decl.").
Ex. 1100, IPR2017-02172, IPR2013-00517, Ex. 1026, Transcript, Jul. 15, 2014 Deposition of Kevin Burgess, Ph.D. (Redacted).
Ex. 1101, IPR2017-02172, Declaration of John D. Sutherland (IPR2017-02172) ("Sutherland Decl.") , filed Oct. 5, 2017.
Ex. 1102, IPR2017-02172, Curriculum Vitae of Dr. John D. Sutherland, filed Oct. 5, 2017.
Ex. 1103, IPR2017-02172, IPR2012-00006, Paper 128, Final Written Decision (Feb. 11, 2015).
Ex. 1104, IPR2017-02172, IPR2013-0011, Paper 4, Petition for Inter Partes Review of U.S. Pat. No. 8,088,575 (Aug. 3, 2012).
Exhibit 2001 filed Jan. 23, 2018, IPR2017-02172, Eileen Zimmerman, Mar./Apr. 2014, The 50 Smartest Companies, MIT Tech Review, 117(2):Cover, 2, 4, 27-29.

(56) References Cited

OTHER PUBLICATIONS

Exhibit 2002 filed Jan. 23, 2018, IPR2017-02172, Goodwin, et al., 2016, Coming of age: ten years of next-generation sequencing technologies, Nature Reviews, 17:333-351.
Exhibit 2003 filed Jan. 23, 2018, IPR2017-02172, Complete Genomics, www.completegenomics.com, downloaded Jan. 15, 2018.
Exhibit 2004 filed Jan. 23, 2018, IPR2017-02172, Fehlmann et al., 2016, cPAS-based sequencing on the BGISEQ-500 to explore small non-coding RNAs, Clinical Epigenetics, 8:123.
Exhibit 2005 filed Jan. 23, 2018, IPR2017-02172, Julia Karow, Nov. 9, 2017. BGI's MGI tech launches new sequencing platforms, broadens scope with diagnostic ultrasound system. GenomeWeb.
Exhibit 2006 filed Jan. 23, 2018, IPR2017-02172, WO 00/53805, published Sep. 14, 2000, Stemple et al.
Exhibit 2007 filed Jan. 23, 2018, IPR2017-02172, WO 01/92284, published Dec. 6, 2001, Amershan Pharmacia Biotech UK Limited.
Exhibit 2008 filed Jan. 23, 2018, IPR2017-02172, U.S. Pat. No. 7,279,563, issued Oct. 9, 2007, Kwiatkowski.
Exhibit 2009 filed Jan. 23, 2018, IPR2017-02172, WO 96/023807, published Aug. 8, 1996, Kwiatkowski.
Exhibit 2010 filed Jan. 23, 2018, IPR2017-02172, WO 93/21340, published Oct. 28, 1993, Medical Research Council.
Exhibit 2011 filed Jan. 23, 2018, IPR2017-02172, WO 96/27025, published Sep. 6, 1996, Rabani.
Exhibit 2012 filed Jan. 23, 2018, IPR2017-02172, QIAGEN press release, QIAGEN agrees with BGI Tech to provide services based on the Human Gene Mutation Database (HGMD) in Greater China, https://corporate.qiagen.com/newsroom/press-releases/2017/20140729_bgi_hgmd, Jul. 29, 2014.
Exhibit 2013 filed Jan. 23, 2018, IPR2017-02172, QIAGEN press release, QIAGEN partners with world's largest sequencing provider, https://corporate.qiagen.com/newsroom/press-releases/2017/20150504_bgi_iva_partnership, May 4, 2015.
Exhibit 2018 filed Jan. 23, 2018, IPR2017-02172, IDS filed on May 6, 2010 by CGI in U.S. Appl. No. 11/981,797.
Exhibit 2019 filed Jan. 23, 2018, IPR2017-02172, IDS filed on Oct. 7, 2010 by CGI in U.S. Appl. No. 12/266,385.
Exhibit 2021 filed Jan. 23, 2018, IPR2017-02172, IDS filed on Aug. 10, 2016 by CGI in U.S. Appl. No. 14/921,466.
Exhibit 2020 filed Jan. 23, 2018, IPR2017-02172, IDS filed on Aug. 30, 2010 by CGI in U.S. Appl. No. 12/329,365.
Exhibit 2022 filed Jan. 23, 2018, IPR2017-02172, Peter G. M. Wuts, 2007, Preface to the Fourth Edition, in Greene's Protective Groups in Organic Synthesis, Greene & Wuts (Eds.), Hoboken, NJ: John Wiley & Sons.
Exhibit 2023 filed Jan. 23, 2018, IPR2017-02172, Excerpt from Branchaud Apr. 8, 2014 transcript in IPR2013-00517 & IPR-2013-000518, pp. 1-5, 104-106, 183.
Exhibit 2024 filed Jan. 23, 2018, IPR2017-02172, Declaration of Floyd Romesberg, Ph.D., dated Jan. 22, 2018.
Exhibit 2025 filed Jan. 23, 2018, IPR2017-02172, Romesberg CV, updated Oct. 2017.
Exhibit 2026 filed Jan. 23, 2018, IPR2017-02172, Suzuki et al., 1994, Mechanistic studies on depurination and apurinic site chain breakage in oligodeoxyribonucleotides, Nucleic Acids Research, 22(23):4997-5003.
Exhibit 2027 filed Jan. 23, 2018, IPR2017-02172, A. Treinin, 1971, General and theoretical aspects, in The Chemistry of the Azido Group, Saul Patai (Ed.), John Wiley & Sons, pp. 1-55.
Exhibit 2028 filed Jan. 23, 2018, IPR2017-02172, Excerpt from Romesberg Jul. 8, 2014 transcript in IPR2013-00517, pp. 1-7, 70-73, 191, Errata (3 pages), 190.
Exhibit 2029 filed Jan. 23, 2018, IPR2017-02172, Wu et al., 2007, Termination of DNA synthesis by $N^6$-alkylated, not 3'-O-alkylated, photocleavable 2'-deoxyadenosine triphosphates, Nucleic Acids Research, 35(19):6339-6349.
Exhibit 2030 filed Jan. 23, 2018, IPR2017-02172, Boyer et al., 2001, Selective excision of AZTMP by drug-resistant human immunodeficiency virus reverse transcriptase, Journal of Virology, 75(10):4832-4842.

Exhibit 2031 filed Jan. 23, 2018, IPR2017-02172, Paper 64, submitted Sep. 2, 2014, IPR2013-00517, Illumina's Motion for Observations on the Cross-Examination Testimony of Bruce Branchaud, Ph.D. and Michael Metzker, Ph.D.
Exhibit 2032 filed Jan. 23, 2018, IPR2017-02172, The Merck Index, 13th Ed., 2001, Triphenylphosphine Chloride, M. J. O'Neil, A. Smith, & P. E. Heckelman (Eds.), Whitehouse Station, NJ: Merck & Co., Inc., p. 1735.
Exhibit 2033 filed Jan. 23, 2018, IPR2017-02172, Dantas et al., 1999, Stannous chloride mediates single strand breaks in plasmid DNA through reaactive oxygen species formation, Toxicology Letters, 110:129-136.
Exhibit 2034 filed Jan. 23, 2018, IPR2017-02172, Excerpt from Branchaud Aug. 26, 2014 transcript in IPR2013-00517, pp. 1-5, 44, 45, 333, E-1-E7.
Exhibit 2035 filed Jan. 23, 2018 IPR2017-02172, Radom et al., 1971, Molecular orbital theory of the electronic structure of organic compounds. VIII. Geometries, energies, and polarities of $C_3$ hydrocarbons, J Am Chem Soc, 93(21):5339-5342.
Exhibit 2036 filed Jan. 23, 2018, IPR2017-02172, Nielsen et al., 1987, The vibrational spectra, molecular structure and conformation of organic azides. Part IV. An ab initio study of hydrazoic acid, azidomethane, azidoethane, azidoethene and azidomethanal, J. Molecular Structure, 150:361-379.
Exhibit 2037 filed Jan. 23, 2018, IPR2017-02172, Swarts et al., 1996, Effects of formic acid hydrolysis on the quantitative analysis of radiation-induced DNA base damage products assayed by gas chromatography/mass spectrometry, Radiat. Environ. Biophys, 35:41-53.
Exhibit 2039 filed Feb. 14, 2018, IPR2017-02172, Declaration of Wm. Zimmerman in Support of Unopposed Pro Hac Vice Motion, dated Feb. 14, 2018.
Exhibit 1105 filed Feb. 28, 2018, IPR2017-02172, Illumina Press Release dated Jan. 12, 2010.
Exhibit 1106 filed Feb. 28, 2018, IPR2017-02172, Declaration of Katie J.L. Scott in Support of Petitioner's Motion for Admission Pro Hac Vice, dated Feb. 28, 2019.
Paper 3 filed Oct. 23, 2017, IPR2017-02172, Notice of Accord Filing Date.
Paper 6 filed Jan. 23, 2018, IPR2017-02172, Illumina Patent Owner Preliminary Response.
Paper 7 filed Jan. 23, 2018, IPR2017-02172, Illumina Exhibit List.
Paper 8 filed Feb. 14, 2018, IPR2017-02172, Illumina Unopposed Motion for William Zimmerman to Appear Pro Hac Vice.
Paper 9 filed Feb. 14, 2018, IPR2017-02172, Illumina Updated Exhibit List.
Paper 10 filed Feb. 14, 2018, IPR2017-02172, Illumina Supplemental POA for William Zimmerman.
Paper 11 filed Feb. 21, 2018, IPR2017-02172, Conduct of the Proceeding.
Paper 12 filed Feb. 21, 2018, IPR2017-02172, Patent Owner's Motion for Admission Pro Hac Vice of William R. Zimmerman.
Paper 13 filed Feb. 28, 2018, IPR2017-02172, Order—Conduct of the Proceeding.
Paper 14 filed Feb. 28, 2018, IPR2017-02172, CGI's Reply to Patent Owner's Preliminary Response.
Paper 15 filed Feb. 28, 2018, IPR2017-02172, Petitioner's Unopposed Motion for Admission of Katie J.L. Scott to Appear Pro Hac Vice.
Paper 16 filed Feb. 28, 2018, IPR2017-02172, Petitioner's Updated Exhibit List.
Paper 17, filed Mar. 5, 2018, IPR2017-02172, Illumina's Sur-Reply to Petitioner's Reply to Preliminary Response.
Paper 18, filed Mar. 7, 2018, IPR2017-02172, Illumina Supp'l Mandatory Notice Adding Zimmerman as Backup Counsel.
Paper 19 filed Apr. 6, 2018, IPR2017-02172, Illumina Supp'l Mandatory Notice—Related Matters.
Decision Denying Institution of Inter Partes Review in IPR2017-02172, U.S. Pat. No. 7,566,537 B2, dated Apr. 20, 2018.
Petition for Inter Partes Review of U.S. Pat. No. 7,566,537 B2, IPR2017-02174, filed Oct. 5, 2017.
Ex. 1501, IPR2017-02174, Shankar Balasubramanian et al., U.S. Pat. No. 7,566,537 B2 (Jul. 28, 2009) ("'537").

(56) References Cited

OTHER PUBLICATIONS

Ex. 1502 Excerpts of File History of U.S. Appl. No. 11/301,478, filed Oct. 5, 2017.
Ex. 1503, IPR2017-02174, Roger Y. Tsien et al., WO 91/06678 Al (published May 16, 1991) ("Tsien").
Ex. 1504, IPR2017-02174, William J. Dower et al., U.S. Pat. No. 5,547,839 (Aug. 20, 1996) ("Dower").
Ex. 1505, IPR2017-02174, Protective Groups in Organic Synthesis (Theodora W. Greene & Peter G.M. Wuts eds., 3rd ed. 1999) (excerpts) ("Greene & Wuts").
Ex. 1506, IPR2017-02174, Bernard Loubinoux et al., Protection of Phenols by the Azidomethylene Group Application to the Synthesis of Unstable Phenols, Tetrahedron 44:6055-64 (1988), including translation, supporting affidavit and original publication ("Loubinoux").
Ex. 1507, IPR2017-02174, James M. Prober et al., A System for Rapid DNA Sequencing with Fluorescent Chain-Terminating Dideoxynucleotides, Science 238:336-41 (1987) ("Prober").
Ex. 1508 IPR2017-02174, Sergey Zavgorodny et al., 1-Alkylthioalkylation of Nucleoside Hydroxyl Functions and Its Synthetic Applications, Tetrahedron Letters 32:7593-96 (1991) ("Zavorodny").
Ex. 1509, IPR2017-02174, S.G. Zavgorodny et al., S,X-Acetals in Nucleoside Chemistry, III, Synthesis of 2'- and 3'-O-Azidomethyl Derivatives of Ribonucleosides, Nucleosides, Nucleotides & Nucleic Acids 19: 1977-91 (2000) ("Zavgorodny 2000").
Ex. 1510, IPR2017-02174, J.D. Watson & F.H.C. Crick, Molecular Structure of Nucleic Acids, Nature 171:737-38 (1953).
Ex. 1511, IPR2017-02174, Steven M. Carr, Deoxyribose versus Ribose Sugars (2014), at https://www.mun.ca/biology/scarrlRibose_sugar.html (downloaded Sep. 25, 017).
Ex. 1512, IPR2017-02174, Michael L. Metzker, Emerging Technologies in DNA Sequencing, Genome Res. 15: 1767-76 (2005) ("Metzker 2005").
Ex. 1513, IPR2017-02174, A. Kornberg et al., Enzymatic Synthesis of deoxyribonucleic acid, Biochim. Biophys. Acta 21:197-198 (1956) ("Kornberg").
Ex. 1514, IPR2017-02174, Bruce Merrifield, Solid Phase Synthesis, Science 232:341-47 (1986) ("Merrifield").
Ex. 1515, IPR2017-02174, William C. Copeland et al., Human DNA Polymerases α and β Are Able to Incorporate Anti-HIV Deoxynucleotides Into DNA, J. Biol. Chem. 267 :21459-64 (1992) ("Copeland").
Ex. 1516, IPR2017-02174, Hamilton O. Smith & K.W. Wilcox, A Restriction Enzyme from Hemophilus influenzae. 1. Purification and General Properties, J. Mol. Biol. 51:379-91 (1970).
Ex. 1517, IPR2017-02174, Thomas J. Kelly, Jr. & Hamilton O. Smith, A restriction enzyme from Hemophilus influenzae. II. Base sequence of the recognition site, J. Mol. Biol. 51:393-409 (1970).
Ex. 1518, IPR2017-02174, F. Sanger & A.R. Coulson, A Rapid Method for Determining Sequences in DNA by Primed Synthesis with DNA Polymerase, J. Mol. Biol. 94: 441-48 (1975) ("Sanger & Coulson").
Ex. 1519, IPR2017-02174, Allan M. Maxam & Walter Gilbert, A New Method for Sequencing DNA, Proc. Natl. Acad. Sci. USA 74:560-64 (1977) ("Maxam & Gilbert").
Ex. 1520, IPR2017-02174, F. Sanger et al., DNA Sequencing with Chain-Termination Inhibitors, Proc. Natl. Acad. Sci. USA 74:5463-67 (1977) ("Sanger").
Ex. 1521, IPR2017-02174, Radoje Drmanac et al., Sequencing of Megabase Plus DNA by Hybridization, Genomics 4:114-28 (1989) ("Drmanac").
Ex. 1522, IPR2017-02174, Edwin Southern & William Cummings, U.S. Pat. No. 5,770,367 (Jun. 23, 1998).
Ex. 1523, IPR2017-02174, Aldrich Handbook of Fine Chemicals and Laboratory Equipment 2000-2001 (Sigma Aldrich Co. 2000).
Ex. 1524, IPR2017-02174, Bruno Canard & Robert S. Sarfati, DNA Polymerase Fluorescent Substrates with Reversible 3'-tags, Gene 148:1-6 (1994) ("Canard 1994").
Ex. 1525, IPR2017-02174, Robert A. Stockman, Book Review, 1. Am. Chem. Soc. 122:426-26 (reviewing—Greene & Wuts) (2000).

Ex. 1526, IPR2017-02174, Joyce, C.M. Choosing the right sugar: How polymerases select a nucleotide substrate, Proc. Natl. Acad. Sci. USA 94:1619-1622 (Mar. 1997).
Ex. 1527, IPR2017-02174, Jari Hovinen et al., Synthesis of 3'-O-(ω-Aminoalkoxymethyl)thymidine 5'Triphosphates, Terminators of DNA Synthesis that Enable 3'-Labelling, J. Chem. Soc. Perkin Trans. 1:211-17 (1994).
Ex. 1528, IPR2017-02174, Yuri G. Gololobov & Leonid F. Kasukhin, Recent Advances in the Staudinger Reaction, Tetrahedron 48: 1353-406 (1992) ("Gololobov 1992").
Ex. 1529, IPR2017-02174, Eliana Saxon & Carolyn R. Bertozzi, Cell Surface Engineering by a Modified Staudinger Reaction, Science 287:2007-10 (2000) ("Saxon & Bertozzi").
Ex. 1530, IPR2017-02174, D.H. Dube and C.R. Bertozzi, Metabolic oligosaccharide engineering as a tool for glycobiology, Curr. Opin. Chem. Biol. 7:616-625 (2003).
Ex. 1531, IPR2017-02174, Eliana Saxon & Carolyn R. Bertozzi, U.S. Pub. 2002/0016003 AI, Chemoselective Ligation (published Feb. 7, 2002).
Ex. 1532, IPR2017-02174, Eliana Saxon et al., Investigating Cellular Metabolism of Synthetic Azidosugars with the Staudinger Ligation, 1. Am. Chem. Soc. 124:14893-902 (2002).
Ex. 1533, IPR2017-02174, Saul Kit, Deoxyribonucleic Acids, Annu. Rev. Biochem. 32:43-82 (1963) ("Kit").
Ex. 1534, IPR2017-02174, Che-Hung Lee et al., Unwinding of Double-stranded DNA Helix by Dehydration, Proc. Natl. Acad. Sci. USA 78:2838-42 (1981) ("Lee").
Ex. 1535, IPR2017-02174, Gordon et al., Abstract, Biophysical Society 6th Annual Meeting (Washington, 1962).
Ex. 1536, IPR2017-02174, Lawrence Levine et al., The Relationship of Structure to the Effectiveness of Denaturing Agents for Deoxyribonucleic Acid, Biochem. 2:168-75 (1963).
Ex. 1537, IPR2017-02174, Derek L. Stemple et al., U.S. Pat. No. 7,270,951 B1 (Sep. 18, 2007) ("Stemple III").
Ex. 1538, IPR2017-02174, Jingyue Ju et al., U.S. Pat. No. 6,664,079 B2 (Dec. 16, 2003) ("Ju").
Ex. 1539, IPR2017-02174, David Bentley et al., Accurate Whole Human Genome Sequencing Using Reversible Terminator Chemistry, Nature 456:53-59 (2008) ("Bentley").
Ex. 1540, IPR2017-02174, Elaine R. Mardis, A Decade's Perspective on DNA Sequencing Technology, Nature 470:198-203 (2011) ("Mardis").
Ex. 1541, IPR2017-02174, Michael L., Metzker, et al., Termination of DNA synthesis by novel 3'-modified deoxyribonucleoside 5'-triphosphates, Nuc. Acids Res. 22:4259-67 (1994) ("Metzker 1994").
Ex. 1542, IPR2017-02174, Bruno Canard et al., Catalytic Editing Properties of DNA Polymerases, Proc. Natl. Acad. Sci. USA 92: 10859-63 (1995) ("Canard 1995").
Ex. 1543, IPR2017-02174, Fabrice Guillier et al., Linkers and Cleavage Strategies in Solid-Phase Organic Synthesis and Combinatorial Chemistry, Chem. Rev. 100, 100 :2091-157 (2000) ("Guillier").
Ex. 1544, IPR2017-02174, Y.G. Gololobov et al., Sixty years of Staudinger reaction, Tetrahedron 37:437-72 (1981) ("Gololobov 1981").
Ex. 1545, IPR2017-02174, Kevin Davies, The British Invasion, in the $1,000 Genome: The Revolution in DNA Sequencing and the New Era of Personalized Medicine 102-15 (Ch. 5),298-99 (Ch. 5 Notes) (2010) ("Davies").
Ex. 1546, IPR2017-02174, Vincent P. Stanton et al., WO 02/21098 A2 (published Sep. 5, 2000) ("Stanton").
Ex. 1547, IPR2017-02174, Seela, U.S. Pat. No. 4,804,748 (Feb. 14, 1989).
Ex. 1548, IPR2017-02174, Declaration of Michael Cohen (Sep. 28, 2017) (Exhibit A filed as Ex. Exhibit B: Screenshot from the OCLC WorldCat database Exhibit C: Definition of "date entered" from OCLC website Exhibit D: Screenshot of University of Wisconsin-Madison Library System Catalog Exhibit E: Spreadsheet of data extracted from Voyager Integrated Library System.
Ex. 1549, IPR2017-02174, Exhibit A to Declaration of Michael Cohen: Travis Young, A Strategy for the Synthesis of Sulfated Peptides, A dissertation submitted in partial fulfillment of the

(56) References Cited

OTHER PUBLICATIONS requirements for the degree of Doctor of Philosophy (Chemistry) at the University of Wisconsin-Madison (2001) ("Young").
Ex. 1550, IPR2017-02174, Declaration of Thomas Hyatt (Sep. 28, 2017) (Attachment filed as Ex. 1051).
Ex. 1551, IPR2017-02174, Attachment to Declaration of Thomas Hyatt: Travis Young, A Strategy for the Synthesis of Sulfated Peptides, A dissertation submitted in partial fulfillment of the requirements for the degree of Doctor of Philosophy (Chemistry) at the University of Wisconsin-Madison (2001) ("Young").
Ex. 1552, IPR2017-02174, Declaration of Bonnie Phan (Sep. 28, 2017) Exhibit A: Dissertation Abstracts International, vol. 62, No. 7 (2002) (excerpts) Exhibit B: Guidelines to counsel & researchers seeking discovery from Stanford University Libraries, at https://library.stanford.edu/using/ special-policies/ guidelines-counsel-researchers-seeking -discovery-stanford-university (printed Sep. 28, 2017).
Ex. 1553, IPR2017-02174, Pentti Oksman et al., Solution Conformations and Hydrolytic Stability of 2'- and 3'-Substituted 2',3'-Dideoxyribonucleosides, Including some Potential Inhibitors of Human Immunodeficiency Virus, J. of Physical Organic Chem. 5:741-47 (1992) ("Oksman").
Ex. 1554, IPR2017-02174, Eric F.V. Scriven et al., Azides: Their Preparation and Synthetic Uses, Chemical Reviews 88:297-368 (1988).
Ex. 1555, IPR2017-02174, Peter C. Cheeseman, U.S. Pat. No. 5,302,509 (Apr. 12, 1994) ("Cheeseman").
Ex. 1556, IPR2017-02174, M. Vaultier et al., General Method to Reduce Azides to Primary Amines by Using the Staudinger Reaction, Tetrahedron Letters 24:763-64 (1983). including translation, supporting affidavit and original publication ("Vaultier").
Ex. 1557, IPR2017-02174, John A. Burns et al., Selective Reduction of Disulfides by Tris(2-carboxyethyltphosphine, J. of Organic Chem. 56:2648-2650 (1991) ("Burns").
Ex. 1558, IPR2017-02174, Anthony L. Handlon & Norman 1. Oppenheimer, Thiol Reduction of 3'-Azidothymidine to 3'-Aminothymidine: Kinetics and Biomedical Implications, Pharm. Res. 5:297-99 (1988) ("Handlon").
Ex. 1559, IPR2017-02174, Mark D. Uehling, Wanted: The $1000 Genome, Bio-IT World (Nov. 15, 2002), http://www.bio-itworld.com/archiveIII1202/genome (printed Oct. 2, 2017).
Ex. 1560, IPR2017-02174, Kevin Davies, 13 years ago, a beer summit in an English pub led to the birth of Solexa and—for now at least—the world's most popular second-generation sequencing technology, Bio-IT World (Sep. 28, 2010), http://www.bio-itworld.com/20 1 Olissues/sept-oct/solexa.html (printed Aug. 2, 2017).
Ex. 1561, IPR2017-02174, Wikipedia, Shankar Balasubramanian, https://en.wikipedia.org/wiki/Shankar_ Balasubramanian (last visited Aug. 2, 2017).
Ex. 1562, IPR2017-02174, Past Group Members—Balasubramanian Group, http://www.balasubramanian.co.uklpast-group-members (printed Aug. 2, 2017).
Ex. 1563, IPR2017-02174, Sarah Houlton, Profile: Flexibility on the move, Chemistry World (Nov. 29, 2010) https://www.chemistryworld.com/news/profile-flexibility-on-the-move/3003307.article (printed Aug. 2, 2017).
Ex. 1564, IPR2017-02174, LinkedIn, Harold Swerdlow, https://www.1inkedin.comlin/harold-swerdlow-9aa69811, (printed Aug. 2, 2017).
Ex. 1565, IPR2017-02174, LinkedIn, Xiaolin Wu, https://www.1inkedin.comlin/xiaolin-wu-688213131?ppe=1 (printed Aug. 2, 2017).
Ex. 1566, IPR2017-02174, Xiaolin Wu, Synthesis of 5'-C- and 2'-O-Substituted Oligoribonucleotide Analogues and Evaluation of their Pairing Properties, A dissertation submitted in partial fulfillment of the requirements for the degree of Doctor of Nature Science at the Swiss Federal Institute of Technology (ETH) Zurich (2000).
Ex. 1567, IPR2017-02174, LinkedIn, Colin Barnes, https:!/www.1inkedin.comlin/colin-barnes-73678145/?ppe= 1 (printed Aug. 2, 2017).

Ex. 1568, IPR2017-02174, The Chinese Society of Chemical Science and Technology in the UK, Members of the Fourth Executive Committee, https:!/www.jiscmail.ac.uklcgi-bin/filearea.cgi?LMGTI=CHEM-CSCST-UK&a=get&f=/4cmmtt.htm (printed Aug. 2, 2017).
Ex. 1569, IPR2017-02174, Jonathan A. Eisen, Sequencing: The Now Generation, presentation at the Bodega Bay Applied Phylogenetics, slide 39 (Mar. 4, 2013), downloaded from http://treethinkers.org/wp-content/uploads/20 13/0 llEisenBodega20 13 .pdf.
Ex. 1571, IPR2017-02174, Illumina, Genome Analyzer System Specification Sheet (2007), http://www.geneworks.com.au/library/GenomeAnalyzer_SpecSheet.pdf (downloaded Oct. 2, 2017).
Ex. 1572, IPR2017-02174, A. Masoudi-Nejad et al., Emergence of Next-Generation Sequencing, Ch. 2 in Next Generation Sequencing and Sequence Assembly, 11-39,15 (2013).
Ex. 1573, IPR2017-02174, J. Bidwell et al., Cytokine gene polymorphism in human disease: on-line databases, Genes & Immunity 1:3-19 (1999) ("Bidwell").
Ex. 1574, IPR2017-02174, Pui-Yan K wok, Methods for Genotyping Single Nucleotide Polymorphisms, Ann. Rev. Genomics Human Genetics 2:235-58 (2001) ("Kwok").
Ex. 1575, IPR2017-02174, Ann-Christine Syvanen, Accessing genetic variation: genotyping single nucleotide polymorphisms, Nature Reviews Genetics 2:920-942 (2001) ("Syvanen").
Ex. 1576, IPR2017-02174, A. A. Kraeveskii et al., Substrate inhibitors of DNA biosynthesis, Molecular Biology 21:25-29 (1987) ("Kraeveskii").
Ex. 1577, IPR2017-02174, William B. Parker et al., Mechanism of Inhibition of Human Immunodeficiency Virus Type 1 Reverse Transcriptase and Human DNA Polymerases α, β, and γ by the 5'-Triphosphates of Carbovir, 3'-Azido-3'-deoxythymidine, 2',3'-Dideoxyguanosine, and 3'-Deoxythymidine, J. Biol. Chem. 266:1754-1762 (1991) ("Parker").
Ex. 1578, IPR2017-02174, Elise Burmeister Getz et al., A comparison between the Suljhydryl reductants Tris(2-carboxyethyljphosphine and Dithiothreitol for Use in Protein Biochemistry, Analytical Biochem. 273 :73-80 (1999) ("Getz").
Ex. 1579, IPR2017-02174, William S. Mungall et al., Use of the Azido Group in the Synthesis of 5'-Terminal Am inodeoxythymidine Oligonucleotides, J. Org. Chem. 40:1659-1662 (1975) ("Mungall").
Ex. 1580, IPR2017-02174, Serge Pilard et al., A stereospecific synthesis of (+) α-conhydrine and (+) β-conhydrine, Tetrahedron Letters 25:1555-56 (1984).
Ex. 1581, IPR2017-02174, R. Ranganathan et al., Facile conversion of adenosine into new 2'-substituted-2'-deoxy-arabinofuranosyladenine derivatives: stereospecific syntheses of 2'-azido-2'-deoxy-, 2'-amino-2'deoxy-, and 2'-mercapto-2'deoxy-fJ-D-arabinofuranosyladenines, Tetrahedron Letters 45:4341-4344 (1978).
Ex. 1582, IPR2017-02174, K.S. Kirby, A New Method for the Isolation of Deoxyribonudeic Acids: Evidence on the Nature of Bonds between Deoxyribonucleic Acid and Protein, Biochem. J. 66:495-504 (1957) ("Kirby").
Ex. 1583, IPR2017-02174, David Moore & Dennis Dowhan, 2.1.1—Manipulation of DNA in Current Protocols in Molecular Biology (Wiley, 2002) ("Moore").
Ex. 1584, IPR2017-02174, G.E. Tiller et al., Dinucleotide insertion/deletion polymorphism in intron 50 of the COL2A1 gene, Nucleic Acids Research 19,4305 (1991) ("Tiller").
Ex. 1585, IPR2017-02174, *Kamada, Ltd.* v. *Grifols Therapeutics Inc.*, IPR2014-00899, Paper 22 (Mar. 4, 2015).
Ex. 1586, IPR2017-02174, Summary Table of Prior IPR Proceedings, filed Oct. 5, 2017.
Ex. 1587, IPR2017-02174, 2014-1547, Appellee's Brief (Dec. 29, 2014) (appeal of IPR2012-00006).
Ex. 1588, IPR2017-02174, IPR2013-00518, Paper 28, Illumina Request for Adverse Judgment (May 5, 2014).
Ex. 1589, IPR2017-02174, IPR2013-00518, Paper 29, Judgment Request for Adverse Judgment (May 6, 2014).
Ex. 1590, IPR2017-02174, IPR2013-00517, Paper 7, Revised Petition for Inter Partes Review of U.S. Pat. No. 7,566,537 (Aug. 13, 2013).
Ex. 1591, IPR2017-02174, IPR2013-00517, Paper 16, Decision—Institution of Inter Partes Review (Feb. 13, 2014).

(56) References Cited

OTHER PUBLICATIONS

Ex. 1592, IPR2017-02174, IPR2013-00517, Paper 32, Illumina's Patent Owner Response (May 5, 2014) (Redacted).
Ex. 1593, IPR2017-02174, IPR2013-00517, Paper 54, Petitioner IBS's Reply (Jul. 28, 2014) (Redacted).
Ex. 1594, IPR2017-02174, IPR2013-00517, Paper 87, Final Written Decision (Feb. 11, 2015).
Ex. 1595, IPR2017-02174, 2015-1693, Brief of Patent Owner-Appellee Illumina Cambridge Ltd. (Oct. 28, 2015).
Ex. 1597, IPR2017-02174, *Illumina, Inc. v. Qiagen, N.V* (N.D. Cal, Aug. 25, 2016) Plaintiffs Reply in Support of Motion for Preliminary Injunction.
Ex. 1598, IPR2017-02174, IPR2013-00517, Ex. 2011, Declaration of Floyd Romesberg, Ph.D. (May 5, 2014) (Redacted) ("Romesberg Decl.").
Ex. 1599, IPR2017-02174, IPR2013-00517, Ex. 2089, Declaration of Dr. Kevin Burgess (May 5, 2014) (Redacted) ("Burgess Decl.").
Ex. 1600, IPR2017-02174, IPR2013-00517, Ex. 1026, Transcript, Jul. 15, 2014 Deposition of Kevin Burgess, Ph.D. (Redacted).
Ex, 1601, IPR2017-02174, Declaration of John D. Sutherland (IPR2017-02174) ("Sutherland Decl.").
Ex. 1602, IPR2017-02174, Curriculum Vitae of Dr. John D. Sutherland, filed Oct. 5, 2017.
Ex. 1605, IPR2017-02174, IPR2013-00266, Paper 73, Final Written Decision (Oct. 28, 2014).
Ex. 1606, IPR2017-02174, G.M. Church, WO 00/53812 A2 (Sep. 14, 2000) ("Church").
Ex. 1607, IPR2017-02174, Timothy M. Herman, U.S. Pat. No. 3,772,692 (Sep. 20, 1988) ("Herman").
Ex. 1608, IPR2017-02174, Ely Michael Rabani, WO 96/27025 AI (published Sep. 6, 1996) ("Rabani").
Ex. 1609, IPR2017-02174, Barbara A. Dawson et al., Affinity Isolation of Transcriptionally Active Murine Erythroleukemia Cell DNA using a Cleavable Biotinylated Nucleotide Analog, J. Biol. Chem. 264:12830-12837 (1989).
Ex. 1610, IPR2017-02174, S. W. Ruby et al., Affinity Chromatography with Biotinylated RNAs, Methods in Enzymol. 191:97-121 (1990).
EX. 1611, IPR2017-02174, Jeffrey Van Ness et al., U.S. Pat. No. 6,312,893 (Nov. 6, 2001) ("Van Ness").
Ex. 1612, IPR2017-02174, Mary Shimkus et al., A chemically cleavable biotinylated nucleotide: Usefulness in the recovery of protein-DNA complexes from avidin affinity columns, Proc. Natl. Acad. Sci. USA 82:2593-97 (1985) ("Shimkus").
Exhibit 2001 filed Jan. 23, 2018, IPR2017-02174, Eileen Zimmerman, Mar./Apr. 2014, The 50 Smartest Companies, MIT Tech Review, 117(2):Cover, 2, 4, 27-29.
Exhibit 2002 filed Jan. 23, 2018, IPR2017-02174, Goodwin, et al., 2016, Coming of age: ten years of next-generation sequencing technologies, Nature Reviews, 17:333-351.
Exhibit 2003 filed Jan. 23, 2018, IPR2017-02174, Complete Genomics, www.completegenomics.com, downloaded Jan. 15, 2018.
Exhibit 2004 filed Jan. 23, 2018, IPR2017-02174, Fehlmann et al., 2016, cPAS-based sequencing on the BGISEQ-500 to explore small non-coding RNAs, Clinical Epigenetics, 8:123.
Exhibit 2005 filed Jan. 23, 2018, IPR2017-02174, Julia Karow, Nov. 9, 2017. BGI's MGI tech launches new sequencing platforms, broadens scope with diagnostic ultrasound system. GenomeWeb.
Exhibit 2006 filed Jan. 23, 2018, IPR2017-02174, WO 00/53805, published Sep. 14, 2000, Stemple et al.
Exhibit 2007 filed Jan. 23, 2018, IPR2017-02174, WO 01/92284, published Dec. 6, 2001, Amershan Pharmacia Biotech UK Limited.
Exhibit 2008 filed Jan. 23, 2018, IPR2017-02174, U.S. Pat. No. 7,279,563, issued Oct. 9, 2007, Kwiatkowski.
Exhibit 2009 filed Jan. 23, 2018, IPR2017-02174, WO 96/023807, published Aug. 8, 1996, Kwiatkowski.
Exhibit 2010 filed Jan. 23, 2018, IPR2017-02174, WO 93/21340, published Oct. 28, 1993, Medical Research Council.
Exhibit 2011 filed Jan. 23, 2018, IPR2017-02174, WO 96/27025, published Sep. 6, 1996, Rabani.

Exhibit 2012 filed Jan. 23, 2018, IPR2017-02174, QIAGEN press release, QIAGEN agrees with BGI Tech to provide services based on the Human Gene Mutation Database (HGMD) in Greater China, https://corporate.qiagen.com/newsroom/press-releases/2017/20140729_bgi_hgmd, Jul. 29, 2014.
Exhibit 2013 filed Jan. 23, 2018, IPR2017-02174, QIAGEN press release, QIAGEN partners with world's largest sequencing provider, https://corporate.qiagen.com/newsroom/press-releases/2017/20150504_bgi_iva_partnership, May 4, 2015.
Exhibit 2018 filed Jan. 23, 2018, IPR2017-02174, May 6, 2010 IDS filed by CGI in U.S. Appl. No. 11/981,797.
Exhibit 2019 filed Jan. 23, 2018, IPR2017-02174, Oct. 7, 2010 IDS filed by CGI in U.S. Appl. No. 12/266,385.
Exhibit 2020 filed Jan. 23, 2018, IPR2017-02174, Aug. 30, 2010 IDS filed by CGI in U.S. Appl. No. 12/329,365.
Exhibit 2021 filed Jan. 23, 2018, IPR2017-02174, Aug. 10, 2016 IDS filed by CGI in U.S. Appl. No. 14/921,466.
Exhibit 2022 filed Jan. 23, 2018, IPR2017-02174, Peter G. M. Wuts, 2007, Preface to the Fourth Edition, in Greene's Protective Groups in Organic Synthesis, Greene & Wuts (Eds.), Hoboken, NJ: John Wiley & Sons.
Exhibit 2023 filed Jan. 23, 2018, IPR2017-02174, Excerpt from Branchaud Apr. 8, 2014 transcript in IPR2013-00517.
Exhibit 2024 filed Jan. 23, 2018, IPR2017-02174, Declaration of Floyd Romesberg, dated Jan. 22, 2018.
Exhibit 2025 filed Jan. 23, 2018, IPR2017-02174, Romesberg CV, updated Oct. 2017.
Exhibit 2026 filed Jan. 23, 2018, IPR2017-02174, , Suzuki et al., 1994, Mechanistic studies on depurination and apurinic site chain breakage in oligodeoxyribonucleotides, Nucleic Acids Research, 22(23):4997-5003.
Exhibit 2027 filed Jan. 23, 2018, IPR2017-02174, Treinin, 1971, General and theoretical aspects, in The Chemistry of the Azido Group, Saul Patai (Ed.), John Wiley & Sons, pp. 1-55.
Exhibit 2028 filed Jan. 23, 2018, IPR2017-02174, Excerpt fromRomesberg Jul. 8, 2014 transcript in IPR2013 00517.
Exhibit 2029 filed Jan. 23, 2018, IPR2017-02174, Wu et al., 2007, Termination of DNA synthesis by $N^6$-alkylated, not 3'-O-alkylated, photocleavable 2'-deoxyadenosine triphosphates, Nucleic Acids Research, 35(19):6339-6349.
Exhibit 2030 filed Jan. 23, 2018, IPR2017-02174, Boyer et al., 2001, Selective excision of AZTMP by drug-resistant human immunodeficiency virus reverse transcriptase, Journal of Virology, 75(10):4832-4842.
Exhibit 2031 filed Jan. 23, 2018, IPR2017-02174, IPR2013-00517, , Paper 64, submitted Sep. 2, 2014, IPR2013-00517, Illumina's Motion for Observations on the Cross-Examination Testimony of Bruce Branchaud, Ph.D. and Michael Metzker, Ph.D., 19 pages.
Exhibit 2033 filed Jan. 23, 2018, IPR2017-02174, Dantas et al., 1999, Stannous chloride mediates single strand breaks in plasmid DNA through reaactive oxygen species formation, Toxicology Letters, 110:129-136.
Exhibit 2035 filed Jan. 23, 2018, IPR2017-02174, Radom et al., 1971, Molecular orbital theory of the electronic structure of organic compounds. VIII. Geometries, energies, and polarities of $C_3$ hydrocarbons, J Am Chem Soc, 93(21):5339-5342.
Exhibit 2036 filed Jan. 23, 2018, IPR2017-02174, Nielsen et al., 1987, The vibrational spectra, molecular structure and conformation of organic azides. Part IV. An ab initio study of hydrazoic acid, azidomethane, azidoethane, azidoethene and azidomethanal, J. Molecular Structure, 150:361-379.
Exhibit 2037 filed Jan. 23, 2018, IPR2017-02174, Swarts et al., 1996, Effects of formic acid hydrolysis on the quantitative analysis of radiation-induced DNA base damage products assayed by gas chromatography/mass spectrometry, Radiat. Environ. Biophys, 35:41-53.
Exhibit 2038 filed Jan. 23, 2018, IPR2017-02174, Sutherland Declaration (Ex. 1101 in IPR2017-02172), dated Sep. 28, 2017.
Exhibit 2039 filed Feb. 14, 2018, IPR2017-02174, Declaration of Wm. Zimmerman in Support of Unopposed Pro Hac Vice Motion, dated Feb. 14, 2018.
Exhibit 1613 filed Feb. 28, 2018, IPR2017-02174, Illumina Press Release, dated Jan. 12, 2010.

(56) References Cited

OTHER PUBLICATIONS

Exhibit 1614 filed Feb. 28, 2018, IPR2017-02174, Declaration of Katie J.L. Scott in Support of Petitioner's Motion for Admission Pro Hac Vice, dated Feb. 28, 2019.
Paper 6 filed Jan. 23, 2018, IPR2017-02174, Illumina Patent Owner Preliminary Response.
Paper 7 filed Jan. 23, 2018, IPR2017-02174, Illumina Exhibit List.
Paper 8 filed Feb. 14, 2018, IPR2017-02174, Illumina Unopposed Motion for William Zimmerman to Appear Pro Hac Vice.
Paper 9 filed Feb. 14, 2018, IPR2017-02174, Illumina Supplemental POA for Wm. Zimmerman.
Paper 10 filed Feb. 14, 2018, IPR2017-02174, Illumina Updated Exhibit List.
Paper 13 filed Feb. 28, 2018, IPR2017-02174, Order—Conduct of the Proceeding.
Paper 14 filed Feb. 28, 2018, IPR2017-02174, CGI's Reply to Patent Owner's Preliminary Response.
Paper 15 filed Feb. 28, 2018, IPR2017-02174, Petitioner's Unopposed Motion for Admission of Katie J.L. Scott Pro Hac Vice.
Paper 16 filed Feb. 28, 2018, IPR2017-02174, Petitioner's Updated Exhibit List.
Paper 17 filed Mar. 5, 2018, IPR2017-02174, Illumina's Sur-Reply to Petitioner's Reply to Preliminary Response.
Decision Denying Institution of Inter Partes Review in IPR2017-02174, U.S. Pat. No. 7,566,537 B2, dated Apr. 20, 2018.
Petition for Inter Partes Review of U.S. Pat. No. 9,868,985, Case No. IPR2018-00797, filed Mar. 16, 2018.
Ex. 1001 in IPR2018-00797 filed Mar. 16, 2018, U.S. Pat. No. 9,718,852 ("Ju") issued Aug. 1, 2017.
Ex. 1002 in IPR2017-00797 filed Mar. 16, 2018, U.S. Pat. No. 9,708,358 ("Ju") issued Jul. 18, 2017.
Ex. 1003 in IPR2017-00797 filed Mar. 16, 2018, U.S. Pat. No. 9,719,139 ("Ju") issued Jul. 18, 2017.
Ex. 1004 in IPR2017-00797 filed Mar. 16, 2018, U.S. Pat. No. 9,725,480 ("Ju") issued Aug. 8, 2017.
Ex. 1005 in IPR2017-00797 filed Mar. 16, 2018, Mar. 6, 2014 IPR2012-00007, Paper 140, Final Written Decision.
Ex. 1006 in IPR2017-00797 filed Mar. 16, 2018, Mar. 6, 2014 IPR2012-00006, Paper 128, Final Written Decision.
Ex. 1007 in IPR2017-00797 filed Mar. 16, 2018, Mar. 6, 2014 IPR2013-00011, Paper 130, Final Written Decision.
Ex. 1008 in IPR2017-00797 filed Mar. 16, 2018, Jul. 17, 2015 Federal Circuit Opinion Affirming IPR2012-00006, IPR2012-00007 and IPR2013-00011.
Ex. 1010 in IPR2017-00797 filed Mar. 16, 2018, U.S. Pat. No. 7,790,869 ("Ju") issued Sep. 7, 2010.
Ex. 1011 in IPR2017-00797 filed Mar. 16, 2018, Alberts, et al., "Molecular Biology of the Cell", Third Edition, Garland Publishing Inc., New York (1994).
Ex. 1013 in IPR2017-00797 filed Mar. 16, 2018, WO 91/06678 ("Tsien") published May 16, 1991.
Ex. 1014 in IPR2017-00797 filed Mar. 16, 2018, Prober, et al., "A System for Rapid DNA Sequencing with Flourescent Chain-Terminating Dideoxynucleotides", Science, 238:336-341 (1987) ("Prober").
Ex. 1015 in IPR2017-00797 filed Mar. 16, 2018, U.S. Pat. No. 5,547,839 ("Dower") issued Aug. 20, 1996.
Ex. 1016 in IPR2017-00797 filed Mar. 16, 2018, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2017-00797 filed Mar. 16, 2018, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2017-00797 filed Mar. 16, 2018, Sanger et al., "DNA sequencing with chain-terminating inhibitors", Proc. Natl. Acad. Sci. USA, 74:5463-5467 (1977) ("Sanger").
Ex. 1019 in IPR2017-00797 filed Mar. 16, 2018, U.S. Pat. No. 7,270,951 ("Stemple") issued Sep. 18, 2017.
Ex. 1020 in IPR2017-00797 filed Mar. 16, 2018, U.S. Pat. No. 5,302,509 ("Cheeseman"), issued Apr. 12, 1994.
Ex. 1021 in IPR2017-00797 filed Mar. 16, 2018, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2017-00797 filed Mar. 16, 2018, Welch, et al., "Syntheses of Nucleosides Designed for Combinatorial DNA Sequencing", Chem. Eur. J., 5:951-960 (1999) ("Welch").
Ex. 1024 in IPR2017-00797 filed Mar. 16, 2018, Welch, et al., "Corrgenda—Syntheses of Nucleosides Designed for Combinatorial DNA Sequencing", Chem. Eur. J., 11:7136-7145 (2005) ("Welch Corrigenda").
Ex. 1025 in IPR2017-00797 filed Mar. 16, 2018, Seela, et al., "7-Deazapurine containing DNA", Nucleic Acids Research, 20:55-61 (1991) ("Seela 1991").
Ex. 1026 in IPR2017-00797 filed Mar. 16, 2018, U.S. Pat. No. 4,804,748 ("Seela Patent"), issued Feb. 14, 1989.
Ex. 1027 in IPR2017-00797 filed Mar. 16, 2018, Rosenblum, et al., "New dye-labeled terminators for improved DNA sequencing patterns", Nucleic Acid Research, 25:4500-4504 (1997) ("Rosenblum").
Ex. 1028 in IPR2017-00797 filed Mar. 16, 2018, Excerpts from Sep. 4, 2013 Deposition Transcript of Dr. George L. Trainor in IPR2012-00007.
Ex. 1029 in IPR2017-00797 filed Mar. 16, 2018, U.S. Pat. No. 5,151,507 ("Hobbs") issued Sep. 29, 1992.
Ex. 1030 in IPR2017-00797 filed Mar. 16, 2018, Ramzaeva, et al., "88. 7-Substituted 7-Deasa-2'-deoxyguanosines: Regioselective Halogenation of Pyrrolo[2,3-d] pyrimidine Nucleosides", Helvetica Chimica Acta, 78:1083-1090 (1995) ("Ramzaeva 1995").
Ex. 1031 in IPR2017-00797 filed Mar. 16, 2018, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1032 in IPR2017-00797 filed Mar. 16, 2018, Seela, et al., "Duplex Stability of Oligonucleotides Containing 7-Substituted 7-Deaza- and 8-Aza-7-Deazapurine Nucleosides", Nucleosides, Nucleosides & Nucleotides, 16:963-966 (1997) ("Seela 1997").
Ex. 1033 in IPR2017-00797 filed Mar. 16, 2018, Ramzaeva, et al., "123. 7-Deazaguanine DNA: Oligonucleotides with Hydrophobic or Cationic Side Chains", Helvetica Chimica Acta, 80:1809-1822 (1997) ("Ramzaeva 1997").
Ex. 1034 in IPR2017-00797 filed Mar. 16, 2018, Jun. 25, 2013 Declaration of Dr. George L. Trainor from IPR2012-00006.
Ex. 1035 in IPR2017-00797 filed Mar. 16, 2018, Boss, et al., "Cleavage of Allyl Ethers with Pd/C", Angew. Chem. Int. Ed. Engl., 15:558-559 (1976) ("Boss").
Ex. 1036 in IPR2017-00797 filed Mar. 16, 2018, Qian, et al., "Unexpected Enzymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998) ("Qian").
Ex. 1037 in IPR2017-00797 filed Mar. 16, 2018, Kamal, et al., "A Mild and Rapid Regeneration of Alcohols from their Allylic Ethers by Chlorotrimethylsilane/Sodium Iodide", Tetrahedron Letters, 40:371-372 (1999) ("Kamal").
Ex. 1039 in IPR2017-00797 filed Mar. 16, 2018, Vollhardt, et al., "Organic Chemistry", Second Edition, W.H. Freeman and Co., New York (1994) ("Vollhardt").
Ex. 1040 in IPR2017-00797 filed Mar. 16, 2018, Yu, et al., "Cyanine dye dUTP analogs for enzymatic labeling of DNA probes", Nucleic Acids Research, 22:3226-3232 (1994) ("Yu").
Ex. 1041 in IPR2017-00797 filed Mar. 16, 2018, Livak, et al., "Detection of single base differences using biotinylated nucleotides with very long linker arms", Nucleic Acids Research, 20:4831-4837 (1992) ("Livak").
Ex. 1042 in IPR2017-00797 filed Mar. 16, 2018, Watson, et al., "Genetical Implication of the Structure of Deoxyribonucleic Acid", Nature, 171:964-967 (1953) ("Watson & Crick").
Ex. 1043 in IPR2017-00797 filed Mar. 16, 2018, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").

(56) References Cited

OTHER PUBLICATIONS

Ex. 1044 in IPR2017-00797 filed Mar. 16, 2018, Feb. 11, 2015 Final Written Decision in IPR2013-00517.
Ex. 1045 in IPR2017-00797 filed Mar. 16, 2018, May 9, 2016 Federal Circuit Opinion Affirming IPR2013-00517.
Ex. 1046 in IPR2017-00797 filed Mar. 16, 2018, Gigg, et al., "The Allyl Ether as a Protecting Group in Carbohydrate Chemistry Part II", J. Chem. Soc. (C), 1903-1911 (1968) ("Gigg").
Ex. 1047 in IPR2017-00797 filed Mar. 16, 2018, Aug. 30, 2013 Substitute Columbia Patent Owner Response in IPR2012-00007, Paper 77.
Ex. 1048 in IPR2017-00797 filed Mar. 16, 2018, Jul. 25, 2014 Final Written Decision in IPR2013-00128, Paper 92.
Ex. 1049 in IPR2017-00797 filed Mar. 16, 2018, Oct. 28, 2014 Final Written Decision in IPR2013-00266, Paper 73.
Ex. 1050 in IPR2017-00797 filed Mar. 16, 2018, Jan. 29, 2016 Federal Circuit Opinion Affirming IPR2013-00128 and IPR2013-00266.
Ex. 1051 in IPR2017-00797 filed Mar. 16, 2018, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2017-00797 filed Mar. 16, 2018, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2017-00797 filed Mar. 16, 2018, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2017-00797 filed Mar. 16, 2018, U.S. Pat. No. 8,088,575 ("Ju"), issued Jan. 3, 2012.
Ex. 1055 in IPR2017-00797 filed Mar. 16, 2018, Stryer, "Biochemistry", Fourth Edition, W.H. Freeman and Co., New York (1995) ("Stryer").
Ex. 1057 in IPR2017-00797 filed Mar. 16, 2018, Curriculum Vitae of Floyd Romesberg, Ph.D. dated Oct. 2017.
Ex. 1059 in IPR2017-00797 filed Mar. 16, 2018, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1068 in IPR2017-00797 filed Mar. 16, 2018, Excerpts from Prosecution History of U.S. Pat. No. 9,725,480 ("Ju") issued Aug. 8, 2017.
Ex. 1072 in IPR2017-00797 filed Mar. 16, 2018, Excerpts from Prosecution History of U.S. Pat. No. 9,718,852 ("Ju") issued Aug. 1, 2017.
Ex. 1073 in IPR2017-00797 filed Mar. 16, 2018, Excerpts from Prosecution History of U.S. Pat. No. 9,719,139 ("Ju") issued Jul. 18, 2017.
Ex. 1074 in IPR2017-00797 filed Mar. 16, 2018, Excerpts from Prosecution History of U.S. Pat. No. 9,708,358 ("Ju") issued Jul. 18, 2017.
Ex. 1075 in IPR2017-00797 filed Mar. 16, 2018, U.S. Pat. No. 9,868,985 ("Ju") issued Jan. 16, 2018.
Ex. 1076 in IPR2017-00797 filed Mar. 16, 2018, Excerpts from Prosecution History of U.S. Pat. No. 9,868,985, issued Jan. 16, 2018.
Ex. 1077 in IPR2017-00797 filed Mar. 16, 2018, Declaration of Jingyue Ju from Prosecution History of U.S. Pat. No. 9,868,985, dated Oct. 11, 2017.
Ex. 1078 in IPR2017-00797 filed Mar. 16, 2018, Declaration of Floyd Romesberg, Ph.D. For '985, dated Mar. 16, 2018.
Ex. 1079 in IPR2017-00797 filed Mar. 16, 2018, List of documents considered by Floyd Romesberg, Ph.D.
Ex. 1080 in IPR2017-00797 filed Mar. 16, 2018, WO 98/53300 ("Pallas") published Nov. 26, 1998.
Ex. 1081 in IPR2017-00797 filed Mar. 16, 2018, U.S. Pat. No. 7,713,698 ("Ju") issued May 11, 2010.
Ex. 1082 in IPR2017-00797 filed Mar. 16, 2018, U.S. Pat. No. 6,432,360 ("Church") issued Aug. 13, 2002.
Ex. 1083 in IPR2017-00797 filed Mar. 16, 2018, WO 98/33939 ("Anazawa") (in Japanese) published Aug. 6, 1998.
Ex. 1084 in IPR2017-00797 filed Mar. 16, 2018, English translation of Anazawa with affidavit, dated Sep. 12, 2012.
Ex. 1085 in IPR2017-0079 filed Mar. 16, 20187, U.S. Pat. No. 5,424,186 ("Fodor") issued Jun. 13, 1995.
Ex. 1086 in IPR2017-00797 filed Mar. 16, 2018, Columbia's Third Amended Complaint for Patent Infringement, CA 17-973 (GMS) USDC, District of Delaware, dated Feb. 12, 2018.
Exhibit 2001 in IPR2017-00797 filed Apr. 17, 2018, Declaration of Robert S. Schwartz, dated Apr. 13, 2018.
Paper 3 in IPR2017-00797 filed Apr. 4, 2018, Patent Owner's Mandatory Notices Pursuant to 37 CFR 42.8.
Paper 4 in IPR2017-00797 filed Apr. 6, 2018, Notice of Accord Filing Date.
Paper 6 in IPR2017-00797 filed Apr. 17, 2018, Columbia's Exhibit List No. 1 Under 37 CFR 42.63(e).
Petition for Inter Partes Review of U.S. Pat. No. 9,718,852, Case No. IPR2018-00291 filed Dec. 8, 2017.
Ex. 1001 in IPR2018-00291 filed Dec. 8, 2017, U.S. Pat. No. 9,718,852 ("Ju") issued Aug. 1, 2017.
Ex. 1002 in IPR2018-00291 filed Dec. 8, 2017, U.S. Pat. No. 9,708,358 ("Ju") issued Jul. 18, 2017.
Ex. 1003 in IPR2018-00291 filed Dec. 8, 2017, U.S. Pat. No. 9,719,139 ("Ju") issued Jul. 18, 2017.
Ex. 1004 in IPR2018-00291 filed Dec. 8, 2017, U.S. Pat. No. 9,725,480 ("Ju") issued Aug. 8, 2017.
Ex. 1005 in IPR2018-00291 filed Dec. 8, 2017, Mar. 6, 2014 IPR2012-00007, Paper 140, Final Written Decision.
Ex. 1006 in IPR2018-00291 filed Dec. 8, 2017, Mar. 6, 2014 IPR2012-00006, Paper 128, Final Written Decision.
Ex. 1007 in IPR2018-00291 filed Dec. 8, 2017, Mar. 6, 2014 IPR2013-00011, Paper 130, Final Written Decision.
Ex. 1008 in IPR2018-00291 filed Dec. 8, 2017, Jul. 17, 2015 Federal Circuit Opinion Affirming IPR2012-00006, IPR2012-00007 and IPR2013-00011.
Ex. 1009 in IPR2018-00291 filed Dec. 8, 2017, Excerpts from Prosecution History of U.S. Pat. No. 9,718,852 ("Ju") issued Aug. 1, 2017.
Ex. 1010 in IPR2018-00291 filed Dec. 8, 2017, U.S. Pat. No. 7,790,869 ("Ju") issued Sep. 7, 2010.
Ex. 1011 in IPR2018-00291 filed Dec. 8, 2017, Alberts, et al., "Molecular Biology of the Cell", Third Edition, Garland Publishing Inc., New York (1994).
Ex. 1012 in IPR2018-00291 filed Dec. 8, 2017, Declaration of Floyd Romesberg, Ph.D., dated Dec. 8, 2017.
Ex. 1013 in IPR2018-00291 filed Dec. 8, 2017, WO 91/06678 ("Tsien") published May 16, 1991.
Ex. 1014 in IPR2018-00291 filed Dec. 8, 2017, Prober, et al., "A System for Rapid DNA Sequencing with Flourescent Chain-Terminating Dideoxynucleotides", Science, 238:336-341 (1987) ("Prober").
Ex. 1015 in IPR2018-00291 filed Dec. 8, 2017, U.S. Pat. No. 5,547,839 ("Dower") Aug. 20, 1996.
Ex. 1016 in IPR2018-00291 filed Dec. 8, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00291 filed Dec. 8, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2018-00291 filed Dec. 8, 2017, Sanger et. al., "DNA sequencing with chain-terminating inhibitors", Proc. Natl. Acad. Sci. USA, 74:5463-5467 (1977) ("Sanger").
Ex. 1019 in IPR2018-00291 filed Dec. 8, 2017, U.S. Pat. No. 7,270,951 ("Stemple") issued Sep. 18, 2017.
Ex. 1020 in IPR2018-00291 filed Dec. 8, 2017, U.S. Pat. No. 5,302,509 ("Cheeseman") issued Apr. 12, 1994.

(56) References Cited

OTHER PUBLICATIONS

Ex. 1021 in IPR2018-00291 filed Dec. 8, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1022 in IPR2018-00291 filed Dec. 8, 2017, Declaration of Jingyue Ju from Prosecution History of U.S. Pat. No. 9,718,852 ("Ju") dated May 2, 2017.
Ex. 1023 in IPR2018-00291 filed Dec. 8, 2017, Welch, et al., "Syntheses of Nucleosides Designed for Combinatorial DNA Sequencing", Chem. Eur. J., 5:951-960 (1999) ("Welch").
Ex. 1024 in IPR2018-00291 filed Dec. 8, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1025 in IPR2018-00291 filed Dec. 8, 2017, Seela, et al., "7-Deazapurine containing DNA", Nucleic Acids Research, 20:55-61 (1991) ("Seela 1991").
Ex. 1026 in IPR2018-00291 filed Dec. 8, 2017, U.S. Pat. No. 4,804,748 ("Seela Patent") issued Feb. 14, 1989.
Ex. 1027 in IPR2018-00291 filed Dec. 8, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00291 filed Dec. 8, 2017, Excerpts from Sep. 4, 2013 Deposition Transcript of Dr. George L. Trainor in IPR2012-00007.
Ex. 1029 in IPR2018-00291 filed Dec. 8, 2017, U.S. Pat. No. 5,151,507 ("Hobbs") issued Sep. 29, 1992.
Ex. 1030 in IPR2018-00291 filed Dec. 8, 2017, Ramzaeva, et al., "88. 7-Substituted 7-Deasa-2'-deoxyguanosines: Regioselective Halogenation of Pyrrolo[2,3-d]pyrimidine Nucleosides", Helvetica Chimica Acta, 78:1083-1090 (1995) ("Ramzaeva 1995").
Ex. 1031 in IPR2018-00291 filed Dec. 8, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1032 in IPR2018-00291 filed Dec. 8, 2017, Seela, et al., "Duplex Stability of Oligonucleotides Containing 7-Substituted 7-Deaza- and 8-Aza-7-Deazapurine Nucleosides", Nucleosides, Nucleosides & Nucleotides, 16:963-966 (1997) ("Seela 1997").
Ex. 1033 in IPR2018-00291 filed Dec. 8, 2017, Ramzaeva, et al., "123. 7-Deazaguanine DNA: Oligonucleotides with Hydrophobic or Cationic Side Chains", Helvetica Chimica Acta, 80:1809-1822 (1997) ("Ramzaeva 1997").
Ex. 1034 in IPR2018-00291 filed Dec. 8, 2017, Jun. 25, 2013 Declaration of Dr. George L. Trainor from IPR2012-00006.
Ex. 1035 in IPR2018-00291 filed Dec. 8, 2017, Boss, et al., "Cleavage of Allyl Ethers with Pd/C", Angew. Chem. Int. Ed. Engl., 15:558-559 (1976) ("Boss").
Ex. 1036 in IPR2018-00291 filed Dec. 8, 2017, Qian, et al., "Unexpected Ensymatic Fucosylation of the Hindered Tertiary Alcohol of 3-C-Methyl-N-Acetyllactosamine Produces a Novel Analogue of the LeX-Trisaccharide", *Journal* of the American Chemical Society, 120:2184-2185 (1998) ("Qian").
Ex. 1037 in IPR2018-00291 filed Dec. 8, 2017, Kamal, et al., "A Miled and Rapid Regeneration of Alcohols from their Allylic Ethers by Chlorotrimethylsilane/Sodium Iodide", Tetrahedron Letters, 40:371-372 (1999) ("Kamal").
Ex. 1038 in IPR2018-00291 filed Dec. 8, 2017, Excerpts from Prosecution History of U.S. Pat. No. 9,725,480 ("Ju") issued Aug. 8, 2017.
Ex. 1039 in IPR2018-00291 filed Dec. 8, 2017, Vollhardt, et al., "Organic Chemistry", Second Edition, W.H. Freeman and Co., New York (1994) ("Vollhardt").
Ex. 1040 in IPR2018-00291 filed Dec. 8, 2017, Yu, et al., "Cyanine dye dUTP analogs for enzymatic labeling of DNA probes", Nucleic Acids Research, 22:3226-3232 (1994) ("Yu").

Ex. 1041 in IPR2018-00291 filed Dec. 8, 2017, Livak, et al., "Detection of single base differences using biotinylated nucleotides with very long linker arms", Nucleic Acids Research, 20:4831-4837 (1992) ("Livak").
Ex. 1042 in IPR2018-00291 filed Dec. 8, 2017, Watson, et al., "Genetical Implication of the Structure of Deoxyribonucleic Acid", Nature, 171:964-967 (1953) ("Watson & Crick").
Ex. 1043 in IPR2018-00291 filed Dec. 8, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00291 filed Dec. 8, 2017, Feb. 11, 2015 Final Written Decision in IPR2013-00517.
Ex. 1045 in IPR2018-00291 filed Dec. 8, 2017, May 9, 2016 Federal Circuit Opinion Affirming IPR2013-00517.
Ex. 1046 in IPR2018-00291 filed Dec. 8, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00291 filed Dec. 8, 2017, Aug. 30, 2013 Substitute Columbia Patent Owner Response in IPR2012-00007, Paper 77.
Ex. 1048 in IPR2018-00291 filed Dec. 8, 2017, Jul. 25, 2014 Final Written Decision in IPR2013-00128, Paper 92.
Ex. 1049 in IPR2018-00291 filed Dec. 8, 2017, Oct. 28, 2014 Final Written Decision in IPR2013-00266, Paper 73.
Ex. 1050 in IPR2018-00291 filed Dec. 8, 2017, Jan. 29, 2016 Federal Circuit Opinion Affirming IPR2013-00128 and IPR2013-00266.
Ex. 1051 in IPR2018-00291 filed Dec. 8, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00291 filed Dec. 8, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00291 filed Dec. 8, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00291 filed Dec. 8, 2017, U.S. Pat. No. 8,088,575 ("Ju"), issued Jan. 3, 2012.
Ex. 1055 in IPR2018-00291 filed Dec. 8, 2017, Stryer, "Biochemistry", Fourth Edition, W.H. Freeman and Co., New York (1995) ("Stryer").
Ex. 1056 in IPR2018-00291 filed Dec. 8, 2017, Columbia's Amended Complaint for Patent Infringement, C.A. No. 17-973 (GMS) , USDC, District of Delaware, dated Aug. 1, 2017.
Ex. 1057 in IPR2018-00291 filed Dec. 8, 2017, Curriculum Vitae of Floyd Romesberg, Ph.D. dated Oct. 2017.
Ex. 1058 in IPR2018-00291 filed Dec. 8, 2017, List of documents considered by Floyd Romesberg, Ph.D.
Ex. 1059 in IPR2018-00291 filed Dec. 8, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Exhibit 2002 in IPR2018-00291 filed Mar. 27, 2018, U.S. Pat. No. 7,790,869, Ju, issued Sep. 7, 2010.
Exhibit 2003 in IPR2018-00291 filed Mar. 27, 2018, U.S. Pat. No. 7,713,698, Ju, issued May 11, 2010.
Exhibit 2004 in IPR2018-00291 filed Mar. 27, 2018, U.S. Pat. No. 8,088,575, Ju, issued Jan. 3, 2012.
Exhibit 2005 in IPR2018-00291 filed Mar. 27, 2018, Excerpts from the Prosecution History of U.S. Pat. No. 9,718,852, issued Aug. 1, 2017.
Exhibit 2006 in IPR2018-00291 filed Mar. 27, 2018, Excerpts from the Prosecution History of U.S. Pat. No. 9,725,480, issued Aug. 8, 2017.
Exhibit 2007 in IPR2018-00291 filed Mar. 27, 2018, IPR2013-00517, Ex. 2011, Declaration of Floyd Romesberg, Ph.D. (May 5, 2014).

(56) References Cited

OTHER PUBLICATIONS

Exhibit 2008 in IPR2018-00291 filed Mar. 27, 2018, IPR2013-00517, Paper 32, Illumina's Patent Owner Response (May 5, 2014).
Exhibit 2009 in IPR2018-00291 filed Mar. 27, 2018, Excerpts from the Ex Parte Reexamination History of U.S. Pat. No. 5,808,045.
Exhibit 2011 in IPR2018-00291 filed Mar. 27, 2018, PCT Publication WO 98/33939 ("Anazawa") publisyhed Aug. 6, 1989, (English translation).
Exhibit 2012 in IPR2018-00291 filed Mar. 27, 2018, Metzker, et al., Elimination of Residual Natural Nucleotides from 3'-O-Modified-dNTP Syntheses by Enzymatic Mop-Up, BioTechniques, 25:814-817 (1998).
Exhibit 2013 in IPR2018-00291 filed Mar. 27, 2018, PCT Publication WO 00/53805 ("Stemple") dated Sep. 14, 2000.
Exhibit 2014 in IPR2018-00291 filed Mar. 27, 2018, Metzker, et al., Stop-Start DNA Synthesis in the Base Addition Sequencing Scheme (BASS), Genome Mapping & Sequencing (1994).
Exhibit 2015 in IPR2018-00291 filed Mar. 27, 2018, U.S. Pat. No. 7,541,444, Milton, issued Jun. 2, 2009.
Exhibit 2016 in IPR2018-00291 filed Mar. 27, 2018, U.S. Pat. No. 7,771,973, Milton, issued Aug. 10, 2010.
Exhibit 2017 in IPR2018-00291 filed Mar. 27, 2018, U.S. Patent Application Publication No. 2007/0166705 (Milton) published Jul. 19, 2007.
Exhibit 2018 in IPR2018-00291 filed Mar. 27, 2018, Boons, et al. (1996) A new procedure for the isomerization of substituted and unsubstituted allyl ethers of carbohydrates, Chem. Commun., pp. 141-142.
Exhibit 2019 in IPR2018-00291 filed Mar. 27, 2018, Ochiai, et al. (1996) Hypervalent (tert-Butylperoxy)iodanes generate iodine-centered radicals at room temperature in solution: oxidation and deprotection of benzyl and allyl ethers, and evidence for generation of α-oxy carbon radicals, J. am. Chem. Soc., 118:7716-7730.
Exhibit 2020 in IPR2018-00291 filed Mar. 27, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00291 filed Mar. 27, 2018, U.S. Pat. No. 6,232,465, Hiatt, issued May 15, 2001.
Exhibit 2022 in IPR2018-00291 filed Mar. 27, 2018, Excerpts from the Ex Parte Reexamination History of U.S. Pat. No. 6,232,465.
Exhibit 2023 in IPR2018-00291 filed Mar. 27, 2018, Solexa, Inc. Fed. R. Civ. P. 7.1 Statement (Feb. 19, 2010).
Exhibit 2024 in IPR2018-00291 filed Mar. 27, 2018, Solexa, Inc. Schedule 13D-A Submission to the United States Securities and Exchange Commission (Feb. 2, 2007).
Exhibit 2025 in IPR2018-00322 filed Apr. 9, 2018, Litosh, et al. (2011) Improved nucleotide selectivity and termination of 3'-OH unblocked reversible terminators by molecular tuning of 2-nitrobenzyl alkylated HOMedU triphosphates, Nucleic Acids Research 39(6):e39.
Exhibit 2026 in IPR2018-00291 filed Mar. 27, 2018, IPR2017-02172, Paper 6, Preliminary Response of Patent Owner Illumine Cambridge Ltd. (Jan. 23, 2018).
Exhibit 2027 in IPR2018-00291 filed Mar. 27, 2018, IPR2017-02174, Paper 6, Preliminary Response of Patent Owner Illumina Cambridge Ltd. (Jan. 23, 2018).
Exhibit 2028 in IPR2018-00291 filed Mar. 27, 2018, U.S. Pat. No. 7,566,537 (Balasubramanian) issued Jul. 28, 2009.
Exhibit 2029 in IPR2018-00291 filed Mar. 27, 2018, No. 2015-1123 (CAFC), Brief of Patent Owner-Appellant Illumina Cambridge Ltd., D.I. 27 (Mar. 10, 2015).
Exhibit 2030 in IPR2018-00291 filed Mar. 27, 2018, IPR2013-00266, Paper 39, Patent Owner Illumina Reply to Petitioner Opposition to Illumina Motion to Amend (Mar. 21, 2014).
Exhibit 2031 in IPR2018-00322 filed Apr. 9, 2018, Canard & Sarfati (1994) DNA polymerase fluorescent substrates with reversible 3'-tags, Gene, 148:1-6.
Exhibit 2032 in IPR2018-00322 filed Apr. 9, 2018, IPR2013-00517, Paper 84, Oral Hearing Transcript (Feb. 2, 2015).

Exhibit 2033 in IPR2018-00291 filed Mar. 27, 2018, IPR2013-00517, Paper 64, Illumine Motion for Observations on the Cross-Examination Testimony of Bruce Branchaud, Ph.D. and Michael Metzker, Ph.D. (Sep. 2, 2014).
Exhibit 2034 in IPR2018-00291 filed Mar. 27, 2018, IPR2012-00007, Paper 5, Petition for Inter Partes Review of U.S. Pat. No. 7,790,869 (Sep. 16, 2012).
Exhibit 2035 in IPR2018-00291 filed Mar. 27, 2018, IPR2013-00517, Exhibit 1025, Deposition of Floyd Romesberg, Ph.D. (Jul. 28, 2014).
Exhibit 2036 in IPR2018-00291 filed Mar. 27, 2018, IPR2012-00007, Paper 38, Decision on Petition for Inter Partes Review (Mar. 12, 2013).
Exhibit 2039 in IPR2018-00291 filed Mar. 27, 2018, PCT Publication WO 98/33939 (Anazawa) published Aug. 6, 1998.
Exhibit 2040 in IPR2018-00291 filed Mar. 27, 2018, Translation Affidavit for Anazawa, dated Sep. 12, 2012.
Exhibit 2041 in IPR2018-00291 filed Mar. 27, 2018, Welch & Burgess (1999) Synthesis of Fluorescent, photolabile 3'-0-protected nucleoside triphosphates for the base addition sequencing scheme, Nucleosides & Nucleotides, 18(2):197-201.
Exhibit 2042 in IPR2018-00291 filed Mar. 27, 2018, IPR2013-00517, Paper 68, Illumina Opposition to IBS Motion to Exclude Evidence.
Exhibit 2043 in IPR2018-00291 filed Mar. 27, 2018, Excerpts from the Prosecution History of U.S. Pat. No. 7,771,973.
Paper 3 in IPR2018-00291 filed Mar. 27, 2018, Notice of Accord Filing Date, filed Dec. 27, 2017.
Paper 4 in IPR2018-00291 filed Dec. 28, 2017, Patent Owner's Mandatory Notices Pursuant to 37 C.F.R. 42.8.
Paper 5 in IPR2018-00291 filed Jan. 3, 2018, Illumina's Supplemental Mandatory Notice—Related Matters.
Paper 7 in IPR2018-00291 filed Jan. 9, 2018, Columbia's Exhibit List No. 1 Under 37 CFR 42.63(e).
Paper 8 in IPR2018-00291 filed Mar. 27, 2018, Patent Owner Preliminary Response.
Paper 9 in IPR2018-00291 filed Mar. 27, 2018, Illumina's Supplemental Mandatory Notice, filed Apr. 6, 2018.
Petition for Inter Partes Review of U.S. Pat. No. 9,719,139, Case No. IPR2018-00318.
Ex. 1003 in IPR2018-00318 filed Dec. 15, 2017, U.S. Pat. No. 9,719,139 ("Ju") issued Jul. 18, 2017.
Ex. 1005 in IPR2018-00318 filed Dec. 15, 2017, Mar. 6, 2014 IPR2012-00007, Paper 140, Final Written Decision.
Ex. 1006 in IPR2018-00318 filed Dec. 15, 2017, Mar. 6, 2014 IPR2012-00006, Paper 128, Final Written Decision.
Ex. 1007 in IPR2018-00318 filed Dec. 15, 2017, Mar. 6, 2014 IPR2013-00011, Paper 130, Final Written Decision.
Ex. 1008 in IPR2018-00318 filed Dec. 15, 2017, Jul. 17, 2015 Federal Circuit Opinion Affirming IPR2012-00006, IPR2012-00007 and IPR2013-00011.
Ex. 1010 in IPR2018-00318 filed Dec. 15, 2017, U.S. Pat. No. 7,790,869 ("Ju") issued Sep. 7, 2010.
Ex. 1011 in IPR2018-00318 filed Dec. 15, 2017, Alberts, et al., "Molecular Biology of the Cell", Third Edition, Garland Publishing Inc., New York (1994).
Ex. 1013 in IPR2018-00318 filed Dec. 15, 2017, WO 91/06678 ("Tsien") published May 16, 1991.
Ex. 1014 in IPR2018-00318 filed Dec. 15, 2017, Prober, et al., "A System for Rapid DNA Sequencing with Flourescent Chain-Terminating Dideoxynucleotides", Science, 238:336-341 (1987) ("Prober").
Ex. 1015 in IPR2018-00318 filed Dec. 15, 2017, U.S. Pat. No. 5,547,839 ("Dower") issued Aug. 20, 1996.
Ex. 1016 in IPR2018-00318 filed Dec. 15, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00318 filed Dec. 15, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").

(56) References Cited

OTHER PUBLICATIONS

Ex. 1018 in IPR2018-00318 filed Dec. 15, 2017, Sanger et. al., "DNA sequencing with chain-terminating inhibitors", Proc. Natl. Acad. Sci. USA, 74:5463-5467 (1977) ("Sanger").
Ex. 1019 in IPR2018-00318 filed Dec. 15, 2017, U.S. Pat. No. 7,270,951 ("Stemple") issued Sep. 18, 2017.
Ex. 1020 in IPR2018-00318 filed Dec. 15, 2017, U.S. Pat. No. 5,302,509 ("Cheeseman") issued Apr. 12, 1994.
Ex. 1021 in IPR2018-00318 filed Dec. 15, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2018-00318 filed Dec. 15, 2017, Welch, et al., "Syntheses of Nucleosides Designed for Combinatorial DNA Sequencing", Chem. Eur. J., 5:951-960 (1999) ("Welch").
Ex. 1024 in IPR2018-00318 filed Dec. 15, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1027 in IPR2018-00318 filed Dec. 15, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00318 filed Dec. 15, 2017, Excerpts from Sep. 4, 2013 Deposition Transcript of Dr. George L. Trainor in IPR2012-00007.
Ex. 1029 in IPR2018-00318 filed Dec. 15, 2017, U.S. Pat. No. 5,151,507 ("Hobbs") issued Sep. 29, 1992.
Ex. 1031 in IPR2018-00318 filed Dec. 15, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1034 in IPR2018-00318 filed Dec. 15, 2017, Jun. 25, 2013 Declaration of Dr. George L. Trainor from IPR2012-00006.
Ex. 1035 in IPR2018-00318 filed Dec. 15, 2017, Boss, et al., "Cleavage of Allyl Ethers with Pd/C", Angew. Chem. Int. Ed. Engl., 15:558-559 (1976) ("Boss").
Ex. 1036 in IPR2018-00318 filed Dec. 15, 2017, Qian, et al., "Unexpected Ensymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998) ("Qian").
Ex. 1037 in IPR2018-00318 filed Dec. 15, 2017, Kamal, et al., "A Miled and Rapid Regeneration of Alcohols from their Allylic Ethers by Chlorotrimethylsilane/Sodium Iodide", Tetrahedron Letters, 40:371-372 (1999) ("Kamal").
Ex. 1038 in IPR2018-00318 filed Dec. 15, 2017, Excerpts from Prosecution Historyof U.S. Pat. No. 9,725,480 ("Ju").
Ex. 1039 in IPR2018-00318 filed Dec. 15, 2017, Vollhardt, et al., "Organic Chemistry", Second Edition, W.H. Freeman and Co., New York (1994) ("Vollhardt").
Ex. 1040 in IPR2018-00318 filed Dec. 15, 2017, Yu, et al., "Cyanine dye dUTP analogs for enzymatic labeling of DNA probes", Nucleic Acids Research, 22:3226-3232 (1994) ("Yu").
Ex. 1041 in IPR2018-00318 filed Dec. 15, 2017, Livak, et al., "Detection of single base differences using biotinylated nucleotides with very long linker arms", Nucleic Acids Research, 20:4831-4837 (1992) ("Livak").
Ex. 1042 in IPR2018-00318 filed Dec. 15, 2017, Watson, et al., "Genetical Implication of the Structure of Deoxyribonucleic Acid", Nature, 171:964-967 (1953) ("Watson & Crick").
Ex. 1043 in IPR2018-00318 filed Dec. 15, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00318 filed Dec. 15, 2017, Feb. 11, 2015 Final Written Decision in IPR2013-00517.
Ex. 1045 in IPR2018-00318 filed Dec. 15, 2017, May 9, 2016 Federal Circuit Opinion Affirming IPR2013-00517.

Ex. 1046 in IPR2018-00318 filed Dec. 15, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00318 filed Dec. 15, 2017, Aug. 30, 2013 Substitute Columbia Patent Owner Response in IPR2012-00007, Paper 77.
Ex. 1048 in IPR2018-00318 filed Dec. 15, 2017, Jul. 25, 2014 Final Written Decision in IPR2013-00128, Paper 92.
Ex. 1049 in IPR2018-00318 filed Dec. 15, 2017, Oct. 28, 2014 Final Written Decision in IPR2013-00266, Paper 73.
Ex. 1050 in IPR2018-00318 filed Dec. 15, 2017, Jan. 29, 2016 Federal Circuit Opinion Affirming IPR2013-00128 and IPR2013-00266.
Ex. 1051 in IPR2018-00318 filed Dec. 15, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00318 filed Dec. 15, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00318 filed Dec. 15, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00318 filed Dec. 15, 2017, U.S. Pat. No. 8,088,575 ("Ju") issued Jan. 3, 2012.
Ex. 1055 in IPR2018-00318 filed Dec. 15, 2017, Stryer, "Biochemistry", Fourth Edition, W.H. Freeman and Co., New York (1995) ("Stryer").
Ex. 1056 in IPR2018-00318 filed Dec. 15, 2017, Columbia's Amended Complaint for Patent Infringement, C.A. No. 17-973 (GMS), USDC District of Delaware, dated Aug. 1, 2017.
Ex. 1057 in IPR2018-00318 filed Dec. 15, 2017, Curriculum Vitae of Floyd Romesberg, Ph.D. , dated Oct. 2017.
Ex. 1058 in IPR2018-00318 filed Dec. 15, 2017, List of documents considered by Floyd Romesberg, Ph.D.
Ex. 1059 in IPR2018-00318 filed Dec. 15, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1062 in IPR2018-00318 filed Dec. 15, 2017, Excerpts from Prosecution History of U.S. Pat. No. 9,719,139.
Ex. 1063 in IPR2018-00318 filed Dec. 15, 2017, Declaration of Jingyue Ju from Prosecution History of U.S. Pat. No. 9,719,139, dated May 2, 2017.
Ex. 1064 in IPR2018-00318 filed Dec. 15, 2017, Declaration of Floyd Romesberg, Ph.D. For '139, dated Dec. 15, 2017.
Exhibit 2001 in IPR2018-00318 filed Apr. 9, 2018, Declaration Patent Owner's Mandatory Notices Pursuant to 37 C.F.R. 42.8, Paper 4, dated Mar. 14, 2018.
Exhibit 2002 in IPR2018-00318 filed Apr. 9, 2018, U.S. Pat. No. 7,790,869 ("Ju") issued Sep. 7, 2010.
Exhibit 2003 in IPR2018-00318 filed Apr. 9, 2018, U.S. Pat. No. 7,713,698 ("Ju") issued May 11, 2010.
Exhibit 2004 in IPR2018-00318 filed Apr. 9, 2018, U.S. Pat. No. 8,088,575 ("Ju") issued Jan. 3, 2012.
Exhibit 2006 in IPR2018-00318 filed Apr. 9, 2018, Excerpts from the Prosecution History of U.S. Pat. No. 9,725,480 DATE.
Exhibit 2007 in IPR2018-00318 filed Apr. 9, 2018, IPR2013-00517, Ex. 2011, Declaration of Floyd Romesberg, Ph.D. (May 5, 2014).
Exhibit 2008 in IPR2018-00318 filed Apr. 9, 2018, IPR2013-00517, Paper 32, Illumina¿¿¿s Patent Owner Response (May 5, 2014).
Exhibit 2009 in IPR2018-00318 filed Apr. 9, 2018, Excerpts from the Ex Parte Reexamination History of U.S. Pat. No. 5,808,045 DATE.
Exhibit 2011 in IPR2018-00318 filed Apr. 9, 2018, PCT Publication WO 98/33939 (Anazawa) (English translation) DATE.
Exhibit 2012 in IPR2018-00318 filed Apr. 9, 2018, Metzker, et al. (1998) Stop-start DNA synthesis in the base addition sequencing scheme (BASS), Genome Mapping & Sequencing, Abstract.

(56) References Cited

OTHER PUBLICATIONS

Exhibit 2013 in IPR2018-00318 filed Apr. 9, 2018, PCT Publication WO 00/53805 (Stemple) dated Sep. 14, 2000.
Exhibit 2014 in IPR2018-00318 filed Apr. 9, 2018, Metzker, et al. (1994)) Stop-start DNA synthesis in the base addition sequencing scheme (BASS), Genome Mapping & Sequencing, Abstract.
Exhibit 2015 in IPR2018-00318 filed Apr. 9, 2018, U.S. Pat. No. 7,541,444, Milton, issued Jun. 2, 2009.
Exhibit 2016 in IPR2018-00318 filed Apr. 9, 2018, U.S. Pat. No. 7,771,973, Milton, issued Aug. 10, 2010.
Exhibit 2017 in IPR2018-00318 filed Apr. 9, 2018, U.S. Patent Application Publication No. 2007/0166705, Milton, published Jul. 19, 2007.
Exhibit 2018 in IPR2018-00318 filed Apr. 9, 2018, Boons, et al. (1996) a new procedure for the isomerization of substituted and unsubstituted allyl ethers of carbohydrates, Chem. Commun., pp. 141-142.
Exhibit 2019 in IPR2018-00318 filed Apr. 9, 2018, Ochiai, et al. (1996) Hypervalent (tert-Butylperoxy)iodanes generate iodine-centered radicals at room temperature in solution: oxidation and deprotection of benzyl and allyl ethers, and evidence for generation of $\alpha$-oxy carbon radicals, J. am. Chem. Soc., 118:7716-7730.
Exhibit 2020 in IPR2018-00318 filed Apr. 9, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00318 filed Apr. 9, 2018, U.S. Pat. No. 6,232,465, Hiatt, issued May 15, 2001.
Exhibit 2022 in IPR2018-00318 filed Apr. 9, 2018, Excerpts from the Ex Parte Reexamination History of U.S. Pat. No. 6,232,465.
Exhibit 2023 in IPR2018-00318 filed Apr. 9, 2018, Solexa, Inc. Fed. R. Civ. P. 7.1 Statement (Feb. 19, 2010).
Exhibit 2024 in IPR2018-00318 filed Apr. 9, 2018, Solexa, Inc. Schedule 13D-A Submission to the United States Securities and Exchange Commission (Feb. 2, 2007).
Exhibit 2025 in IPR2018-00318 filed Apr. 9, 2018, Litosh, et al. (2011) Improved nucleotide selectivity and termination of 3'-OH unblocked reversible terminators by molecular tuning of 2-nitrobenzyl alkylated HOMedU triphosphates, Nucleic Acids Research 39(6):e39.
Exhibit 2026 in IPR2018-00318 filed Apr. 9, 2018, IPR2017-02172, Paper 6, Preliminary Response of Patent Owner Illumina Cambridge Ltd. (Jan. 23, 2018).
Exhibit 2027 in IPR2018-00318 filed Apr. 9, 2018, IPR2017-02174, Paper 6, Preliminary Response of Patent Owner Illumina Cambridge Ltd. (Jan. 23, 2018).
Exhibit 2028 in IPR2018-00318 filed Apr. 9, 2018, U.S. Pat. No. 7,566,537 (Balasubramanian) issued Jul. 28, 2009.
Exhibit 2029 in IPR2018-00318 filed Apr. 9, 2018, No. 2015-1123 (CAFC), Brief of Patent Owner-Appellant Illumina Cambridge Ltd., D.I. 27 (Mar. 10, 2015).
Exhibit 2030 in IPR2018-00318 filed Apr. 9, 2018, IPR2013-00266, Paper 39, Patent Owner Illumina Reply to Petitioner Opposition to Illumina Motion to Amend (Mar. 21, 2014).
Exhibit 2031 in IPR2018-00318 filed Apr. 9, 2018, Canard & Sarfati (1994) DNA polymerase fluorescent substrates with reversible 3'-tags, Gene, 148:1-6.
Exhibit 2032 in IPR2018-00318 filed Apr. 9, 2018, IPR2013-00517, Paper 84, Oral Hearing Transcript (Feb. 2, 2015).
Exhibit 2033 in IPR2018-00318 filed Apr. 9, 2018, IPR2013-00517, Paper 64, Illumina Motion for Observations on the Cross-Examination Testimony of Bruce Branchaud, Ph.D. and Michael Metzker, Ph.D. (Sep. 2, 2014).
Exhibit 2034 in IPR2018-00318 filed Apr. 9, 2018, IPR2012-00007, Paper 5, Petition for Inter Partes Review of U.S. Pat. No. 7,790,869 (Sep. 16, 2012).
Exhibit 2035 in IPR2018-00318 filed Apr. 9, 2018, IPR2013-00517, Exhibit 1025, Deposition of Floyd Romesberg, Ph.D. (Jul. 28, 2014).
Exhibit 2036 in IPR2018-00318 filed Apr. 9, 2018, IPR2012-00007, Paper 38, Decision on Petition for Inter Partes Review (Mar. 12, 2013).
Exhibit 2039 in IPR2018-00318 filed Apr. 9, 2018, PCT Publication WO 98/33939 (Japanese language version of Anazawa) published Aug. 6, 1998.
Exhibit 2040 in IPR2018-00318 filed Apr. 9, 2018, Translation Affidavit for Anazawa, dated Sep. 12, 2012.
Exhibit 2041 in IPR2018-00318 filed Apr. 9, 2018, Welch & Burgess (1999) Synthesis of fluorescent, photolabile 3'-0-protected nucleoside triphosphates for the base addition sequencing scheme, Nucleosides & Nucleotides, 18(2):197-201.
Exhibit 2042 in IPR2018-00318 filed Apr. 9, 2018, IPR2013-00517, Paper 68, Illumina Opposition to IBS Motion to Exclude Evidence.
Exhibit 2043 in IPR2018-00318 filed Apr. 9, 2018, Excerpts from the Prosecution History of U.S. Pat. No. 7,771,973.
Exhibit 2044 in IPR2018-00318 filed Apr. 9, 2018, Excerpts from the Prosecution History of U.S. Pat. No. 9,719,139.
Exhibit 2046 in IPR2018-00318 filed Apr. 9, 2018, Froehler, et al. (1992) Oligodeoxynucleotides containing C-5 propyne analogs of 2'-deoxyuridine and 2'-deoxycytidine, Tetradedron Letters, 33(37):5307-5310.
Paper 3 in IPR2018-00318 filed Jan. 3, 2018, Illumina's Supplemental Mandatory Notice—Related Matters.
Paper 5 in IPR2018-00318 filed Jan. 10, 2018Notice of Accord Filing Date.
Paper 7 in IPR2018-00318 filed Jan. 16, 2018, Columbia's Exhibit List No. 1 Under 37 CFR 42.63(e).
Paper 8 in IPR2018-00318 filed Apr. 6, 2018, Illumina's Supplemental Mandatory Notice.
Paper 9 in IPR2018-00318 filed Apr. 9, 2018, Patent Owner Preliminary Response.
Petition for Inter Partes Review of U.S. Pat. No. 9,725,480, Case No. IPR2018-00385.
Ex. 1001 in IPR2018-00385 filed Dec. 22, 2017, U.S. Pat. No. 9,718,852 ("Ju") issued Aug. 1, 2017.
Ex. 1002 in IPR2018-00385 filed Dec. 22, 2017, U.S. Pat. No. 9,708,358 ("Ju") issued Jul. 18, 2017.
Ex. 1003 in IPR2018-00385 filed Dec. 22, 2017, U.S. Pat. No. 9,719,139 ("Ju") issued Jul. 18, 2017.
Ex. 1004 in IPR2018-00385 filed Dec. 22, 2017, U.S. Pat. No. 9,725,480 ("Ju") issued Aug. 8, 2017.
Ex. 1005 in IPR2018-00385 filed Dec. 22, 2017, Mar. 6, 2014 IPR2012-00007, Paper 140, Final Written Decision.
Ex. 1006 in IPR2018-00385 filed Dec. 22, 2017, Mar. 6, 2014 IPR2012-00006, Paper 128, Final Written Decision.
Ex. 1007 in IPR2018-00385 filed Dec. 22, 2017, Mar. 6, 2014 IPR2013-00011, Paper 130, Final Written Decision.
Ex. 1008 in IPR2018-00385 filed Dec. 22, 2017, Jul. 17, 2015 Federal Circuit Opinion Affirming IPR2012-00006, IPR2012-00007 and IPR2013-00011.
Ex. 1010 in IPR2018-00385 filed Dec. 22, 2017, U.S. Pat. No. 7,790,869 ("Ju") issued Sep. 7, 2010.
Ex. 1011 in IPR2018-00385 filed Dec. 22, 2017, Alberts, et al., "Molecular Biology of the Cell", Third Edition, Garland Publishing Inc., New York (1994).
Ex. 1013 in IPR2018-00385 filed Dec. 22, 2017, WO 91/06678 ("Tsien") published May 16, 1991.
Ex. 1014 in IPR2018-00385 filed Dec. 22, 2017, Prober, et al., "A System for Rapid DNA Sequencing with Fluorescent Chain-Terminating Dideoxynucleotides", Science, 238:336-341 (1987) ("Prober").
Ex. 1015 in IPR2018-00385 filed Dec. 22, 2017, U.S. Pat. No. 5,547,839 ("Dower") issued Aug. 20, 1996.
Ex. 1016 in IPR2018-00385 filed Dec. 22, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00385 filed Dec. 22, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2018-00385 filed Dec. 22, 2017, Sanger et. al., "DNA sequencing with chain-terminating inhibitors", Proc. Natl. Acad. Sci. USA, 74:5463-5467 (1977) ("Sanger").

(56) References Cited

OTHER PUBLICATIONS

Ex. 1019 in IPR2018-00385 filed Dec. 22, 2017, U.S. Pat. No. 7,270,951 ("Stemple") issued Sep. 18, 2017.
Ex. 1020 in IPR2018-00385 filed Dec. 22, 2017, U.S. Pat. No. 5,302,509 ("Cheeseman") issued Apr. 12, 1994.
Ex. 1021 in IPR2018-00385 filed Dec. 22, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2018-00385 filed Dec. 22, 2017, Welch, et al., "Syntheses of Nucleosides Designed for Combinatorial DNA Sequencing", Chem. Eur. J., 5:951-960 (1999) ("Welch").
Ex. 1024 in IPR2018-00385 filed Dec. 22, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1025 in IPR2018-00385 filed Dec. 22, 2017, Seela, et al., "7-Deazapurine containing DNA", Nucleic Acids Research, 20:55-61 (1991) ("Seela 1991").
Ex. 1026 in IPR2018-00385 filed Dec. 22, 2017, U.S. Pat. No. 4,804,748 ("Seela Patent") issued Feb. 14, 1989.
Ex. 1027 in IPR2018-00385 filed Dec. 22, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00385 filed Dec. 22, 2017, Excerpts from Sep. 4, 2013 Deposition Transcript of Dr. George L. Trainor in IPR2012-00007.
Ex. 1029 in IPR2018-00385 filed Dec. 22, 2017, U.S. Pat. No. 5,151,507 ("Hobbs") issued Sep. 29, 1992.
Ex. 1030 in IPR2018-00385 filed Dec. 22, 2017, Ramzaeva, et al., "88. 7-Substituted 7-Deasa-2'-deoxyguanosines: Regioselective Halogenation of Pyrrolo[2,3-d] pyrimidine Nucleosides", Helvetica Chimica Acta, 78:1083-1090 (1995) ("Ramzaeva 1995").
Ex. 1031 in IPR2018-00385 filed Dec. 22, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1032 in IPR2018-00385 filed Dec. 22, 2017, Seela, et al., "Duplex Stability of Oligonucleotides Containing 7-Substituted 7-Deaza- and 8-Aza-7-Deazapurine Nucleosides", Nucleosides, Nucleotides & Nucleotides, 16:963-966 (1997) ("Seela 1997").
Ex. 1033 in IPR2018-00385 filed Dec. 22, 2017, Ramzaeva, et al., "123. 7-Deazaguanine DNA: Oligonucleotides with Hydrophobic or Cationic Side Chains", Helvetica Chimica Acta, 80:1809-1822 (1997) ("Ramzaeva 1997").
Ex. 1034 in IPR2018-00385 filed Dec. 22, 2017, Jun. 25, 2013 Declaration of Dr. George L. Trainor from IPR2012-00006.
Ex. 1035 in IPR2018-00385 filed Dec. 22, 2017, Boss, et al., "Cleavage of Allyl Ethers with Pd/C", Angew. Chem. Int. Ed. Engl., 15:558-559 (1976) ("Boss").
Ex. 1036 in IPR2018-00385 filed Dec. 22, 2017, Qian, et al., "Unexpected Enzymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998) ("Qian").
Ex. 1037 in IPR2018-00385 filed Dec. 22, 2017, Kamal, et al., "A Mild and Rapid Regeneration of Alcohols from their Allylic Ethers by Chlorotrimethylsilane/Sodium Iodide", Tetrahedron Letters, 40:371-372 (1999) ("Kamal").
Ex. 1039 in IPR2018-00385 filed Dec. 22, 2017, Vollhardt, et al., "Organic Chemistry", Second Edition, W.H. Freeman and Co., New York (1994) ("Vollhardt").
Ex. 1040 in IPR2018-00385 filed Dec. 22, 2017, Yu, et al., "Cyanine dye dUTP analogs for enzymatic labeling of DNA probes", Nucleic Acids Research, 22:3226-3232 (1994) ("Yu").
Ex. 1041 in IPR2018-00385 filed Dec. 22, 2017, Livak, et al., "Detection of single base differences using biotinylated nucleotides with very long linker arms", Nucleic Acids Research, 20:4831-4837 (1992) ("Livak").

Ex. 1042 in IPR2018-00385 filed Dec. 22, 2017, Watson, et al., "Genetical Implication of the Structure of Deoxyribonucleic Acid", Nature, 171:964-967 (1953) ("Watson & Crick").
Ex. 1043 in IPR2018-00385 filed Dec. 22, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00385 filed Dec. 22, 2017, Feb. 11, 2015 Final Written Decision in IPR2013-00517.
Ex. 1045 in IPR2018-00385 filed Dec. 22, 2017, May 9, 2016 Federal Circuit Opinion Affirming IPR2013-00517.
Ex. 1046 in IPR2018-00385 filed Dec. 22, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00385 filed Dec. 22, 2017, Aug. 30, 2013 Substitute Columbia Patent Owner Response in IPR2012-00007, Paper 77.
Ex. 1048 in IPR2018-00385 filed Dec. 22, 2017, Jul. 25, 2014 Final Written Decision in IPR2013-00128, Paper 92.
Ex. 1049 in IPR2018-00385 filed Dec. 22, 2017, Oct. 28, 2014 Final Written Decision in IPR2013-00266, Paper 73.
Ex. 1050 in IPR2018-00385 filed Dec. 22, 2017, Jan. 29, 2016 Federal Circuit Opinion Affirming IPR2013-00128 and IPR2013-00266.
Ex. 1051 in IPR2018-00385 filed Dec. 22, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00385 filed Dec. 22, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00385 filed Dec. 22, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00385 filed Dec. 22, 2017, U.S. Pat. No. 8,088,575 ("Ju") C.
Ex. 1055 in IPR2018-00385 filed Dec. 22, 2017, Stryer, "Biochemistry", Fourth Edition, W.H. Freeman and Co., New York (1995) ("Stryer").
Ex. 1057 in IPR2018-00385 filed Dec. 22, 2017, Curriculum Vitae of Floyd Romesberg, Ph.D. dated Oct. 2017.
Ex. 1058 in IPR2018-00385 filed Dec. 22, 2017, List of documents considered by Floyd Romesberg, Ph.D.
Ex. 1059 in IPR2018-00385 filed Dec. 22, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1061 in IPR2018-00385 filed Dec. 22, 2017, Columbia's Second Amended Complaint for Patnet Infringement, C.A. No. 17-973 (GMS) USDC, District of Delaware, dated Aug. 15, 2017.
Ex. 1068 in IPR2018-00385 filed Dec. 22, 2017, Excerpts from Prosecution History of U.S. Pat. No. 9,725,480 ("Ju").
Ex. 1069 in IPR2018-00385 filed Dec. 22, 2017, Declaration of Jingyue Ju from Prosecution History of U.S. Pat. No. 9,725,480 ("Ju") dated May 26, 2017.
Ex. 1070 in IPR2018-00385 filed Dec. 22, 2017, Declaration of Dr. Floyd Romesberg, Ph.D. for '480 dated Dec. 21, 2017.
Ex. 1071 in IPR2018-00385 filed Dec. 22, 2017, U.S. Pat. No. 5,844,106 ("Seela II") issued Dec. 1, 1998.
Ex. 1072 in IPR2018-00385 filed Dec. 22, 2017, Excerpts from Prosecution History of U.S. Pat. No. 9,718,852 ("Ju").
Ex. 1073 in IPR2018-00385 filed Dec. 22, 2017, Excerpts from Prosecution History of U.S. Pat. No. 9,719,139 ("Ju").
Ex. 1074 in IPR2018-00385 filed Dec. 22, 2017, Excerpts from Prosecution History of U.S. Pat. No. 9,708,358 ("Ju").
Exhibit 2002 in IPR2018-00385 filed May 4, 2018, U.S. Pat. No. 7,790,869 (Ju) issued Sep. 7, 2010.
Exhibit 2003 in IPR2018-00385 filed May 4, 2018, U.S. Pat. No. 7,713,698 (Ju) issued May 11, 201.

(56) References Cited

OTHER PUBLICATIONS

Exhibit 2004 in IPR2018-00385 filed May 4, 2018, U.S. Pat. No. 8,088,575 (Ju) issued Jan. 3, 2012.
Exhibit 2007 in IPR2018-00385 filed May 4, 2018, IPR2013-00517, Ex. 2011, Declaration of Floyd Romesberg, Ph.D. (May 5, 2014).
Exhibit 2008 in IPR2018-00385 filed May 4, 2018, IPR2013-00517, Paper 32, Illumina's Patent Owner Response (May 5, 2014).
Exhibit 2009 in IPR2018-00385 filed May 4, 2018, Excerpts from the Ex Parte Reexamination History of U.S. Pat. No. 5,808,045.
Exhibit 2011 in IPR2018-00385 filed May 4, 2018, PCT Publication WO 98/33939 published Aug. 6, 1998 (Anazawa) (English translation).
Exhibit 2012 in IPR2018-00385 filed May 4, 2018, Metzker et al., Elimination of Residual Natural Nucleotides from 3'-O-Modified-dNTP Syntheses by Enzymatic Mop-Up, BioTechniques, 25:814-817 (1998).
Exhibit 2013 in IPR2018-00385 filed May 4, 2018, PCT Publication WO 00/53805 (Stemple) published Sep. 14, 2000.
Exhibit 2014 in IPR2018-00385 filed May 4, 2018, Metzker, et al., Stop-Start DNA Synthesis in the Base Addition Sequencing Scheme (BASS), Genome Mapping & Sequencing (1994).
Exhibit 2015 in IPR2018-00385 filed May 4, 2018, U.S. Pat. No. 7,541,444 (Milton) issued Jun. 2, 2009.
Exhibit 2016 in IPR2018-00385 filed May 4, 2018, U.S. Pat. No. 7,771,973 (Milton) issued Aug. 10, 2010.
Exhibit 2017 in IPR2018-00385 filed May 4, 2018, U.S. Patent Application Publication No. 2007/0166705 (Milton) published Jul. 19, 2007.
Exhibit 2018 in IPR2018-00385 filed May 4, 2018, Boons (1996) A new procedure for the isomerization of substituted and unsubstituted allyl ethers of carbohydrates, Chem. Commun., pp. 141-142.
Exhibit 2019 in IPR2018-00385 filed May 4, 2018, Ochiai (1996) Hypervalent (tert-Butylperoxy)iodanes generate iodine-centered radicals at room temperature in solution: oxidation and deprotection of benzyl and allyl ethers, and evidence for generation of α-oxy carbon radicals, J. am. Chem. Soc., 118:7716-7730.
Exhibit 2020 in IPR2018-00385 filed May 4, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00385 filed May 4, 2018, U.S. Pat. No. 6,232,465 (Hiatt) issued May 15, 2001.
Exhibit 2022 in IPR2018-00385 filed May 4, 2018, Excerpts from the Ex Parte Reexamination History of U.S. Pat. No. 6,232,465.
Exhibit 2023 in IPR2018-00385 filed May 4, 2018, Solexa, Inc. Fed. R. Civ. P. 7.1 Statement (Feb. 19, 2010).
Exhibit 2024 in IPR2018-00385 filed May 4, 2018, Solexa, Inc. Schedule 13D-A Submission to the United States Securities and Exchange Commission (Feb. 2, 2007).
Exhibit 2025 in IPR2018-00385 filed May 4, 2018, Litosh (2011) Improved nucleotide selectivity and termination of 3'-OH unblocked reversible terminators by molecular tuning of 2-nitrobenzyl alkylated HOMedU triphosphates, Nucleic Acids Research 39(6):e39.
Exhibit 2026 in IPR2018-00385 filed May 4, 2018, IPR2017-02172, Paper 6, Preliminary Response of Patent Owner Illumina Cambridge Ltd. (Jan. 23, 2018).
Exhibit 2027 in IPR2018-00385 filed May 4, 2018, IPR2017-02174, Paper 6, Preliminary Response of Patent Owner Illumina Cambridge Ltd. (Jan. 23, 2018).
Exhibit 2028 in IPR2018-00385 filed May 4, 2018, U.S. Pat. No. 7,566,537 (Balasubramanian) issued Jul. 28, 2009.
Exhibit 2029 in IPR2018-00385 filed May 4, 2018, No. 2015-1123 (CAFC), Brief of Patent Owner-Appellant Illumina Cambridge Ltd., D.I. 27 (Mar. 10, 2015).
Exhibit 2030 in IPR2018-00385 filed May 4, 2018, IPR2013-00266, Paper 39, Patent Owner Illumina Reply to Petitioner Opposition to Illumina Motion to Amend (Mar. 21, 2014).
Exhibit 2031 in IPR2018-00385 filed May 4, 2018, Canard & Sarfati (1994) DNA polymerase fluorescent substrates with reversible 3'-tags, Gene, 148:1-6.

Exhibit 2032 in IPR2018-00385 filed May 4, 2018, IPR2013-00517, Paper 84, Oral Hearing Transcript (Feb. 2, 2015).
Exhibit 2033 in IPR2018-00385 filed May 4, 2018, IPR2013-00517, Paper 64, Illumina Motion for Observations on the Cross-Examination Testimony of Bruce Branchaud, Ph.D. and Michael Metzker, Ph.D. (Sep. 2, 2014).
Exhibit 2034 in IPR2018-00385 filed May 4, 2018, IPR2012-00007, Paper 5, Petition for Inter Partes Review of U.S. Pat. No. 7,790,869 (Sep. 16, 2012).
Exhibit 2035 in IPR2018-00385 filed May 4, 2018, IPR2013-00517, Exhibit 1025, Deposition of Floyd Romesberg, Ph.D. (Jul. 28, 2014).
Exhibit 2036 in IPR2018-00385 filed May 4, 2018, IPR2012-00007, Paper 38, Decision on Petition for Inter Partes Review (Mar. 12, 2013).
Exhibit 2037 in IPR2018-00385 filed May 4, 2018, Assignment data in connection with U.S. Patent Application Publication No. 2007/0166705 and U.S. Pat. No. 7,541,444.
Exhibit 2038 in IPR2018-00385 filed May 4, 2018, Assignment data in connection with U.S. Pat. No. 6,232,465.
Exhibit 2039 in IPR2018-00385 filed May 4, 2018, PCT Publication WO 98/33939 published Aug. 6, 1998 (Japanese language version of Anazawa).
Exhibit 2040 in IPR2018-00385 filed May 4, 2018, Translation Affidavit for Anazawa, dated Sep. 12, 2012.
Exhibit 2041 in IPR2018-00385 filed May 4, 2018, Welch & Burgess (1999) Synthesis of Fluorescent, photolabile 3'-0-protected nucleoside triphosphates for the base addition sequencing scheme, Nucleosides & Nucleotides, 18(2):197-201.
Exhibit 2042 in IPR2018-00385 filed May 4, 2018, IPR2013-00517, Paper 68, Illumina Opposition to IBS Motion to Exclude Evidence.
Exhibit 2043 in IPR2018-00385 filed May 4, 2018, Excerpts from the Prosecution History of U.S. Pat. No. 7,771,973.
Exhibit 2047 in IPR2018-00385 filed May 4, 2018, Excerpts from the Prosecution History of U.S. Pat. No. 9,725,480.
Exhibit 2048 in IPR2018-00385 filed May 4, 2018, Excerpts from the Prosecution History of U.S. Pat. No. 9,718,852.
Exhibit 2049 in IPR2018-00385 filed May 4, 2018, IPR2018-00291, Petition for Inter Partes Review of U.S. Pat. No. 9,718,852 (Dec. 8, 2017).
Paper 3 in IPR2018-00385 filed Jan. 3, 2018, Illumina's Supplemental Mandatory Notice—Related Matters.
Paper 4 in IPR2018-00385 filed Jan. 11, 2018, Patent Owner's Mandatory Notices Pursuant to 37 CFR 42.8.
Paper 5 in IPR2018-00385 filed Feb. 6, 2081, Notice of Accord Filing Date.
Paper 7 in IPR2018-00385 filed Mar. 15, 2018, Columbia's Exhibit List No. 1.
Paper 8 in IPR2018-00385 filed Apr. 6, 2018, Illumina's Supplemental Mandatory Notice.
Paper 11 in IPR2018-00385 filed May 2, 2018, Illumina Updated Exhibit List.
Paper 12 in IPR2018-00385 filed May 3, 2018, Supplemental Mandatory Notices Pursuant to 37 CFR 42.8(a)(3).
Paper 13 in IPR2018-00385 filed May 4, 2018, Patent Owner Preliminary Response.
Petition for Inter Partes Review of U.S. Pat. No. 9,708,358, Case No. IPR2018-00322.
Ex. 1002 in IPR2018-00322 filed Dec. 18, 2017, U.S. Pat. No. 9,708,358 ("Ju") issued Jul. 18, 2017.
Ex. 1005 in IPR2018-00322 filed Dec. 18, 2017, Mar. 6, 2014 IPR2012-00007, Paper 140, Final Written Decision.
Ex. 1006 in IPR2018-00322 filed Dec. 18, 2017, Mar. 6, 2014 IPR2012-00006, Paper 128, Final Written Decision.
Ex. 1007 in IPR2018-00322 filed Dec. 18, 2017, Mar. 6, 2014 IPR2013-00011, Paper 130, Final Written Decision.
Ex. 1008 in IPR2018-00322 filed Dec. 18, 2017, Jul. 17, 2015 Federal Circuit Opinion Affirming IPR2012-00006, IPR2012-00007 and IPR2013-00011.
Ex. 1010 in IPR2018-00322 filed Dec. 18, 2017, U.S. Pat. No. 7,790,869 ("Ju") issued Sep. 7, 2010.

(56) References Cited

OTHER PUBLICATIONS

Ex. 1011 in IPR2018-00322 filed Dec. 18, 2017, Alberts, et al., "Molecular Biology of the Cell", Third Edition, Garland Publishing Inc., New York (1994).
Ex. 1013 in IPR2018-00322 filed Dec. 18, 2017, WO 91/06678 ("Tsien") published May 16, 1991.
Ex. 1014 in IPR2018-00322 filed Dec. 18, 2017, Prober, et al., "A System for Rapid DNA Sequencing with Flourescent Chain-Terminating Dideoxynucleotides", Science, 238:336-341 (1987) ("Prober").
Ex. 1015 in IPR2018-00322 filed Dec. 18, 2017, U.S. Pat. No. 5,547,839 ("Dower") issued Aug. 1996.
Ex. 1016 in IPR2018-00322 filed Dec. 18, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00322 filed Dec. 18, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2018-00322 filed Dec. 18, 2017, Sanger et. al., "DNA sequencing with chain-terminating inhibitors", Proc. Natl. Acad. Sci. USA, 74:5463-5467 (1977) ("Sanger").
Ex. 1019 in IPR2018-00322 filed Dec. 18, 2017, U.S. Pat. No. 7,270,951 ("Stemple") issued Sep. 18, 2017.
Ex. 1020 in IPR2018-00322 filed Dec. 18, 2017, U.S. Pat. No. 5,302,509 ("Cheeseman") issued Apr. 12, 1994.
Ex. 1021 in IPR2018-00322 filed Dec. 18, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2018-00322 filed Dec. 18, 2017, Welch, et al., "Syntheses of Nucleosides Designed for Combinatorial DNA Sequencing", Chem. Eur. J., 5:951-960 (1999) ("Welch").
Ex. 1024 in IPR2018-00322 filed Dec. 18, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1027 in IPR2018-00322 filed Dec. 18, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00322 filed Dec. 18, 2017, Excerpts from Sep. 4, 2013 Deposition Transcript of Dr. George L. Trainor in IPR2012-00007.
Ex. 1029 in IPR2018-00322 filed Dec. 18, 2017, U.S. Pat. No. 5,151,507 ("Hobbs") issued Sep. 29, 1992.
Ex. 1031 in IPR2018-00322 filed Dec. 18, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1034 in IPR2018-00322 filed Dec. 18, 2017, Jun. 26, 2013 Declaration of Dr. George L. Trainor from IPR2012-00006.
Ex. 1035 in IPR2018-00322 filed Dec. 18, 2017, Boss, et al., "Cleavage of Allyl Ethers with Pd/C", Angew. Chem. Int. Ed. Engl., 15:558-559 (1976) ("Boss").
Ex. 1036 in IPR2018-00322 filed Dec. 18, 2017, Qian, et al., "Unexpected Ensymatic Fucosylation of the Hindered Tertiary Alcohol of 3-C-Methyl-N-Acetyllactosamine Produces a Novel Analogue of the LeX-Trisaccharide", *Journal* of the American Chemical Society, 120:2184-2185 (1998) ("Qian").
Ex. 1037 in IPR2018-00322 filed Dec. 18, 2017, Kamal, et al., "A Miled and Rapid Regeneration of Alcohols from their Allylic Ethers by Chlorotrimethylsilane/Sodium Iodide", Tetrahedron Letters, 40:371-372 (1999) ("Kamal").
Ex. 1038 in IPR2018-00322 filed Dec. 18, 2017, Excerpts from Prosecution History of U.S. Pat. No. 9,725,480 ("Ju").
Ex. 1039 in IPR2018-00322 filed Dec. 18, 2017, Vollhardt, et al., "Organic Chemistry", Second Edition, W.H. Freeman and Co., New York (1994) ("Vollhardt").
Ex. 1040 in IPR2018-00322 filed Dec. 18, 2017, Yu, et al., "Cyanine dye dUTP analogs for enzymatic labeling of DNA probes", Nucleic Acids Research, 22:3226-3232 (1994) ("Yu").
Ex. 1041 in IPR2018-00322 filed Dec. 18, 2017, Livak, et al., "Detection of single base differences using biotinylated nucleotides with very long linker arms", Nucleic Acids Research, 20:4831-4837 (1992) ("Livak").
Ex. 1042 in IPR2018-00322 filed Dec. 18, 2017, Watson, et al., "Genetical Implication of the Structure of Deoxyribonucleic Acid", Nature, 171:964-967 (1953) ("Watson & Crick").
Ex. 1043 in IPR2018-00322 filed Dec. 18, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00322 filed Dec. 18, 2017, Feb. 11, 2015 Final Written Decision in IPR2013-00517.
Ex. 1045 in IPR2018-00322 filed Dec. 18, 2017, May 9, 2016 Federal Circuit Opinion Affirming IPR2013-00517.
Ex. 1046 in IPR2018-00322 filed Dec. 18, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00322 filed Dec. 18, 2017, Aug. 30, 2013 Substitute Columbia Patent Owner Response in IPR2012-00007, Paper 77.
Ex. 1048 in IPR2018-00322 filed Dec. 18, 2017, Jul. 25, 2014 Final Written Decision in IPR2013-00128, Paper 92.
Ex. 1049 in IPR2018-00322 filed Dec. 18, 2017, Oct. 28, 2014 Final Written Decision in IPR2013-00266, Paper 73.
Ex. 1050 in IPR2018-00322 filed Dec. 18, 2017, Jan. 29, 2016 Federal Circuit Opinion Affirming IPR2013-00128 and IPR2013-00266.
Ex. 1051 in IPR2018-00322 filed Dec. 18, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00322 filed Dec. 18, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00322 filed Dec. 18, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00322 filed Dec. 18, 2017, U.S. Pat. No. 8,088,575 ("Ju") issued Sep. 29, 1992.
Ex. 1055 in IPR2018-00322 filed Dec. 18, 2017, Stryer, "Biochemistry", Fourth Edition, W.H. Freeman and Co., New York (1995) ("Stryer").
Ex. 1057 in IPR2018-00322 filed Dec. 18, 2017, Curriculum Vitae of Floyd Romesberg, Ph.D. dated Oct. 2017.
Ex. 1058 in IPR2018-00322 filed Dec. 18, 2017, List of documents considered by Floyd Romesberg, Ph.D.
Ex. 1059 in IPR2018-00322 filed Dec. 18, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1060 in IPR2018-00322 filed Dec. 18, 2017, Columbia's Complaint for Patent Infringement, USDC, District of Delaware, filed Jul. 18, 2017.
Ex. 1065 in IPR2018-00322 filed Dec. 18, 2017, Excerpts from Prosecution History of U.S. Pat. No. 9,708,358.
Ex. 1066 in IPR2018-00322 filed Dec. 18, 2017, Declaration of Jingyue Ju from Prosecution History of U.S. Pat. No. 9,708,358, dated May 2, 2017.
Ex. 1067 in IPR2018-00322 filed Dec. 18, 2017, Declaration of Floyd Romesberg, Ph.D. For '358, dated Dec. 15, 2017.
Exhibit 2001 in IPR2018-00322 filed Jan. 16, 2018, Declaration of Robert S. Schwartz in Support of Patent Owner's Motion for Admission Pro Hac Vice.
Exhibit 2002 in IPR2018-00322 filed Apr. 9, 2018, U.S. Pat. No. 7,790,869 (Ju) issued Sep. 7, 2010.

(56) References Cited

OTHER PUBLICATIONS

Exhibit 2003 in IPR2018-00322 filed Apr. 9, 2018, U.S. Pat. No. 7,713,698 (Ju) issued May 11, 2010.
Exhibit 2004 in IPR2018-00322 filed Apr. 9, 2018, U.S. Pat. No. 8,088,575 (Ju) issued Jan. 3, 2012.
Exhibit 2006 in IPR2018-00322 filed Apr. 9, 2018, Excerpts from the Prosecution History of U.S. Pat. No. 9,725,480.
Exhibit 2007 in IPR2018-00322 filed Apr. 9, 2018, IPR2013-00517, Ex. 2011, Declaration of Floyd Romesberg, Ph.D. (May 5, 2014).
Exhibit 2008 in IPR2018-00322 filed Apr. 9, 2018, IPR2013-00517, Paper 32, Illumina Patent Owner Response (May 5, 2014).
Exhibit 2009 in IPR2018-00322 filed Apr. 9, 2018, Excerpts from the Ex Parte Reexamination History of U.S. Pat. No. 5,808,045.
Exhibit 2010 in IPR2018-00322 filed Apr. 9, 2018, Assignment data in connection with U.S. Pat. No. 5,808,045.
Exhibit 2011 in IPR2018-00322 filed Apr. 9, 2018, PCT Publication WO 98/33939 (Anazawa) (English translation).
Exhibit 2012 in IPR2018-00322 filed Apr. 9, 2018, Metzker, et al., Elimination of Residual Natural Nucleotides from 3'-O-Modified-dNTP Syntheses by Enzymatic Mop-Up, BioTechniques, 25:814-817 (1998).
Exhibit 2013, PCT Publication WO 00/53805 (Stemple) published Sep. 14, 2000.
Exhibit 2014 in IPR2018-00322 filed Apr. 9, 2018, Metzker, et al., Stop-Start DNA Synthesis in the Base Addition Sequencing Scheme (BASS), Genome Mapping & Sequencing (1994).
Exhibit 2015 in IPR2018-00322 filed Apr. 9, 2018, U.S. Pat. No. 7,541,444 (Milton) issued Jun. 2, 2009.
Exhibit 2016 in IPR2018-00322 filed Apr. 9, 2018, U.S. Pat. No. 7,771,973 (Milton) issued Aug. 10, 2010.
Exhibit 2017 in IPR2018-00322 filed Apr. 9, 2018, U.S. Patent Application Publication No. 2007/0166705 (Milton) published Jul. 19, 2007.
Exhibit 2018 in IPR2018-00322 filed Apr. 9, 2018, Boons, et al. (1996) A new procedure for the isomerization of substituted and unsubstituted allyl ethers of carbohydrates, Chem. Commun., pp. 141-142.
Exhibit 2019 in IPR2018-00322 filed Apr. 9, 2018, Ochiai, et al. (1996) Hypervalent (tert-Butylperoxy)iodanes generate iodine-centered radicals at room temperature in solution: oxidation and deprotection of benzyl and allyl ethers, and evidence for generation of α-oxy carbon radicals, J. am. Chem. Soc., 118:7716-7730.
Exhibit 2020 in IPR2018-00322 filed Apr. 9, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00322 filed Apr. 9, 2018, U.S. Pat. No. 6,232,465 (Hiatt) issued May 15, 2001.
Exhibit 2022 in IPR2018-00322 filed Apr. 9, 2018, Excerpts from the Ex Parte Reexamination History of U.S. Pat. No. 6,232,465.
Exhibit 2023 in IPR2018-00322 filed Apr. 9, 2018, Solexa, Inc. Fed. R. Civ. P. 7.1 Statement (Feb. 19, 2010).
Exhibit 2024 in IPR2018-00322 filed Apr. 9, 2018, Solexa, Inc. Schedule 13D-A Submission to the United States Securities and Exchange Commission (Feb. 2, 2007).
Exhibit 2026 in IPR2018-00322 filed Apr. 9, 2018, IPR2017-02172, Paper 6, Preliminary Response of Patent Owner Illumina Cambridge Ltd. (Jan. 23, 2018).
Exhibit 2027 in IPR2018-00322 filed Apr. 9, 2018, IPR2017-02174, Paper 6, Preliminary Response of Patent Owner Illumina Cambridge Ltd. (Jan. 23, 2018).
Exhibit 2028 in IPR2018-00322 filed Apr. 9, 2018, U.S. Pat. No. 7,566,537 (Balasubramanian) issued Jul. 28, 2009.
Exhibit 2029 in IPR2018-00322 filed Apr. 9, 2018, No. 2015-1123 (CAFC), Brief of Patent Owner-Appellant Illumina Cambridge Ltd., D.I. 27 (Mar. 10, 2015).
Exhibit 2030 in IPR2018-00322 filed Apr. 9, 2018, IPR2013-00266, Paper 39, Patent Owner Illumina Reply to Petitioner Opposition to Illumina Motion to Amend (Mar. 21, 2014).
Exhibit 2031 in IPR2018-00322 filed Apr. 9, 2018, Canard & Sarfati (1994).
Exhibit 2033 in IPR2018-00322 filed Apr. 9, 2018, IPR2013-00517, Paper 64, Illumina Motion for Observations on the Cross-Examination Testimony of Bruce Branchaud, Ph.D. and Michael Metzker, Ph.D. (Sep. 2, 2014).
Exhibit 2034 in IPR2018-00322 filed Apr. 9, 2018, PR2012-00007, Paper 5, Petition for Inter Partes Review of U.S. Pat. No. 7,790,869 (Sep. 16, 2012).
Exhibit 2036 in IPR2018-00322 filed Apr. 9, 2018, IPR2012-00007, Paper 38, Decision on Petition for Inter Partes Review (Mar. 12, 2013).
Exhibit 2035 in IPR2018-00322 filed Apr. 9, 2018, IPR2013-00517, Exhibit 1025, Deposition of Floyd Romesberg, Ph.D. (Jul. 28, 2014).
Exhibit 2037 in IPR2018-00322 filed Apr. 9, 2018, Assignment data in connection with U.S. Patent Application Publication No. 2007/0166705 and U.S. Pat. No. 7,541,444.
Exhibit 2038 in IPR2018-00322 filed Apr. 9, 2018, Assignment data in connection with U.S. Pat. No. 6,232,465, x filed Apr. 9, 2018.
Exhibit 2039 in IPR2018-00322 filed Apr. 9, 2018, PCT Publication WO 98/33939 published Aug. 6, 1998 (Japanese language version of Anazawa).
Exhibit 2040 in IPR2018-00322 filed Apr. 9, 2018, Translation Affidavit for Anazawa, dated Sep. 12, 2012.
Exhibit 2041 in IPR2018-00322 filed Apr. 9, 2018, Welch & Burgess (1999) Synthesis of Fluorescent, photolabile 3'-0-protected nucleoside triphosphates for the base addition sequencing scheme, Nucleosides & Nucleotides, 18(2):197-201.
Exhibit 2042 in IPR2018-00322 filed Apr. 9, 2018, IPR2013-00517, Paper 68, Illumina Opposition to Ibs Motion to Exclude Evidence.
Exhibit 2043 in IPR2018-00322 filed Apr. 9, 2018, Excerpts from the Prosecution History of U.S. Pat. No. 7,771,973.
Exhibit 2045 in IPR2018-00322 filed Apr. 9, 2018, Excerpts from the Prosecution History of U.S. Pat. No. 9,708,358.
Exhibit 2046 in IPR2018-00322 filed Apr. 9, 2018, Froehler, et al. (1992) Oligodeoxynucleotides containing C-5 propyne analogs of 2'-deoxyuridine and 2'-deoxycytidine, Tetradedron Letters, 33(37):5307-5310.
Paper 3 in IPR2018-00322 filed Jan., 2018, Illumina's Supplemental Mandatory Notice—Related Matters.
Paper 4 in IPR2018-00322 filed Jan. 8, 2018Patent Owner's Mandatory Notices Pursuant to 37 CFR 42.8.
Paper 5 in IPR2018-00322 Jan. 10, 2018, Notice of Accord Filing Date.
Paper 6 in IPR2018-00322 filed Jan. 16, 2018Patent Owner's Motion for Admission Pro Hac Vice.
Paper 7 in IPR2018-00322 filed Jan. 16, 2018, Columbia's Exhibit List No. 1 Under 37 CFR 42.63(e).
Paper 8 in IPR2018-00322 filed Apr. 6, 2018, Illumina's Supplemental Mandatory Notice.
Paper 9 in IPR2018-00322 filed Apr. 9, 2018, Patent Owner Preliminary Response.
IPR2018-00291, Institution Decision, Paper No. 16 (Jun. 25, 2018).
IPR2018-00318, Institution Decision, Paper No. 16 (Jul. 3, 2018).
IPR2018-00322, Institution Decision, Paper No. 16 (Jul. 3, 2018).
IPR2018-00385, Institution Decision, Paper No. 20 (Jul. 27, 2018).
IPR2018-00797, Patent Owner's Preliminary Response, Paper No. 14 (Jul. 6, 2018).
IPR2018-00797, Exhibit 2046, Froehler, et al. "Oligodeoxynucleotides Containing C-5 Propyne Analogs of 2'-Deoxyuridine and 2'-Deoxycytidine," Tetrahedron Letters, 33:5307-5310 (1992).
IPR2018-00797, Exhibit 2051, Excerpts from the Prosecution History of U.S. Pat. No. 9,868,985 not included in Ex. 1076.
IPR2018-00797, Exhibit 2052, Declaration of Steven M. Menchen, Ph.D.
IPR2018-00797, Exhibit 2053, Metzker "Sequencing technologies—the next generation," Nature Review, 11(1):31-46 (2010).
IPR2018-00797, Exhibit 2054, Ronaghi, et al. "A Sequencing Method Based on Real-Time Pyrophosphate," Science, 281(5375):363-365 (1998).
IPR2018-00797, Exhibit 2055, Genomeweb, "Illumina Closes Solexa Acquisition," Jan. 26, 2007.

(56) References Cited

OTHER PUBLICATIONS

IPR2018-00797, Exhibit 2056, Lee et al., "Unwinding of Double-Stranded DNA Helix by Dehydration," Proc. Natl. Acad. Sci. USA, 78(5):2838-2842 (1981).
IPR2018-00797, Exhibit 2057, Lindahl, "Instability and decay of the primary structure of DNA," Nature, 362:709-715 (1993).
IPR2018-00797, Exhibit 2058, Mozingo, "Palladium Catalysts," Organic Syntheses, Coll. 3:658 (1955).
IPR2018-00797, Exhibit 2059, Johnson, "Rapid Quench Kinetic Analysis of Polymerases, Adenosinetriphosphatases, and Enzyme Intermediates," Methods in Enzymology, 249:38-61 (1995).
IPR2018-00797, Exhibit 2061, Zielonacka-Lis, "The Acidic Hydrolysis of Nucleosides and Nucleotides," Nucleosides & Nucleotides, 8(3):838-405 (1989).
IPR2018-00797, Exhibit 2062, IPR2013-00128, Ex. 1029, Substitute Declaration of Floyd Romesberg, Ph.D. (Jan. 9, 2014).
IPR2018-00797, Exhibit 2065, Excerpts from the Ex Parte Reexamination History of U.S. Pat. No. 6,232,465.
IPR2018-00797, Exhibit 2066, Curriculum Vitae of Steven M. Menchen, Ph.D.
Bechtereva et al., "DNA sequencing with thermostable Tet DNA polymerase from Thermus thermophiles," Nucleic Acids Research, 1989,17(24):10507.
IPR 2018-00797, Institution Decision, Paper No. 20 (Sep. 18, 2018).
IPR2018-00797, Exhibit 2080, IPR2013-00128, Exhibit 1033, Deposition of Floyd Romesberg, Ph.D. (Jan. 14, 2014).
IPR2018-00797, Exhibit 2081, IPR2013-00266, Exhibit 2037, Second Declaration of Floyd Romesberg, Ph.D. (Mar. 21, 2014).
IPR2018-00797, Exhibit 2082, IPR2013-00266, Exhibit 1042, Deposition of Floyd Romesberg, Ph.D. (Apr. 10, 2014).
IPR2018-00797, Exhibit 2083, IPR2013-00128, Substitute Exhibit 2009, Substitute Declaration of Floyd Romesberg, Ph.D. in Support of Patent Owner's Motion to Amend (Feb. 19, 2014).
IPR2018-00797, Exhibit 2084, Jannasch, "Deep sea hydrothermal vents: underwater oases," The NEB Transcript (1992).
IPR2018-00797, Exhibit 2085, Levine, et al. "The relationship of structure to the effectiveness of denaturing agents for deoxyribonucleic acid," Biochem., 2(1):168-175 (1963).
IPR2018-00797, Exhibit 2086, Kit, "Deoxyribonucleic acids," Annu. Rev. Biochem., 32:43-82 (1963).
IPR2018-00797, Exhibit 2087, Lindahl & Nyberg, "Rate of Depurination of Native Deoxyribonucleic Acid," Biochem., 11(19):3610-3618 (1972).
IPR2018-00797, Exhibit 2089, Hamed et al., "Palladium(II)-Catalyzed Oxidation of Aldehydes and Ketones. 1. Carbonylation of Ketones with Carbon Monoxide Catalyzed by Palladium(II) Chloride in Methanol," J. Org. Chem., 66(1):180-185 (2001).
IPR2018-00797, Exhibit 2090, Exhibit from Deposition of Dr. Floyd Romesberg, Sep. 19-20, 2018, in IPR2018-00291, -00318, -00322, and -00385 (Handwritten calculations).
IPR2018-00797, Exhibit 2094, Pillai & Nandi, "Interaction of Palladium (II) With DNA," Biochimica et Biophysica Acta, 474:11-16 (1977).
IPR2018-00797, Exhibit 2095, U.S. Pat. No. 6,664,079, issued Dec. 16, 2003, Ju et al.
IPR2018-00797, Exhibit 2096, Transcript for the Deposition of Dr. Floyd Romesberg, Sep. 19-20, 2018, in IPR2018-00291, -00318, -00322, and -00385 (Original Transcript).
IPR2018-00797, Exhibit 2097, Qian et al., "Chemoenzymatic synthesis of α-(1→3)-Gal(NAc) terminating glycosides of complex tertiary sugar alcohols," J. Am. Chem. Soc. 121:12063-12072 (1999).
IPR2018-00797, Exhibit 2098, Kang, "Complete reverse regioselection in Wacker oxidation of acetonides and cyclic carbonates of allylic diols," J. Org. Chem. 60:4678-4679 (1995).
IPR2018-00797, Exhibit 2099, U.S. Pat. No. 5,858,671, issued Jan. 12, 1999, Jones.
IPR2018-00797, Exhibit 2100, U.S. Pat. No. 6,013,445, issued Jan. 11, 2000, Albrecht et al.
IPR2018-00797, Exhibit 2101, Tsuji, et al., "Regioselective oxidation of internal olefins bearing neighboring oxygen functions by means of palladium catalysts," Tetrahedron Letters, 23(26):2679-2682 (1982).
IPR2018-00797, Exhibit 2102, Qian, "Enzymatic and Chemical Synthesis of Oligosaccharide Analogs," Thesis, University of Alberta (2000).
IPR2018-00797, Exhibit 2103, Project Information for Dr. Romesberg NIH Grant, "Evolving Novel Polymerases for Genome Sequencing," dated Oct. 9, 2018.
IPR2018-00797, Exhibit 2104, Genomeweb, "Helicos and Columbia to Test Scripps' Improved Polymerase for Next-Gen Sequencing," Oct. 3, 2006.
IPR2018-00797, Exhibit 2105, Bieg et al., "Isomerization and cleavage of allyl ethers of carbohydrates by trans-[Pd(NH3)2 Cl2]," J. Carbohydrate Chem., 4(3):441-446 (1985).
IPR2018-00797, Exhibit 2106, Ochiai, "Hypervalent (tert-butylperoxy) iodanes generate iodinecentered radicals at room temperature in solution," J. Am. Chem. Soc., 118:7716-7730 (1996).
IPR2018-00797, Exhibit 2107, Katritzky, "The origins of the benzotrizole project, its versatility illustrated by a new —C═CHCH+ OEt synthon, and novel synthesis of alpha beta-unsaturated aldehydes and ketones, furans, pyrroles and allyl ethers," Synthesis, 1315-1323 (1995).
IPR2018-00797, Exhibit 2108, Documents Considered by Dr. Menchen for Exhibit 2114, Oct. 25, 2018.
IPR2018-00797, Exhibit 2109, WO 96/27025, published Sep. 6, 1996, Rabani.
IPR2018-00797, Exhibit 2110, WO 96/23807, published Aug. 8, 1996, Kwiatkowski.
IPR2018-00797, Exhibit 2111, Martinez et al., "Acyclic nucleoside triphosphate analogs as terminators in biocatalytic DNA replication," Bioorganic & Medicinal Chemistry Letters, 7(23):3013-3016 (1997).
IPR2018-00797, Exhibit 2112, Hawley's Condensed Chemical Dictionary, Thirteenth Edition (1997) (excerpts).
IPR2018-00797, Exhibit 2113, Transcript for the Deposition of Dr. Floyd Romesberg, Oct. 9, 2018, in IPR2018-00797.
IPR2018-00797, Exhibit 2114, Declaration of Steven M. Menchen, Ph.D., Oct. 26, 2018 (IPR2018-00797).
IPR2018-00797, Exhibit 2115, Parshall, "Homogeneous Catalysis, the Applications and Chemistry of Catalysis by Soluble Transition Metal Complexes," John Wiley and Sons (1980) (excerpts).
IPR2018-00322, Exhibit 2116, Declaration of Steven M. Menchen, Ph.D., Oct. 26, 2018 (IPR2018-00291, -00318, -00322, and -00385).
IPR2018-00797, Exhibit 2117, IPR2017-02172, Paper 22, Decision Denying Petitioner's Request for Rehearing (Aug. 2, 2018).
IPR2018-00797, Exhibit 2118, Dr. Romesberg NIH Grant, "Evolving Novel Polymerases for Genome Sequencing".
IPR2018-00797, Exhibit 2119, Solexa, Inc.'s Form 425 Submission to the United States Securities and Exchange Commission (Nov. 14, 2006).
IPR2018-00797, Exhibit 2125, Eckert et al., "DNA Polymerase Fidelity and the Polymerase Chain Reaction," Genome Research, 1:17-24 (1991).
IPR2018-00797, Exhibit 2126, Transcript for the Deposition of Dr. Floyd Romesberg, Sep. 19-20, 2018, in IPR2018-00291, -00318, -00322, and -00385 (Revised Transcript).
IPR2018-00797, Exhibit 2127, Proposed Standing Protective Order, filed Oct. 26, 2018.
IPR2018-00797, Exhibit 2128, Protective Order in D.Del. C.A. No. 17-973 (GMS), filed Oct. 26, 2018.
IPR2018-00797, Paper 29, Patent Owner's Response, filed Oct. 26, 2018.
IPR2018-00797, Paper 30, Columbia's Exhibit List No. 4 under 37 C.F.R. § 42.63(e), filed Oct. 26, 2018.
IPR2917-00322, Paper 31, Patent Owner's Response dated Oct. 26, 2018.
IPR2917-00322, Paper 32, Columbia's Exhibit List No. 4 under 37 C.F.R. § 42.63(e), filed Oct. 26, 2018.
IPR2018-00291, Petitioner's Reply, filed Jan. 22, 2019.
IPR2018-00318, Petitioner's Reply, filed Jan. 22, 2019.
IPR2018-00322, Petitioner's Reply, filed Jan. 22, 2019.

(56) References Cited

OTHER PUBLICATIONS

IPR2018-00385, Petitioner's Reply, filed Jan. 22, 2019.
IPR2018-00797, Petitioner's Reply, filed Jan. 22, 2019.
IPR2018-00291, IPR2018-00318, IPR2018-00322, IPR2018-00385, Patent Owner's Sur-Reply, filed Feb. 5, 2019.
IPR2018-00797, Patent Owner's Sur-Reply, filed Feb. 5, 2019.
IPR2018-00291, IPR2018-00318, IPR2018-00322, IPR2018-00385, Illumina Motion to Exclude Columbia Evidence, filed Feb. 7, 2019.
IPR2018-00797, Illumina Motion to Exclude Columbia Evidence, filed Feb. 7, 2019.
IPR2018-00291, IPR2018-00318, IPR2018-00322, IPR2018-00385, Patent Owner's Opposition ot Petitioner's Motion to Exclude, filed Feb. 19, 2019.
IPR2018-00797, Patent Owner's Opposition ot Petitioner's Motion to Exclude, filed Feb. 19, 2019.
IPR2018-00291, IPR2018-00318, IPR2018-00322, IPR2018-00385, Illumina's Reply to Patent Owner's Opposition to Motion to Exclude, filed Feb. 26, 2019.
IPR2018-00797, Illumina's Reply to Patent Owner's Opposition to Motion to Exclude Columbia Evidence, filed Feb. 26, 2019.
IRP2018-00322, Exhibit 1091, filed Feb. 26, 2019, U.S. Pat. No. 6,111,116 to Benson and Menchen et al., issued Aug. 20, 2000.
IRP2018-00322, Exhibit 1092, filed Feb. 26, 2019, U.S. Pat. No. 6,248,884 to Lam and Menchen et al., dated Jun. 19, 2001.
IRP2018-00322, Exhibit 1093, filed Feb. 26, 2019, Ruparel and Ju et al., Proc. Natl. Acad. Sci. USA, 102:5932-5937 (2005) ("Ruparel").
IRP2018-00322, Exhibit 1094, filed Feb. 26, 2019, Genet et al., Tetrahedron, 50:497-503 (1994) ("Genet 1994").
IRP2018-00322, Exhibit 1095, filed Feb. 26, 2019, Apr. 20, 2018 IPR2017-02174, Paper 20, Decision Denying Institution of Inter Partes Review, filed Apr. 20, 2018.
IRP2018-00322, Exhibit 1096, filed Feb. 26, 2019, Apr. 20, 2018 IPR2017-02172, Paper 20, Decision Denying Institution of Inter Partes Review, filed Apr. 20, 2018.
IRP2018-00322, Exhibit 1097, filed Feb. 26, 2019, Nucleic Acids Research publication information for Metzker et al., "Termination of DNA synthesis by novel 3'-modifieddeoxyribonucleoside 5'-triphosphates," 22:4259-67 (1994).
IRP2018-00322, Exhibit 1098, filed Feb. 26, 2019, Sep. 4-5, 2013 Deposition Transcript of Dr. George L. Trainor in IPR2012-00007.
IRP2018-00322, Exhibit 1099, filed Feb. 26, 2019, IUPAC, Nomenclature of Organic Chemistry, Eds. Rigaudy et al., International Union of Pure and Applied Chemistry, Organic Chemistry Division, Commission on Nomenclature of Organic Chemistry, Pergamon Press, 1979.
IRP2018-00322, Exhibit 1100, filed Feb. 26, 2019, Jensen, "Organizations for Standardization of Quantities and Units," Metrologia 31:503-509 (1994/1995).
IRP2018-00322, Exhibit 1101, filed Feb. 26, 2019, Greene and Wuts, "Protective Groups in Organic Synthesis," third edition, John Wiley & Sons (1999).
IRP2018-00322, Exhibit 1102, filed Feb. 26, 2019, CRC Handbook of Chemistry and Physics, eds. Weast et al., 72nd edition, CRC Press (1991).
IRP2018-00322, Exhibit 1103, filed Feb. 26, 2019, McGraw-Hill Dictionary of Chemistry, ed. Parker, McGraw-Hill Book Co., 1984.
IRP2018-00322, Exhibit 1104, filed Feb. 26, 2019, Solomons, "Organic Chemistry", Fourth Edition, John Wiley & Sons (1988) ("Solomons").
IRP2018-00322, Exhibit 1105, filed Feb. 26, 2019, Morrison et al., "Organic Chemistry," Third Edition, Allyn and Bacon, Inc. (1973).
IRP2018-00322, Exhibit 1106, filed Feb. 26, 2019, U.S. Pat. No. 5,808.045 to Hiatt et al. ("Hiatt"), dated Sep. 15, 1998.
IRP2018-00322, Exhibit 1107, filed Feb. 26, 2019, U.S. Pat. No. 6,627,436 to Sorge at al. ("Sorge"), dated Sep. 30, 2002.
IRP2018-00322, Exhibit 1108, filed Feb. 26, 2019, Cyclist® Exo-Pfu DNA Sequencing Kit, Instruction Manual, Stratagene (1998).
IRP2018-00322, Exhibit 1109, filed Feb. 26, 2019, Hedden et al., "DNA Sequence Determination Using Exonuclease-Deficient Pfu DNA Polymerase in a Cycle Sequencing Format," 207th ACS National Meeting, Abstract 121, American Chemical Society, San Diego, CA, Mar. 13-17, 1994.
IRP2018-00322, Exhibit 1112, filed Feb. 26, 2019, Transcript for the Deposition of Steven M. Menchen, Jan. 14, 2019 in IPR2018-00291, -00318, -00322, -00385 and -00797.
IRP2018-00322, Exhibit 1113, filed Feb. 26, 2019, Transcript for the Deposition of Steven M. Menchen, Jan. 15, 2019 in IPR2018-00291, -00318, -00322, -00385 and -00797.
IRP2018-00322, Exhibit 1114, filed Feb. 26, 2019, Lemaire-Audoire and Genet et al., Tetrahedron Letters, 35:8783-8786 (1994).
IRP2018-00322, Exhibit 1115, filed Feb. 26, 2019, Lemaire-Audoire and Genet et al., Journal of Molecular Catalysis A: Chemical, 116:247-258 (1997).
IRP2018-00322, Exhibit 1116, filed Feb. 26, 2019, Qinglin Meng thesis from Dr. Ju's laboratory at Columbia University (2006).
IRP2018-00322, Exhibit 1118, filed Feb. 26, 2019, Kutateladze, FEBS, 207:205-212 (1986).
IRP2018-00322, Exhibit 1119, filed Feb. 26, 2019, Reply Declaration of Floyd Romesberg, Ph.D., dated Jan. 22, 2019.
IRP2018-00322, Exhibit 1120, filed Feb. 26, 2019, "The Race for the $1000 Genome," Science, 311:1544-46 (2006).
IRP2018-00322, Exhibit 1122, filed Feb. 26, 2019, Gardner et al., Nucleic Acids Research, 27:2545-53 (1999).
IRP2018-00322, Exhibit 1124, filed Feb. 26, 2019, WO 04/018493 Solexa, dated Mar. 4, 2004.
IRP2018-00322, Exhibit 1125, filed Feb. 26, 2019, WO 04/018497 Solexa, dated Mar. 4, 2004.
IRP2018-00322, Exhibit 1126, filed Feb. 26, 2019, Kraevskii et al., Molecular Biology 21:25-29 (1987).
IRP2018-00322, Exhibit 1127, filed Feb. 26, 2019, IPR2012-00007, Paper 82, Opposition to Motion to Amend, dated Sep. 27, 2013.
IRP2018-00322, Exhibit 1128, filed Feb. 26, 2019, IPR2012-00007, Paper 83, Reply to Patent Owner Response, dated Sep. 27, 2013.
IRP2018-00322, Exhibit 1129, filed Feb. 26, 2019, Ju et. al., PNAS USA, 103:19635-40 (2006) ("Ju 2006").
IRP2018-00322, Exhibit 1130, filed Feb. 26, 2019, U.S. Pat. No. 5,614,365 to Tabor et al., dated Mar. 25, 1997.
IRP2018-00322, Exhibit 1131, filed Feb. 26, 2019, U.S. Pat. No. 5,885,813 to Davis et al., dated Mar. 23, 1999.
IRP2018-00322, Exhibit 1133, filed Feb. 26, 2019, Southworth et al., PNAS USA, 93:5281-85 (1996).
IRP2018-00322, Exhibit 1134, filed Feb. 26, 2019, Takahashi et al., Bulletin of the Chemical Society of Japan, 45:230-36 (1972).
IRP2018-00322, Exhibit 1135, filed Feb. 26, 2019, Yamamoto et al., Organometallics, 5:1559-67 (1986).
IRP2018-00322, Exhibit 1136, filed Feb. 26, 2019, Fields, Methods in Molecular Biology, vol. 35, Peptide Synthesis Protocols, Chapter 2, Humana Press 1994.
IRP2018-00322, Exhibit 1137, filed Feb. 26, 2019, IPR2012-00007, Paper 79 Substitute Columbia Motion to Amend, dated Aug. 30, 2013.
IRP2018-00322, Exhibit 1138, filed Feb. 26, 2019, List of documents considered by Dr. Romesberg.
IRP2018-00322, Exhibit 2131, filed Feb. 26, 2019, Metzker, et al., "Elimination of Residual Natural Nucleotides from 3'-O-Modified-dNTP Syntheses by Enzymatic Mop-Up," BioTechniques, 25:814-817 (1998) (Marked at Dr. Menchen'sDeposition).
IRP2018-00322, Exhibit 2132, filed Feb. 26, 2019, Jannasch, "Deep sea hydrothermal vents: underwater oases," The NEB Transcript (1992) (Marked at Dr. Menchen's Deposition).
IRP2018-00322, Exhibit 2140, filed Feb. 26, 2019, Transcript for the Deposition of Dr. Floyd Romesberg, Feb. 1, 2019, in IPR2018-00291, -00318, -00322, -00385, and -00797.
IRP2018-00322, Exhibit 2141, filed Feb. 26, 2019, Patent Owner's Oral Hearing Demonstratives (IPR2018-00291, -00318, -00322, -00385, -00797).
IPR2018-00291, IPR2018-00318, IPR2018-00322, PRI2018-00385, IRP2018-00797, Record of Oral Hearing held Mar. 5, 2019.
IPR2018-00291, IPR2018-00318, IPR2018-00322, PRI2018-00385, IRP2018-00797, Illumina's Supplemental Brief Regarding Estoppel, filed Mar. 26, 2019.

(56) References Cited

OTHER PUBLICATIONS

IPR2018-00291, IPR2018-00318, IPR2018-00322, PRI2018-00385, IRP2018-00797, Patent Owner's Additional Brief filed Mar. 26, 2019.
IPR2018-00291, IPR2018-00318, IPR2018-00322, PRI2018-00385, IRP2018-00797, Illumina's Supplemental Reply Regarding Estoppel, filed Apr. 2, 2019.
IPR2018-00291, IPR2018-00318, IPR2018-00322, PRI2018-00385, IRP2018-00797, Patent Owner's Reply to Petitioner's Supplemental Brief, filed Apr. 2, 2019.
IPR2018-00291, IPR2018-00318, IPR2018-00322, PRI2018-00385, Final Written Decision dated Jun. 21, 2019.
IPR2018-00291, IPR2018-00318, IPR2018-00322, PRI2018-00385, Errata dated Jun. 26, 2019.
IPR2018-00797 Final Written Decision dated Sep. 9, 2019.
Defendants' Answer to Illumina's First Amended Complaint for Patent Infringement and Counterclaim for Patent Infringement, US District Court for the Northern District of California, Case No. 19-cv-03770-WHO, dated Sep. 30, 2019.
Plaintiffs Illumina, Inc. and Illumina Cambridge Ltd.'s Motion to Strike and Dismiss Defendants' BGI Americas Corp., MGI Tech Co., Ltd., MGI Americas, Inc., and Complete Genomics Inc.'s Affirmative Defenses and Counterclaims, USDC Northern District of California, San Francisco Division, Case No. 3:19-cv-03770-WHO, dated Nov. 4, 2019, and Appendix.

Blackburn et al., 1996, Nucleic Acids in Chemistry and Biology, 2nd Ed. Oxford University Press.
Bochet, Dec. 13, 2001, Photolabile protecting groups and linkers, J. Chem. Soc, Perkin Tran 1, 0:125-142.
Current Protocols in Nucleic Acid Chemistry, vol. 1, 2011, John Wiley & Sons Inc.
De Clercq, Jan. 2002, Strategies in the Design of Antiviral Drugs, Nature Reviews, Drug Discovery, 1:13-25.
Evans et al., Aug. 1986, 5-Azido-2'-deoxyuridine 5'-triphosphate: a photoaffinity-labeling reagent and tool for the enzymatic synthesis of photoactive DNA, Proc. Natl. Acad. Sci. USA, 83:5382-5386.
Jones et al., 1995, Minireview: nucleotide prodrugs, Antiviral Res, 27:1-17.
Keohavong et al., Dec. 1989, Fidelity of DNA polymerases in DNA amplification, Proc Natl Acad Sci USA, 86:9253-9257.
Lin et al., Feb. 5, 1993, Syntheses and biological evaluations of 3'-Deoxy-3'-C-Branched-Chain-Substituted Nucleosides, Journal of Medicinal Chemistry 36(3):353-362.
McNaught, 1006, Nomenclature of carbohydrates, Pure and Applied Chemistry, 68(10):1919-2008.
Saxon et al., Mar. 17, 2000, Cell surface engineering by a modified Staudinger reaction, Science 287(5460):2007-2010.
Wagner et al., Nov. 2000, Pronucleotides: toward the in vivo delivery of antiviral and anticancer nucleotides, Medicinal Research Reviews, 20(6):417-451.

* cited by examiner

MODIFIED NUCLEOSIDES OR NUCLEOTIDES

CROSS-REFERENCE TO RELATED APPLICATIONS

The present application is a continuation of U.S. application Ser. No. 15/444,826, filed Feb. 28, 2017 and to be issued as U.S. Pat. No. 10,407,721, which is a continuation of U.S. application Ser. No. 14/771,481, filed Aug. 28, 2015, now U.S. Pat. No. 9,593,373 issued on Mar. 14, 2017, which is the U.S. National Phase under 35 U.S.C. § 371 of International Application No. PCT/EP2013/055466, entitled "MODIFIED NUCLEOSIDES OR NUCLEOTIDES," filed Mar. 15, 2013, and published in English on Sep. 18, 2014 as WO 2014/139596 A1, each of which is hereby incorporated by reference in its entirety.

BACKGROUND

Field of the Invention

Some embodiments described herein relate to modified nucleotides or nucleosides comprising 3'-hydroxy protecting groups and their use in polynucleotide sequencing methods. Some embodiments described herein relate to method of preparing the 3'-hydroxy protected nucleotides or nucleosides.

Description of the Related Art

Advances in the study of molecules have been led, in part, by improvement in technologies used to characterize the molecules or their biological reactions. In particular, the study of the nucleic acids DNA and RNA has benefited from developing technologies used for sequence analysis and the study of hybridization events.

An example of the technologies that have improved the study of nucleic acids is the development of fabricated arrays of immobilized nucleic acids. These arrays consist typically of a high-density matrix of polynucleotides immobilized onto a solid support material. See, e.g., Fodor et al., Trends Biotech. 12: 19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., Proc. Natl. Acad. Sci. 92: 6379-6383, 1995).

One way of determining the nucleotide sequence of a nucleic acid bound to an array is called "sequencing by synthesis" or "SBS". This technique for determining the sequence of DNA ideally requires the controlled (i.e., one at a time) incorporation of the correct complementary nucleotide opposite the nucleic acid being sequenced. This allows for accurate sequencing by adding nucleotides in multiple cycles as each nucleotide residue is sequenced one at a time, thus preventing an uncontrolled series of incorporations occurring. The incorporated nucleotide is read using an appropriate label attached thereto before removal of the label moiety and the subsequent next round of sequencing.

In order to ensure only a single incorporation occurs, a structural modification ("protecting group") is added to each labeled nucleotide that is added to the growing chain to ensure that only one nucleotide is incorporated. After the nucleotide with the protecting group has been added, the protecting group is then removed, under reaction conditions which do not interfere with the integrity of the DNA being sequenced. The sequencing cycle can then continue with the incorporation of the next protected, labeled nucleotide.

To be useful in DNA sequencing, nucleotides, and more usually nucleotide triphosphates, generally require a 3'-hydroxy protecting group so as to prevent the polymerase used to incorporate it into a polynucleotide chain from continuing to replicate once the base on the nucleotide is added. There are many limitations on types of groups that can be added onto a nucleotide and still be suitable. The protecting group should prevent additional nucleotide molecules from being added to the polynucleotide chain whilst simultaneously being easily removable from the sugar moiety without causing damage to the polynucleotide chain. Furthermore, the modified nucleotide needs to be tolerated by the polymerase or other appropriate enzyme used to incorporate it into the polynucleotide chain. The ideal protecting group therefore exhibits long term stability, be efficiently incorporated by the polymerase enzyme, cause blocking of secondary or further nucleotide incorporation and have the ability to be removed under mild conditions that do not cause damage to the polynucleotide structure, preferably under aqueous conditions.

Reversible protecting groups have been described previously. For example, Metzker et al., (Nucleic Acids Research, 22 (20): 4259-4267, 1994) discloses the synthesis and use of eight 3'-modified 2-deoxyribonucleoside 5'-triphosphates (3'-modified dNTPs) and testing in two DNA template assays for incorporation activity. WO 2002/029003 describes a sequencing method which may include the use of an allyl protecting group to cap the 3'-OH group on a growing strand of DNA in a polymerase reaction.

In addition, we previously reported the development of a number of reversible protecting groups and methods of deprotecting them under DNA compatible conditions in International Application Publication No. WO 2004/018497, which is hereby incorporated by reference in its entirety.

SUMMARY

Some embodiments described herein relate to a modified nucleotide or nucleoside molecule comprising a purine or pyrimidine base and a ribose or deoxyribose sugar moiety having a removable 3'-hydroxy protecting group forming a structure —O—C(R)$_2$N$_3$ covalently attached to the 3'-carbon atom, wherein R is selected from the group consisting of hydrogen, —C(R$^1$)$_m$(R$^2$)$_n$, —C(=O)OR$^3$, —C(=O)NR$^4$R$^5$, —C(R$^6$)$_2$O(CH$_2$)$_p$NR$^7$R$^8$ and —C(R$^9$)$_2$O-Ph-C(=O)NR$^{10}$R$^{11}$;

each R$^1$ and R$^2$ is independently selected from hydrogen, optionally substituted alkyl or halogen;

R$^3$ is selected from hydrogen or optionally substituted alkyl;

each R$^4$ and R$^5$ is independently selected from hydrogen, optionally substituted alkyl, optionally substituted aryl, optionally substituted heteroaryl, or optionally substituted aralkyl;

each R$^6$ and R$^9$ is selected from hydrogen, optionally substituted alkyl or halogen;

each R$^7$, R$^8$, R$^{10}$ and R$^{11}$ is independently selected from hydrogen, optionally substituted alkyl, optionally substituted aryl, optionally substituted heteroaryl, or optionally substituted aralkyl;

m is an integer of 0 to 3; and n is an integer of 0 to 3; provided that the total of m+n equals to 3; and p is an integer of 0 to 6; provided that $R^1$ and $R^2$ cannot both be halogen; and at least one R is not hydrogen.

Some embodiments described herein relate to a method of preparing a growing polynucleotide complementary to a target single-stranded polynucleotide in a sequencing reaction, comprising incorporating a modified nucleotide molecule described herein into the growing complementary polynucleotide, wherein the incorporation of the modified nucleotide prevents the introduction of any subsequent nucleotide into the growing complementary polynucleotide.

Some embodiments described herein relate to a method for determining the sequence of a target single-stranded polynucleotide, comprising monitoring the sequential incorporation of complementary nucleotides, wherein at least one complementary nucleotide incorporated is a modified nucleotide molecule described herein; and detecting the identity of the modified nucleotide molecule. In some embodiments, the incorporation of the modified nucleotide molecule is accomplished by a terminal transferase, a terminal polymerase or a reverse transcriptase.

Some embodiments described herein relate to a kit comprising a plurality of modified nucleotide or nucleoside molecule described herein, and packaging materials therefor. In some embodiments, the identity of the modified nucleotide is determined by detecting the detectable label linked to the base. In some such embodiments, the 3'-hydroxy protecting group and the detectable label are removed prior to introducing the next complementary nucleotide. In some such embodiments, the 3'-hydroxy protecting group and the detectable label are removed in a single step of chemical reaction.

DETAILED DESCRIPTION

Figure 1A:
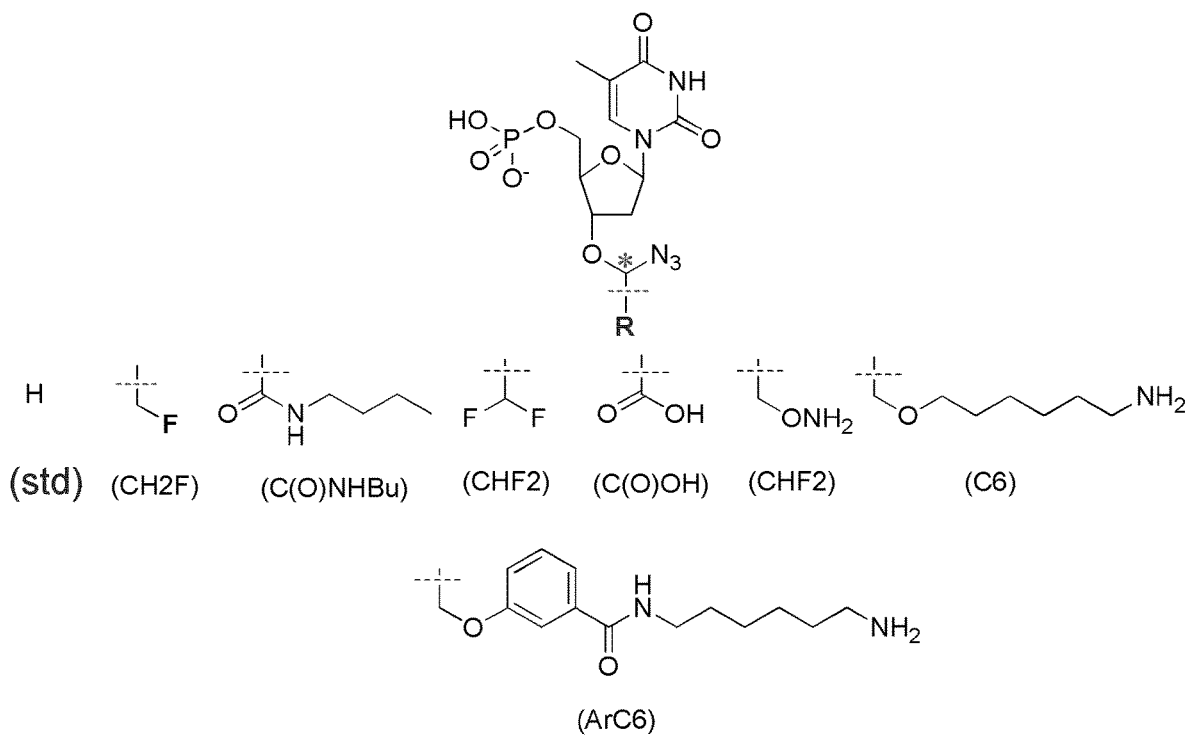
FIG. 1A illustrates a variety of 3'-OH protecting groups.

One embodiment is a modified nucleotide or nucleoside comprising a 3'-OH protecting group. In one embodiment, the 3'-OH protecting group is a monofluoromethyl substituted azidomethyl protecting group. In another embodiment, the 3'-OH protecting group is a C-amido substituted azidomethyl protecting group. Still another embodiment relates to modified nucleotides having difluoromethyl substituted azidomethyl 3'-OH protecting groups.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:

Ac Acetyl
$Ac_2O$ Acetic anhydride
aq. Aqueous
Bn Benzyl
Bz Benzoyl
BOC or Boc tert-Butoxycarbonyl
Bu n-Butyl
cat. Catalytic
Cbz Carbobenzyloxy
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP(s) Dideoxynucleotide(s)
DBU 1,8-Diazabicyclo[5.4.0]undec-7-ene
DCA Dichloroacetic acid
DCE 1,2-Dichloroethane
DCM Methylene chloride
DIEA Diisopropylethylamine
DMA Dimethylacetamide
DME Dimethoxyethane
DMF N,N'-Dimethylformamide
DMSO Dimethylsulfoxide
DPPA Diphenylphosphoryl azide
Et Ethyl
EtOAc Ethyl acetate
ffN Fully functional nucleotide
g Gram(s)
GPC Gel permeation chromatography
h or hr Hour(s)
iPr Isopropyl
KPi 10 mM potassium phosphate buffer at pH 7.0
KPS Potassium persulfate
IPA Isopropyl Alcohol
IMX Incorporation mix
LCMS Liquid chromatography-mass spectrometry
LDA Lithium diisopropylamide
m or min Minute(s)
mCPBA meta-Chloroperoxybenzoic Acid
MeOH Methanol
MeCN Acetonitrile
Mono-F —$CH_2F$
Mono-F ffN modified nucleotides with —$CH_2F$ substituted on methylene position of azidomethyl 3'-OH protecting group
mL Milliliter(s)
MTBE Methyl tertiary-butyl ether NaN₃ Sodium Azide
NHS N-hydroxysuccinimide
PG Protecting group
Ph Phenyl
ppt Precipitate
rt Room temperature
SBS Sequencing by Synthesis
TEA Triethylamine
TEMPO (2,2,6,6-Tetramethylpiperidin-1-yl)oxyl
TCDI 1,1'-Thiocarbonyl diimidazole
Tert, t tertiary
TFA Trifluoracetic acid
THF Tetrahydrofuran
TEMED Tetramethylethylenediamine
μL Microliter(s)

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, any "R" group(s) such as, without limitation, $R^2$, $R^3$, $R^4$, $R^5$, $R^6$, $R^7$, and $R^8$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring, an example of which is set forth below:

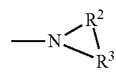

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from a group of functionalies including, but not limited to, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group, di-substituted amino group, and protected derivatives thereof.

As used herein, "alkyl" refers to a straight or branched hydrocarbon chain that comprises a fully saturated (no double or triple bonds) hydrocarbon group. In some embodiments, the alkyl group may have 1 to 20 carbon atoms (whenever it appears herein, a numerical range such as "1 to 20" refers to each integer in the given range inclusive of the endpoints; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having about 7 to about 10 carbon atoms. The alkyl group can also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some embodiments, cycloalkyl groups can contain 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, in some embodiments, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "heterocyclyl" refers to ring systems including at least one heteroatom (e.g., O, N, S). Such systems can be unsaturated, can include some unsaturation, or can contain some aromatic portion, or be all aromatic. A heterocyclyl group may be unsubstituted or substituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, in some embodiments, a heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, a "C-amido" group refers to a "—C(=O)N($R_a R_b$)" group in which $R_a$ and $R_b$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

As used herein, an "N-amido" group refers to a "RC(=O)N($R_a$)—" group in which R and $R_a$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom", "halogen" or "halo" as used herein, means any one of the radio-stable atoms of column 7 of the Periodic Table of the Elements, such as, fluorine, chlorine, bromine, and iodine.

The term "amine" as used herein refers to a —$NH_2$ group wherein one or more hydrogen can be optionally substituted by a R group. R can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "aldehyde" as used herein refers to a —$R_c$—C(O)H group, wherein $R_c$ can be absent or independently selected from alkylene, alkenylene, alkynylene, cycloalkylene, cycloalkenylene, cycloalkynylene, arylene, heteroarylene, heteroalicyclylene, aralkylene, or (heteroalicyclyl)alkylene.

The term "amino" as used herein refers to a —$NH_2$ group.

The term "hydroxy" as used herein refers to a —OH group.

The term "cyano" group as used herein refers to a "—CN" group.

The term "azido" as used herein refers to a —$N_3$ group.

The term "thiol" as used herein refers to a —SH group.

The term "carboxylic acid" as used herein refers to —C(O)OH.

The term "thiocyanate" as used herein refers to —S—CN group.

The term "oxo-amine" as used herein refers to —O—NH$_2$ group, wherein one or more hydrogen of the —NH$_2$ can be optionally substituted by a R group. R can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

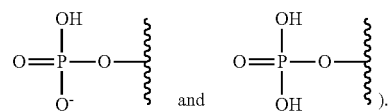 [SMILES: *OP(=O)([O-])O ; *OP(=O)(O)O]

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Sometimes, "protecting group" and "blocking group" can be used interchangeably.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively or additionally, the part of the spectrum can be one that passes through an interstitial region of a surface such as a region made of glass, plastic, silica, or other material set forth herein. In particular embodiments, radiation can be used that is capable of passing through a metal. Alternatively or additionally, radiation can be used that is masked by glass, plastic, silica, or other material set forth herein.

As used herein, the term "phasing" refers to phenomena in SBS that is caused by incomplete removal of the 3' terminators and fluorophores, and failure to complete the incorporation of a portion of DNA strands within clusters by polymerases at a given sequencing cycle. Pre-phasing is caused by the incorporation of nucleotides without effective 3' terminators and the incorporation event goes 1 cycle ahead. Phasing and pre-phasing cause the extracted intensities for a specific cycle to consist of the signal of the current cycle as well as noise from the preceding and following cycles. As the number of cycles increases, the fraction of sequences per cluster affected by phasing increases, hampering the identification of the correct base. Pre-phasing can be caused by the presence of a trace amount of unprotected or unblocked 3'-OH nucleotides during sequencing by synthesis (SBS). The unprotected 3'-OH nucleotides could be generated during the manufacturing processes or possibly during the storage and reagent handling processes. Accordingly, the discovery of nucleotide analogues which decrease the incidence of pre-phasing is surprising and provides a great advantage in SBS applications over existing nucleotide analogues. For example, the nucleotide analogues provided can result in faster SBS cycle time, lower phasing and pre-phasing values, and longer sequencing read length.

3'-OH Protecting Groups —C(R)$_2$N$_3$

Some embodiments described herein relate to a modified nucleotide or nucleoside molecule having a removable 3'-hydroxy protecting group —C(R)$_2$N$_3$, wherein R is selected from the group consisting of hydrogen, —C(R$^1$)$_m$(R$^2$)$_n$, —C(=O)OR$^3$, —C(=O)NR$^4$R$^5$, —C(R$^6$)$_2$O(CH$_2$)$_p$NR$^7$R$^8$ and —C(R$^9$)$_2$O-Ph-C(=O)NR$^{10}$R$^{11}$, wherein R$^1$, R$^2$, R$^3$, R$^4$, R$^5$, R$^6$, R$^7$, R$^8$, R$^9$, R$^{10}$, R$^{11}$, m, n and p are defined above.

In some embodiments, one of R is hydrogen and the other R is —C($R^1$)$_m$($R^2$)$_n$. In some such embodiments, —C($R^1$)$_m$($R^2$)$_n$ is selected from —CHF$_2$, —CH$_2$F, —CHCl$_2$ or —CH$_2$Cl. In one embodiment, —C($R^1$)$_m$($R^2$)$_n$ is —CHF$_2$. In another embodiment, —C($R^1$)$_m$($R^2$)$_n$ is —CH$_2$F.

In some embodiments, one of R is hydrogen and the other R is —C(=O)O$R^3$. In some such embodiment, $R^3$ is hydrogen.

In some embodiments, one of R is hydrogen and the other R is —C(=O)N$R^4R^5$. In some such embodiments, both $R^4$ and $R^5$ are hydrogen. In some other such embodiments, $R^4$ is hydrogen and $R^5$ is $C_{1-6}$ alkyl. In still some other embodiments, both $R^4$ and $R^5$ are $C_{1-6}$ alkyl. In one embodiment, $R^5$ is n-butyl. In another embodiment, both $R^4$ and $R^5$ are methyl.

In some embodiments, one of R is hydrogen and the other R is —C($R^6$)$_2$O(CH$_2$)$_p$N$R^7R^8$. In some such embodiments, both $R^6$ are hydrogen. In some such embodiments, both $R^7$ and $R^8$ are hydrogen. In some such embodiment, p is 0. In some other such embodiment, p is 6.

In some embodiments, one of R is hydrogen and the other R is —C($R^9$)$_2$O-Ph-C(=O)N$R^{10}R^{11}$. In some such embodiments, both $R^9$ are hydrogen. In some such embodiments, both $R^{10}$ and $R^{11}$ are hydrogen. In some other such embodiments, $R^{10}$ is hydrogen and $R^{11}$ is a substituted alkyl. In one embodiment, $R^{11}$ is an amino substituted alkyl.

Deprotection of the 3'-OH Protecting Groups

In some embodiments, the 3'-OH protecting group is removed in a deprotecting reaction with a phosphine. The azido group in —C(R)$_2$N$_3$ can be converted to an amino group by contacting the modified nucleotide or nucleoside molecules with a phosphine. Alternatively, the azido group in —C(R)$_2$N$_3$ may be converted to an amino group by contacting such molecules with the thiols, in particular water-soluble thiols such as dithiothreitol (DTT). In one embodiment, the phosphine is tris(hydroxymethyl)phosphine (THP). Unless indicated otherwise, the reference to nucleotides is also intended to be applicable to nucleosides.

Detectable Labels

Some embodiments described herein relate to the use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11):4593-4602, 1987) and Smith et al. (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

Multiple labels can also be used in the present application, for example, bi-fluorophore FRET cassettes (*Tet. Let.* 46:8867-8871, 2000). Multi-fluor dendrimeric systems (*J. Am. Chem. Soc.* 123:8101-8108, 2001) can also be used. Although fluorescent labels are preferred, other forms of detectable labels will be apparent as useful to those of ordinary skill in the art. For example, microparticles, including quantum dots (Empodocles et al., *Nature* 399:126-130, 1999), gold nanoparticles (Reichert et al., *Anal. Chem.* 72:6025-6029, 2000) and microbeads (Lacoste et al., *Proc. Natl. Acad. Sci USA* 97(17):9461-9466, 2000) can all be used.

Multi-component labels can also be used in the present application. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

Unless indicated otherwise, the reference to nucleotides is also intended to be applicable to nucleosides. The present application will also be further described with reference to DNA, although the description will also be applicable to RNA, PNA, and other nucleic acids, unless otherwise indicated.

Linkers

In some embodiments described herein, the purine or pyrimidine base of the modified nucleotide or nucleoside molecules can be linked to a detectable label as described above. In some such embodiments, the linkers used are cleavable. The use of a cleavable linker ensures that the label can, if required, be removed after detection, avoiding any interfering signal with any labeled nucleotide or nucleoside incorporated subsequently.

In some other embodiments, the linkers used are non-cleavable. Since in each instance where a labeled nucleotide of the invention is incorporated, no nucleotides need to be subsequently incorporated and thus the label need not be removed from the nucleotide.

Those skilled in the art will be aware of the utility of dideoxynucleoside triphosphates in so-called Sanger sequencing methods, and related protocols (Sanger-type), which rely upon randomized chain-termination at a particular type of nucleotide. An example of a Sanger-type sequencing protocol is the BASS method described by Metzker.

Sanger and Sanger-type methods generally operate by the conducting of an experiment in which eight types of nucleotides are provided, four of which contain a 3'-OH group; and four of which omit the OH group and which are labeled differently from each other. The nucleotides used which omit the 3'-OH group-dideoxy nucleotides (ddNTPs). As known by one skilled in the art, since the ddNTPs are labeled differently, by determining the positions of the terminal nucleotides incorporated, and combining this information, the sequence of the target oligonucleotide may be determined.

The nucleotides of the present application, it will be recognized, may be of utility in Sanger methods and related protocols since the same effect achieved by using ddNTPs may be achieved by using the 3'-OH protecting groups described herein: both prevent incorporation of subsequent nucleotides.

Moreover, it will be appreciated that monitoring of the incorporation of 3'-OH protected nucleotides may be determined by use of radioactive $^{32}$P in the phosphate groups attached. These may be present in either the ddNTPs themselves or in the primers used for extension.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidizing agents, light, temperature, enzymes etc. The linker as discussed herein may also be cleaved with the same catalyst used to cleave the 3'-O-protecting group bond. Suitable linkers can be adapted from standard chemical protecting groups, as disclosed in Greene & Wuts, Protective Groups in Organic Synthesis, John Wiley & Sons. Further suitable cleavable linkers used in solid-phase synthesis are disclosed in Guillier et al. (*Chem. Rev.* 100:2092-2157, 2000).

The use of the term "cleavable linker" is not meant to imply that the whole linker is required to be removed from, e.g., the nucleotide base. Where the detectable label is attached to the base, the nucleoside cleavage site can be located at a position on the linker that ensures that part of the linker remains attached to the nucleotide base after cleavage.

Where the detectable label is attached to the base, the linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytosine, thymidine or uracil and the N-4 position on cytosine.

A. Electrophilically Cleaved Linkers

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system.

The use of thiophilic metals, such as nickel, silver or mercury, in the cleavage of thioacetal or other sulfur-containing protecting groups can also be considered for the preparation of suitable linker molecules.

B. Nucleophilic Ally Cleaved Linkers

Nucleophilic cleavage is also a well recognised method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

C. Photocleavable Linkers

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenzyl compounds and nitroveratryl compounds. Linkers based on benzoin chemistry can also be used (Lee et al., *J. Org. Chem.* 64:3454-3460, 1999).

D. Cleavage Under Reductive Conditions

There are many linkers known that are susceptible to reductive cleavage. Catalytic hydrogenation using palladium-based catalysts has been used to cleave benzyl and benzyloxycarbonyl groups. Disulfide bond reduction is also known in the art.

E. Cleavage Under Oxidative Conditions

Oxidation-based approaches are well known in the art. These include oxidation of p-alkoxybenzyl groups and the oxidation of sulfur and selenium linkers. The use of aqueous iodine to cleave disulfides and other sulfur or selenium-based linkers is also within the scope of the invention.

F. Safety-Catch Linkers

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., *J. Org. Chem.* 62:5165-5168, 1997).

G. Cleavage by Elimination Mechanisms

Elimination reactions can also be used. For example, the base-catalysed elimination of groups such as Fmoc and cyanoethyl, and palladium-catalysed reductive elimination of allylic systems, can be used.

In some embodiments, the linker can comprise a spacer unit. The length of the linker is unimportant provided that the label is held a sufficient distance from the nucleotide so as not to interfere with any interaction between the nucleotide and an enzyme.

In some embodiments, the linker may consist of the similar functionality as the 3'-OH protecting group. This will make the deprotection and deprotecting process more efficient, as only a single treatment will be required to remove both the label and the protecting group. Particularly preferred linkers are phosphine-cleavable azide containing linkers.

Sequencing Methods

The modified nucleosides or nucleotides described herein can be used in conjunction with a variety of sequencing techniques. In some embodiments, the process to determine the nucleotide sequence of a target nucleic acid can be an automated process.

The nucleotide analogues presented herein can be used in a sequencing procedure, such as a sequencing-by-synthesis (SBS) technique. Briefly, SBS can be initiated by contacting the target nucleic acids with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); *Ronaghi, Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. Nos. 7,595,883, and 7,244,559, each of which is incorporated herein by reference.

Sequencing-by-ligation reactions are also useful including, for example, those described in Shendure et al. *Science* 309:1728-1732 (2005); U.S. Pat. Nos. 5,599,675; and 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference. In both sequencing-by-ligation and sequencing-by-hybridization procedures, nucleic acids that are present in gel-containing wells (or other concave features) are subjected to repeated cycles of oligonucleotide delivery and detection. Fluidic systems for SBS methods as set forth herein, or in references cited herein, can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference.

EXAMPLES

Additional embodiments are disclosed in further detail in the following examples, which are not in any way intended to limit the scope of the claims. The synthesis of various modified nucleotide with protected 3'-hydroxy group are demonstrated in Examples 1-3.

Example 1

Synthesis of Nucleotides with 3'-OH Protecting Group

Scheme 1.

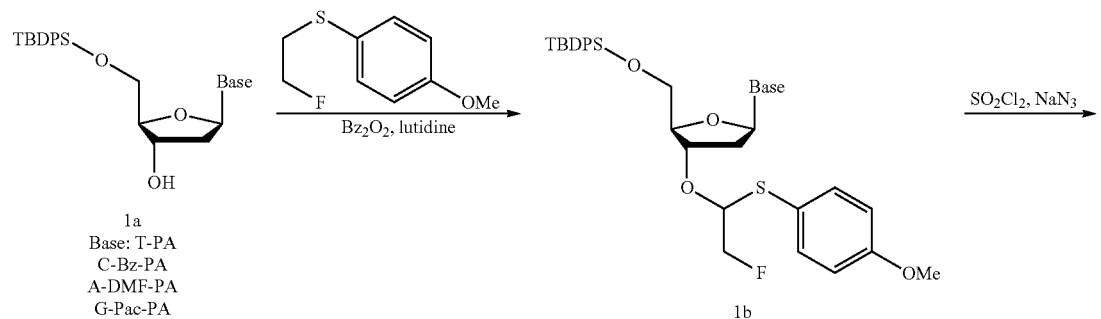

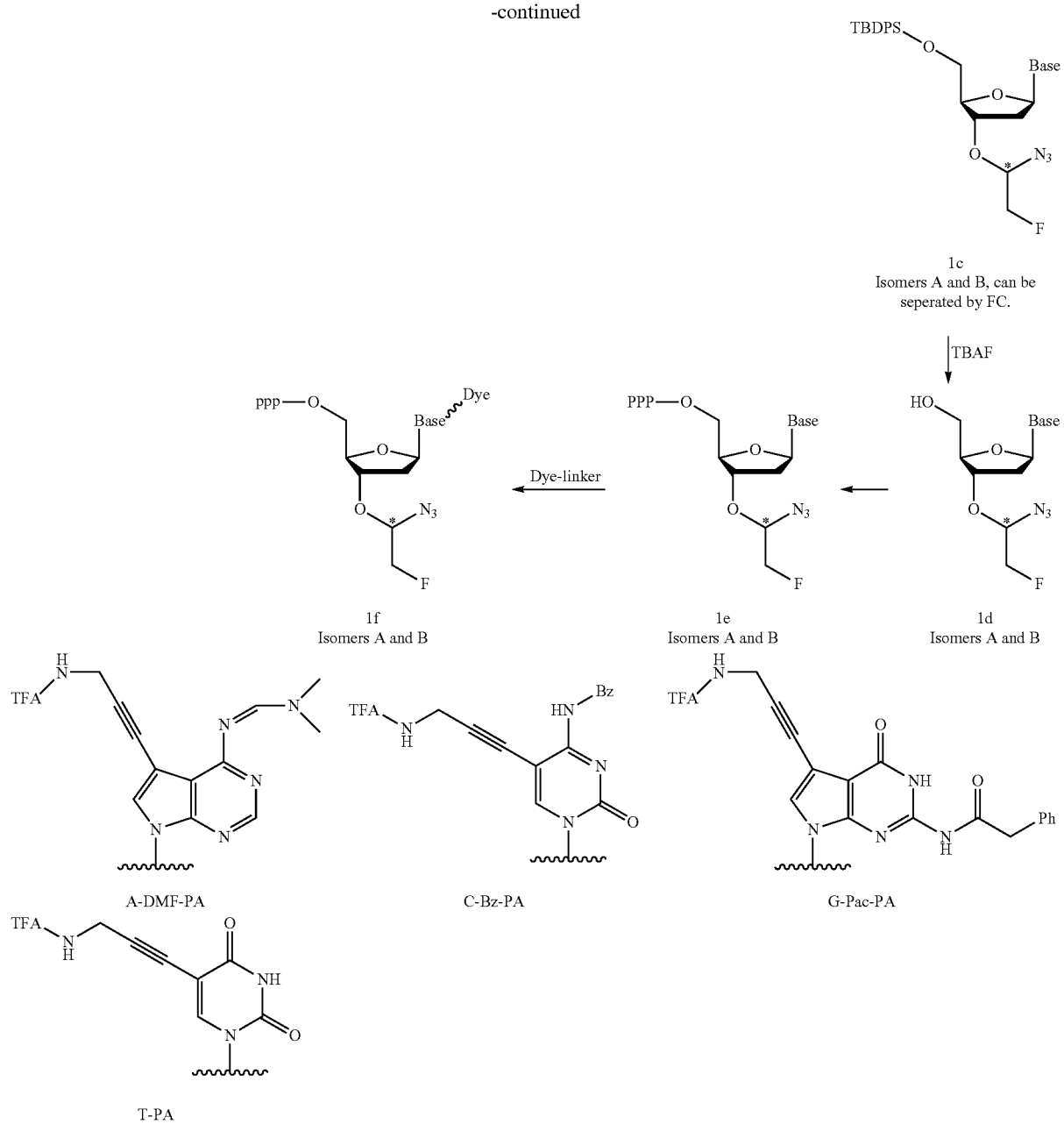

Scheme 1 illustrates a synthetic route for the preparation of the modified nucleotides with monofluoromethyl substituted azidomethyl as 3'-OH protecting groups. Compounds 1a-1f employ a modified thymine (T-PA) as the base. Other non-limiting examples of the bases that can be used include Cbz-PA, ADMF-PA, and GPac-PA, the structures of which are shown above in Scheme 1.

Experimental Procedures

To a solution of the starting nucleoside 1a (1.54 g, 2.5 mmol) in anhydrous $CH_3CN$ (25 ml) was added 2,6-lutidine (0.87 mL, 7.5 mmol), (2-fluoroethyl)(4-methoxyphenyl)sulfane (MPSF) (3.26 g, 17.5 mmol) and then $Bz_2O_2$ (50% pure, 8.47 g, 17.5 mmol) at 4° C. The reaction mixture was allowed to warm up slowly to room temperature. The mixture was stirred for other 6 hours. TLC monitored (EtOAc:DCM=2:8 v/v) to see complete consumption of the starting nucleoside. The reaction was then concentrated under reduced pressure to oily residue. To this mixture, petroleum ether (500 ml) was added and stirred vigorously for 10 min. The petroleum ether layer was decanted and the residue was repeated to treat with petroleum ether (×2). The oily residue was partitioned between $DCM/NaHCO_3$ (1:1) (300 mL). The organic layer was separated and the aqueous was further extracted into DCM (2×150 mL). Combined organic layers were dried over $MgSO_4$, filtered and the volatiles evaporated under reduced pressure. Crude product 1c was purified by Biotag silica gel column (50 g) using a gradient of petroleum ether to petroleum ether:EtOAc 1:1 (v/v) to afford 1.63 g nucleoside 1b as a pale yellow foam (diastereomers, 82% yield). $^1H$ NMR ($d_6$ DMSO, 400

MHz): δ, 0.95 (s, 9H, tBu), 2.16-2.28 (m, 2H, H-2'), 3.67 (s, OMe), 3.65-3.85 (m, 2H, HH-5'), 3.77 (dd, J=11.1, 4.5 Hz, 1H, HH-5'), 3.95-3.98 (m, 1H, H-4'), 4.04 (m, 2H, CH$_2$F), 4.63-4.64 (m, 1H, H-3'), 5.01-5.32 (s, 1H, CH), 6.00 (m, 1H, H-1'), 6.72-6.87 (m, 3H, Ar), 7.35-7.44 (m, 7H, Ar), 7.55-7.60 (m, 4H, Ar), 7.88 (s, 1H, H-6), 9.95 (brt, 1H, NH), 11.70 (s, 1H, NH).

To a solution of the starting nucleoside 1b (1.14 g, 1.4 mmol) in anhydrous CH$_2$C$_{12}$ (14 mL) with molecular sieve (4 Å) under N$_2$ was added cyclohexene (1.44 mL, 14 mmol). The mixture was cooled with a dry ice/acetone bath to −78° C. The solution of sulfuryl chloride (580 μL, 7.2 mmol) in DCM (14 ml) was slowly added over 90 minutes under N$_2$. After 20 mins at that temperature TLC (EtOAc:petroleum ether=1:1 v/v) indicated the full consumption of the starting nucleoside. Volatiles were evaporated under reduced pressure (and room temperature of 25° C.) and the oily residue was quickly subjected to high vacuum for a further 10 minutes until it foamed. The crude product was purged with N$_2$ and then dissolved in anhydrous DMF (5 mL) and NaN$_3$ (470 mg, 7 mmol) added at once. The resulting suspension was stirred at room temperature for 2 hours or until TLC indicated the completion of the reaction and formation of 1c as two isomer (a and b) The reaction mixture was partitioned between EtOAc:NaHCO$_3$ (1:1) (200 mL). The organic layer was separated and the aqueous was further extracted into EtOAc (2×100 mL). Combined organic extracts were dried over MgSO$_4$, filtered and the volatiles evaporated under reduced pressure. The two diastereoisomers of 1c (A and B) were separated by Biotag silica gel column (25 g) using a gradient of petroleum ether to petroleum ether:EtOAc 1:1 (v/v) as pale yellow foam.

Isomer A (370 mg, yield: 38%). $^1$H NMR (d$_6$ DMSO, 400 MHz): δ 1.02 (s, 9H, tBu), 2.35-2.43 (m, 2H, H-2'), 3.76-3.80 (m, 1H, H-5'), 3.88-3.92 (m, 1H, H-5'), 4.10-4.12 (m, 1H, H-4'), 4.14 (d, J=4.1 Hz 2H, NHCH$_2$), 4.46-4.60 (m, 3H, H-3', CH$_2$F), 5.05-5.09 (m, 1H, CHN$_3$), 6.11 (t, J=6.1 Hz, 1H, H-1'), 7.47-7.51 (m, 6H, Ar), 7.64-7.68 (m, 4H, Ar), 7.97 (s, 1H, H-6), 10.03 (bt, 1H, J=10.0 Hz, NH), 11.76 (s, 1H, NH). $^{19}$F NMR: −74.3 (CF$_3$), −230.2 (CH$_2$F).

Isomer B (253 mg, yield: 26%). $^1$H NMR (d$_6$ DMSO, 400 MHz): δ 1.01 (s, 9H, tBu), 2.38-2.42 (m, 2H, H-2'), 3.74-3.78 (m, 1H, H-5'), 3.86-3.90 (m, 1H, H-5'), 4.00-4.05 (m, 1H, H-4'), 4.12 (d, J=4.1 Hz 2H, NHCH$_2$), 4.45-4.60 (m, 3H, H-3', CH$_2$F), 5.00-5.14 (m, 1H, CHN$_3$), 6.09 (t, J=6.1 Hz, 1H, H-1'), 7.41-7.50 (m, 6H, Ar), 7.63-7.66 (m, 4H, Ar), 7.95 (s, 1H, H-6), 10.01 (bs, 1H, NH), 11.74 (s, 1H, NH). $^{19}$F NMR: −74.5 (CF$_3$), −230.4 (CH$_2$F).

The starting material 1c (isomer A) (500 mg, 0.71 mmol) was dissolved in THF (3 mL) and cooled to 4° C. in ice-bath. Then TBAF (1.0 M in THF, 5 wt. % water, 1.07 mL, 1.07 mmol) was added slowly over a period of 5 mins. The reaction mixture was slowly warmed up to room temperature. Reaction progress was monitored by TLC (petroleum ether:EtOAc 3:7 (v/v)). The reaction was stopped after 1 hour when no more starting material was visible by TLC. The reaction solution was dissolved in EtOAc (50 mL) and added to NaHCO$_3$ (60 mL). The two layers were separated and the aqueous layer was extracted with additional DCM (50 mL×2). The organic extractions were combined, dried (MgSO$_4$), filtered, and evaporated to give a yellow oil. Crude product 1d (isomer A) was purified by Biotag silica gel column (10 g) using a gradient of petroleum ether:EtOAc 8:2 (v/v) to EtOAc as a white solid (183 mg, yield: 56%).

Isomer A: $^1$H NMR (400 MHz, d$_6$-DMSO): δ 2.24-2.35 (m, 2H, H-2'), 3.56-3.66 (m, 2H, H-5'), 3.96-4.00 (m, 1H, H-4'), 4.23 (s, 2H, CH$_2$NH), 4.33-4.37 (m, 1H, H-3'), 4.43-4.51 (m, CH$_2$F), 5.12 (br.s, 1H, CHN$_3$), 5.23 (br.s, 1H, 5'-OH), 6.07 (t, J=6.7 Hz, 1H, H-1'), 8.26 (s, 1H, H-6), 10.11 (br s, 1H, NH), 11.72 (br s, 1H, NH). $^{19}$F NMR: −74.3 (CF$_3$), −230.5 (CH$_2$F)

The same reaction was performed for 1c (isomer B) at 360 mg scale and afforded the corresponding product 1d (Isomer B, 150 mg, 63%). $^1$H NMR (400 MHz, d$_6$-DMSO): δ 2.24-2.37 (m, 2H, H-2'), 3.57-3.70 (m, 2H, H-5'), 3.97-4.01 (m, 1H, H-4'), 4.23 (br.s, 2H, CH$_2$NH), 4.33-4.37 (m, 1H, H-3'), 4.44-4.53 (m, CH$_2$F), 5.11-5.21 (br.s, 1H, CHN$_3$), 5.23 (br.s, 1H, 5'-OH), 6.07 (t, J=6.6 Hz, 1H, H-1'), 8.23 (s, 1H, H-6), 10.09 (br s, 1H, NH), 11.70 (br s, 1H, NH). $^{19}$F NMR: −74.1 (CF$_3$), −230.1 (CH$_2$F).

The preparation of the corresponding triphosphates 1e and the further attachment of dye to the nucleobase to afford the fully functional nucleoside triphosphate (ffN) if have been reported in WO 2004/018497 and are generally known by one skilled in the art.

Example 2

Synthesis of Nucleotides with 3'-OH Protecting Group

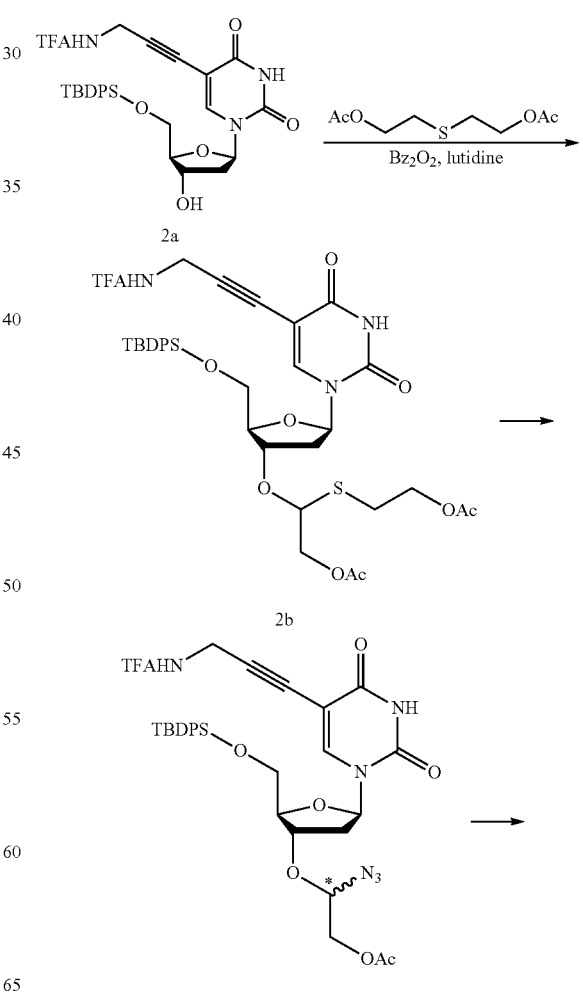

Scheme 2.

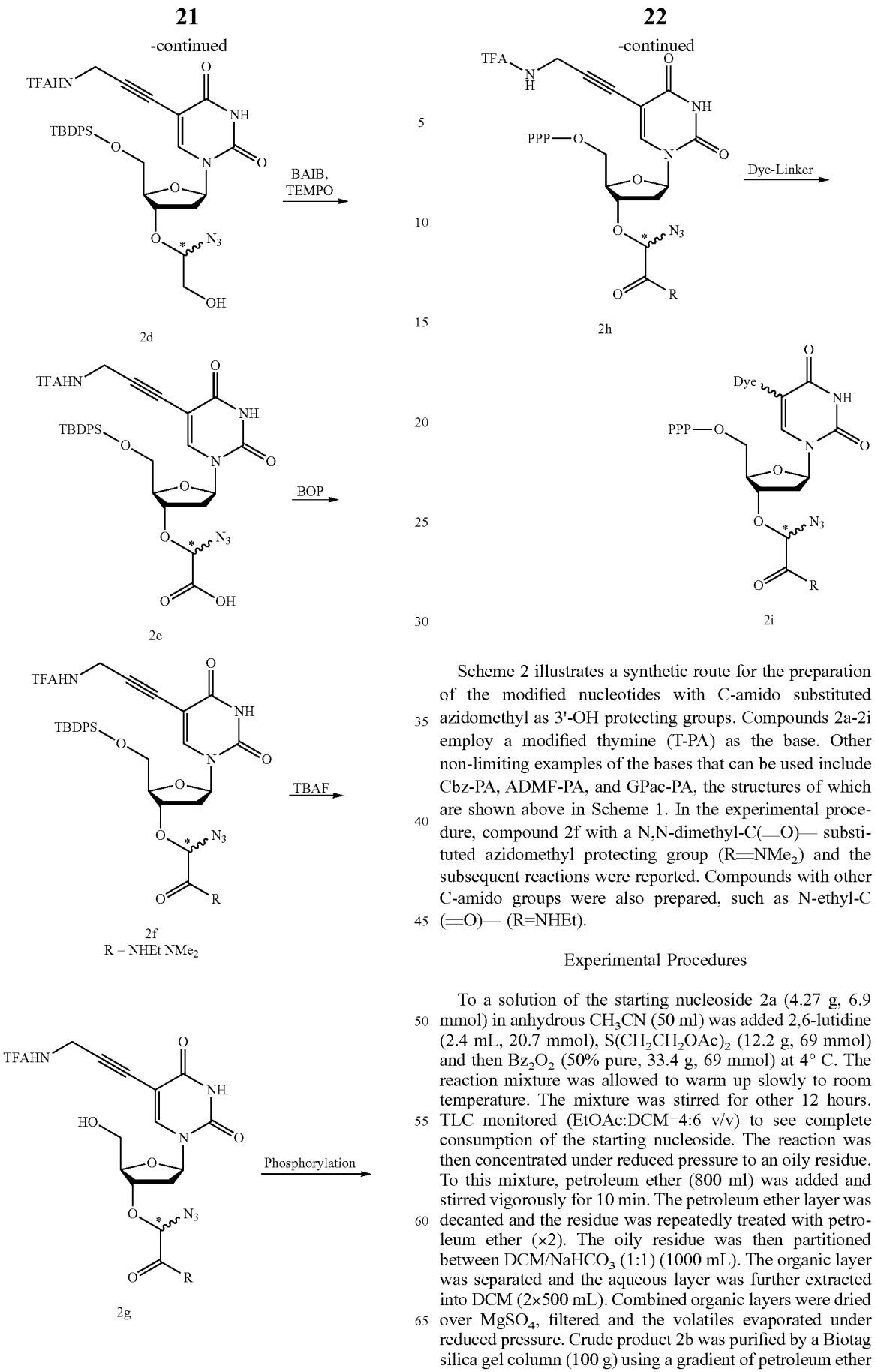

Scheme 2 illustrates a synthetic route for the preparation of the modified nucleotides with C-amido substituted azidomethyl as 3'-OH protecting groups. Compounds 2a-2i employ a modified thymine (T-PA) as the base. Other non-limiting examples of the bases that can be used include Cbz-PA, ADMF-PA, and GPac-PA, the structures of which are shown above in Scheme 1. In the experimental procedure, compound 2f with a N,N-dimethyl-C(=O)— substituted azidomethyl protecting group (R=NMe$_2$) and the subsequent reactions were reported. Compounds with other C-amido groups were also prepared, such as N-ethyl-C (=O)— (R=NHEt).

Experimental Procedures

To a solution of the starting nucleoside 2a (4.27 g, 6.9 mmol) in anhydrous CH$_3$CN (50 ml) was added 2,6-lutidine (2.4 mL, 20.7 mmol), S(CH$_2$CH$_2$OAc)$_2$ (12.2 g, 69 mmol) and then Bz$_2$O$_2$ (50% pure, 33.4 g, 69 mmol) at 4° C. The reaction mixture was allowed to warm up slowly to room temperature. The mixture was stirred for other 12 hours. TLC monitored (EtOAc:DCM=4:6 v/v) to see complete consumption of the starting nucleoside. The reaction was then concentrated under reduced pressure to an oily residue. To this mixture, petroleum ether (800 ml) was added and stirred vigorously for 10 min. The petroleum ether layer was decanted and the residue was repeatedly treated with petroleum ether (×2). The oily residue was then partitioned between DCM/NaHCO$_3$ (1:1) (1000 mL). The organic layer was separated and the aqueous layer was further extracted into DCM (2×500 mL). Combined organic layers were dried over MgSO$_4$, filtered and the volatiles evaporated under reduced pressure. Crude product 2b was purified by a Biotag silica gel column (100 g) using a gradient of petroleum ether to petroleum ether:EtOAc 2:8 (v/v) as a pale yellow foam (4.17 g, yield: 74%, diastereoisomers).

To a solution of the starting nucleoside 2b (4.54 g, 5.56 mmol) in anhydrous $CH_2C_{12}$ (56 mL) with molecular sieve (4 Å) under $N_2$ was added cyclohexene (5.62 mL, 56 mmol). The mixture was cooled with an ice bath to 4° C. The solution of sulfuryl chloride (1.13 mL, 13.9 mmol) in DCM (25 ml) was slowly added over 90 minutes under $N_2$. After 30 min at that temperature TLC (EtOAc:DCM=4:6 v/v) indicated 10% of the starting nucleoside 2b was left. Additional sulfuryl chloride (0.1 mL) was added into reaction mixture. TLC indicated complete conversion of 2b. Volatiles were evaporated under reduced pressure (and room temperature of 25° C.) and the oily residue was quickly subjected to a high vacuum for a further 10 minutes until it foamed. The crude product was purged with $N_2$ and then dissolved in anhydrous DMF (5 mL) and $NaN_3$ (1.8 g, 27.8 mmol) added at once. The resulting suspension was stirred at room temperature for 2 hours or until TLC indicated the completion of the reaction and formation of 2c as two isomers (A and B). The reaction mixture was partitioned between EtOAc:$NaHCO_3$ (1:1) (1000 mL). The organic layer was separated and the aqueous layer was further extracted into EtOAc (2×300 mL). Combined organic extracts were then dried over $MgSO_4$, filtered and the volatiles evaporated under reduced pressure. The two diastereoisomers 2c (isomer A and B) were separated by a Biotag silica gel column (100 g) using a gradient of petroleum ether to petroleum ether:EtOAc 1:1 (v/v) as pale yellow foam. Isomer A: 1.68 g, yield: 40.7%. Isomer B: 1.79 g, yield: 43.2%.

To a solution of the starting nucleoside 2c (isomer A) (1.63 g, 2.2 mmol) in MeOH/THF (1:1) (20 mL) was slowly added NaOH (1M in water) (2.2 mL, 2.2 mmol) and stirred in 4° C. The reaction progress was monitored by TLC (EtOAc:DCM=4:6 v/v). The reaction was stopped after 1 hour when no more starting material was visible by TLC. The reaction mixture was partitioned between DCM:$NaHCO_3$ (1:1) (150 mL). The organic layer was separated and the aqueous layer was further extracted into DCM (2×70 mL). Combined organic extracts were dried over $MgSO_4$, filtered and the volatiles evaporated under reduced pressure. The crude product 2d was purified by a Biotag silica gel column (10 g) using a gradient of petroleum ether:EtOAc (8:2) (v/v) to EtOAc as a pale yellow foam (1.1 g, yield: 71%).

The same reaction was repeated for 2c (isomer B, 1.57 g) and afforded the corresponding product 2d (isomer B, 1.01 g, 69% yield).

To a solution of the starting nucleoside 2d (isomer A) (700 mg, 1 mmol) in $CH_3CN$ (10 mL) was treated with TEMPO (63 mg, 0.4 mmol) and BAIB (644 mg, 2 mmol) at room temperature. The reaction progress was monitored by TLC (EtOAc:DCM=7:3 v/v). The reaction was stopped after 2 hour when no more starting material was visible by TLC. The reaction mixture was partitioned between DCM: $Na_2S_2O_3$ (1:1) (100 mL). The organic layer was separated and the aqueous layer was further extracted into DCM (2×70 mL). Combined organic extracts were then washed with NaCl (sat.). The organic layer was evaporated under reduced pressure without drying over $MgSO_4$ in order to prevent the product from precipitating out. The crude product 2e was purified by a Biotag silica gel column (10 g) using a gradient of petroleum ether:EtOAc (1:1) (v/v) to EtOAc to MeOH: EtOAc (1:9) as a pale yellow foam (isomer A, 482 mg, 68% yield).

The same reaction was performed for 2d (isomer B, 700 mg) and afforded the corresponding product 2e (isomer B, 488 mg, 69% yield).

To a solution of the starting nucleoside 2e (isomer A) (233 mg, 0.33 mmol) in $CH_3CN$ (10 mL) was added Hunig's base (173 µL, 1 mmol) and BOP (165 mg, 0.39 mmol) at room temperature. After stirring for 5 min, the solution was treated with Me2NH (2 M in THF) (0.41 ml, 0.82 mmol). The reaction progress was monitored by TLC (MeOH:DCM=1:9 v/v). The reaction was stopped after 2 hours when no more starting material was visible by TLC. The reaction mixture was partitioned between DCM:$NaHCO_3$ (1:1) (50 mL). The organic layer was separated and the aqueous layer was further extracted into DCM (2×30 mL). Combined organic extracts were dried over $MgSO_4$, filtered and the volatiles evaporated under reduced pressure. The crude product 2f (R=$NMe_2$) was purified by a Biotag silica gel column (10 g) using a gradient of DCM:EtOAc (8:2) (v/v) to EtOAc as a pale yellow foam (isomer A, 220 mg, 90% yield).

The same reaction was performed for 2e (isomer B, 249 mg) and afforded the corresponding product 2f (isomer B, 240 mg, 92% yield).

The starting material 2f (mixture of isomer A and B) (455 mg, 0.61 mmol) was dissolved in THF (2 mL) and cooled to 4° C. with ice-bath. Then, TBAF (1.0 M in THF, 5 wt. % water, 1.0 mL, 1.0 mmol) was added slowly over a period of 5 min. The reaction mixture was slowly warmed up to room temperature. The reaction progress was monitored by TLC (EtOAc). The reaction was stopped after 1 hour when no more starting material was visible by TLC. The reaction solution was dissolved in DCM (30 mL) and added to $NaHCO_3$ (30 mL). The two layers were separated and the aqueous layer was extracted with additional DCM (30 mL×2). The organic extractions were combined, dried ($MgSO_4$), filtered, and evaporated to give a yellow oil. Crude product 2 g was purified by a Biotag silica gel column (10 g) using a gradient of DCM:EtOAc 8:2 (v/v) to EtOAc to MeOH:EtOAc (2:8) as a white solid (52% yield, 160 mg).

The preparation of the corresponding triphosphates 2h and the further attachment of dye to the nucleobase to afford the fully functional nucleoside triphosphate (ffN) 2i have been reported in WO 2004/018497 and are generally known by one skilled in the art.

Example 3
Synthesis of Nucleotides with 3'-OH Protecting Group
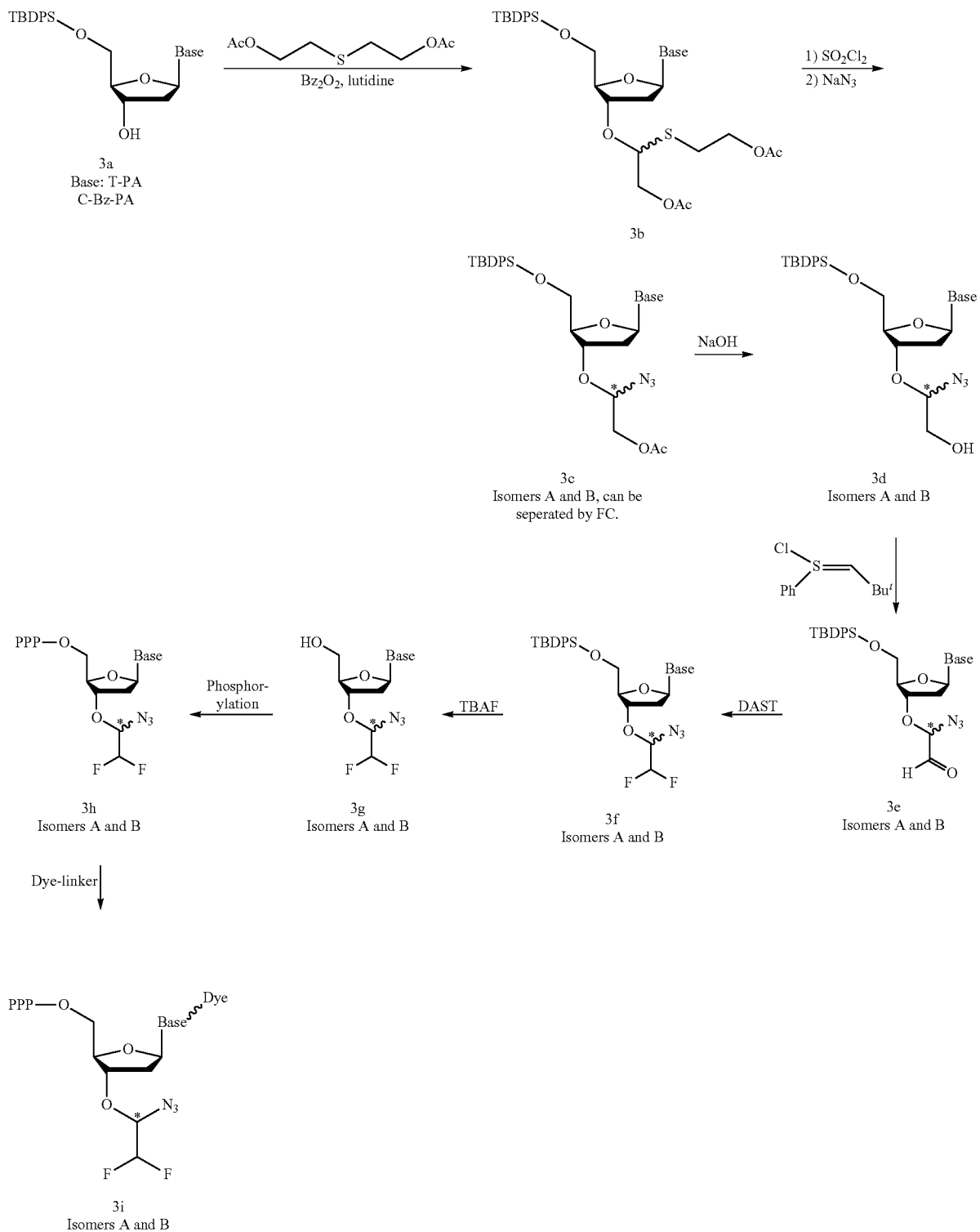

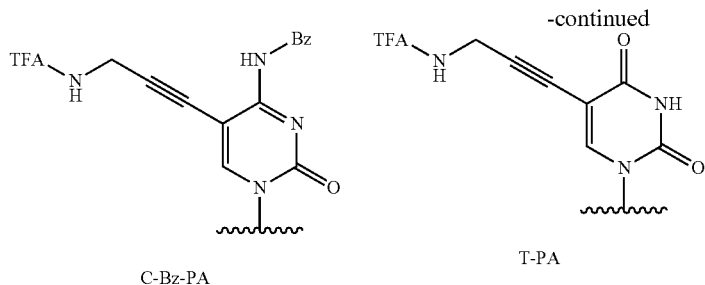

C-Bz-PA

T-PA

Scheme 3 illustrates a synthetic route for the preparation of modified nucleotides with difluoromethyl substituted azidomethyl 3'-OH protecting groups. Compounds 3a-3i employ a modified thymine (T-PA) as the base. Other non-limiting examples of the bases that can be used include Cbz-PA, ADMF-PA, and GPac-PA, the structures of which are shown above in Scheme 1. The procedure for the synthesis of 3b, 3c and 3d were described in Example 2.

Experimental Procedures

To a solution of the starting nucleoside 3d (isomer A) (490 mg, 0.7 mmol) and DBU (209 µL, 1.4 mmol) in anhydrous DCM (5 mL) was added slowly a solution of N-tert-butyl benzene sulfinimidoyl chloride (181 mg, 0.84 mmol) in anhydrous DCM (2 ml) at −78° C. The reaction mixture was stirred for 2 h at −78° C. The reaction progress was monitored by TLC (EtOAc:DCM 4:6 v/v). The reaction was stopped after 2 hours when there was still 10% starting material left by TLC, to prevent over-reacting. The reaction mixture was partitioned between DCM:NaHCO$_3$ (1:1) (50 mL). The aqueous layer was further extracted into DCM (2×30 mL). The organic extractions were combined, dried (MgSO$_4$), filtered, and evaporated to give a yellow oil. The crude product 3e was purified by a Biotag silica gel column (10 g) using a gradient of petroleum ether:EtOAc (8:2) (v/v) to petroleum ether:EtOAc (2:8) (v/v) as a pale yellow foam (isomer A, 250 mg, 51% yield).

The same reaction was performed for 3d (isomer B, 480 mg) and afforded the corresponding product 3e (isomer B, 240 mg, 50% yield).

To a solution of the starting nucleoside 3e (isomer A) (342 mg, 0.49 mmol), EtOH (15 µL, 0.25 mmol) in DCM (2.5 mL) was added slowly to the solution of DAST (181 mg, 0.84 mmol) in DCM (2.5 mL) at 4° C. (ice bath). The reaction mixture was stirred for 1 h at 4° C. The reaction progress was monitored by TLC (EtOAc:petroleum ether=3:7 v/v). The reaction was stopped after 1 hour. The reaction mixture was partitioned between DCM:NaHCO$_3$ (1:1) (50 mL). The aqueous layer was further extracted into DCM (2×30 mL). The organic extractions were combined, dried (MgSO$_4$), filtered, and evaporated to give a yellow oil. The crude product 3f was purified by a Biotag silica gel column (10 g) using a gradient of petroleum ether:EtOAc (9:1) (v/v) to petroleum ether:EtOAc (2:8) (v/v) as a pale yellow foam (isomer A, 100 mg, 28%).

The same reaction was performed for 3e (isomer B, 480 mg) and afforded the corresponding product 3f (isomer B, 240 mg, 50% yield).

The starting material 3f (isomer A) (124 mg, 0.17 mmol) was dissolved in THF (2 mL) and cooled to 4° C. with an ice bath. Then, TBAF (1.0 M in THF, 5 wt. % water, 255 µL, 10.255 mmol) was added slowly over a period of 5 min. The reaction mixture was slowly warmed up to room temperature. The reaction progress was monitored by TLC (EtOAc). The reaction was stopped after 1 hour when no more starting material was visible by TLC. The reaction solution was dissolved in DCM (30 mL) and added to NaHCO$_3$ (30 mL). The two layers were separated and the aqueous layer was extracted with additional DCM (30 mL×2). The organic extractions were combined, dried (MgSO$_4$), filtered, and evaporated to give a yellow oil. Crude product 3 g was purified by a Biotag silica gel column (4 g) using a gradient of DCM:EtOAc 8:2 (v/v) to EtOAc to MeOH:EtOAc (2:8) as a pale yellow foam (isomer A, 54% yield, 44 mg).

Isomer A: $^1$H NMR (400 MHz, d$_6$-DMSO): δ 2.24-2.35 (m, 2H, H-2'), 3.56-3.66 (m, 2H, H-5'), 3.96-4.00 (m, 1H, H-4'), 4.23 (s, 2H, CH$_2$NH), 4.33-4.37 (m, 1H, H-3'), 4.85 (s, 2H, OCH$_2$N$_3$), 5.23 (t, J=5.1 Hz, 1H, 5'-OH), 6.07 (t, J=6.7 Hz, 1H, H-1'), 8.19 (s, 1H, H-6), 10.09 (br s, 1H, NH), 11.70 (br s, 1H, NH). $^{19}$F NMR: −74.4 (CF$_3$), −131.6 (CH$_2$F).

The same reaction was performed for 3f (isomer B, 133 mg) and afforded the corresponding product 3 g (isomer B, 48 mg, 54% yield). $^1$H NMR (400 MHz, d$_6$-DMSO): δ 2.27-2.44 (m, 2H, H-2'), 3.58-3.67 (m, 2H, H-5'), 4.00-4.02 (m, 1H, H-4'), 4.24 (d, J=4.1 Hz, 2H, CH$_2$NH), 4.57-4.58 (m, 1H, H-3'), 5.24-5.29 (m, 2H, 5'-OH, OCHN$_3$), 6.07-6.34 (m, 2H, H-1', CHF$_2$), 8.19 (s, 1H, H-6), 10.09 (br s, 1H, NH), 11.70 (br s, 1H, NH). $^{19}$F NMR: −74.2 (CF$_3$), −131.4 (CH$_2$F).

The preparation of the corresponding triphosphates 3h and the further attachment of dye to the nucleobase to afford the fully functional nucleotide (ffN) 3i have been reported in WO 2004/018497 and are generally known by one skilled in the art.

Example 4

Thermal Stability Testing of the 3'-OH Protecting Groups

Figure 1B:
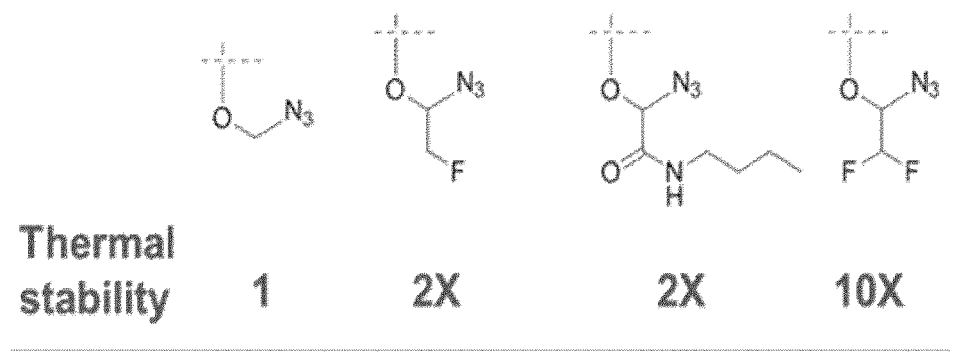
FIG. 1B illustrated the thermal stability of various 3'-OH protecting groups.

A variety of 3'-OH protecting groups were investigated in regard to their thermal stability (FIG. 1A). The thermal stability was evaluated by heating 0.1 mM of each 3'-OH protected nucleotide in a pH=9 buffer (tis-HCl 50 mM, NaCl 50 mM, tween 0.05%, Mg$_2$SO$_4$ 6 mM) at 60° C. Various times points were taken and HPLC was used to analyze the formation of un-blocked materials. The stabilities of —CH$_2$F and —C(O)NHBu were found to be about 2-fold greater than the standard azidomethyl (—CH$_2$N$_3$) protecting group. The stability of —CF$_2$H group was found to be about 10-fold greater than the standard (FIG. 1B).

Example 5

Deprotection of the 3'-OH Protecting Groups

Figures 2A, 2B:
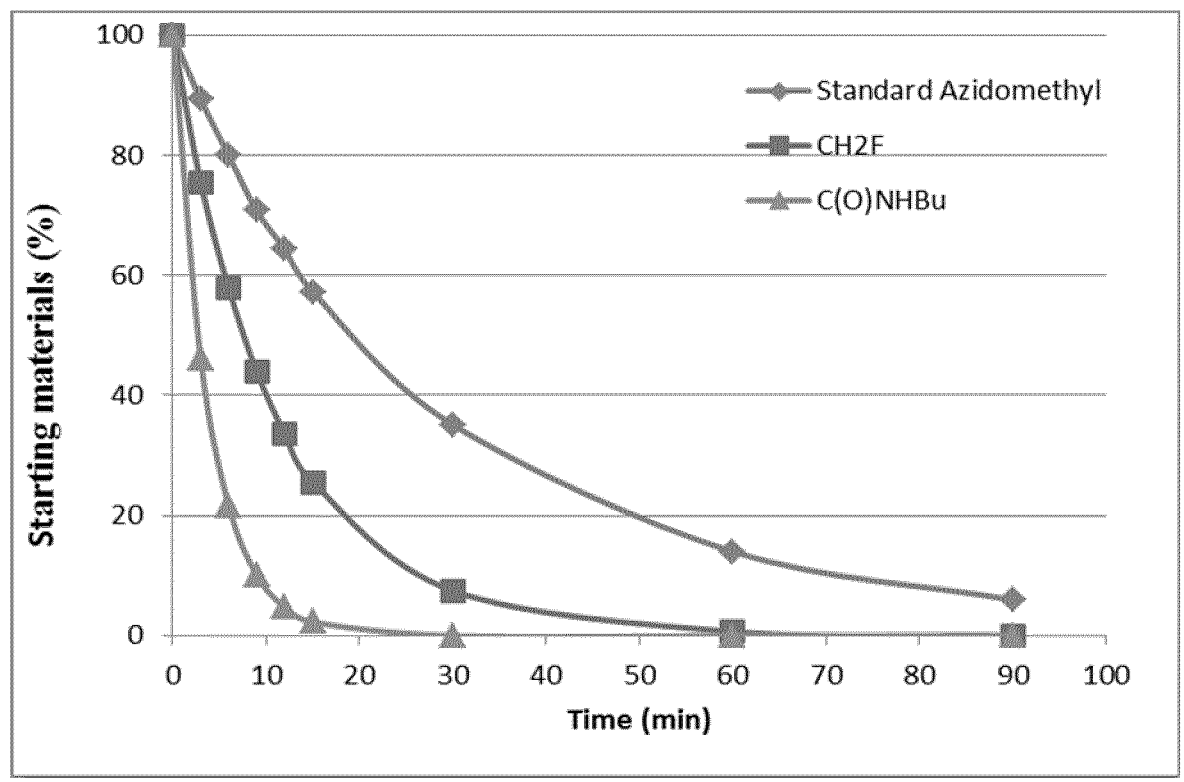
FIG. 2A illustrates the deprotection rate curve of three different 3'-OH protecting groups.
FIG. 2B shows a chart of the deprotection half time of three different 3'-OH protecting groups.

The deprotecting reaction rates of several 3'-OH protecting groups were also studied. The deprotection rate of the standard azidomethyl protecting group was compared with the —CH₂F substituted azidomethyl and —C(O)NHBu substituted azidomethyl. It was observed that both of the more thermally stable 3'-OH blocking groups were removed faster than the standard azidomethyl protecting group using phosphines (1 mM THP) as the deprotecting agent. See FIG. 2A. For example, the half-life of —CH₂F and —C(O)NHBu was 8.9 minutes and 2.9 minutes respectively, compared to the 20.4 minutes half-life of azidomethyl (FIG. 2B).

Example 6

Sequencing Test

Modified nucleotides with —CH₂F (mono-F) substituted azidomethyl 3'-OH protecting group were prepared and their sequencing performance was evaluated on Miseq platforms. It was envisaged that increased thermal stability of 3'-OH protecting groups would lead to a higher quality of nucleotides for sequencing chemistry with less contaminated 3'-unblocked nucleotides. The presence of 3'-unblocked nucleotides in the SBS-sequencing kits would therefore result in pre-phasing events, which were numerated as pre-phasing values.

Figure 3:
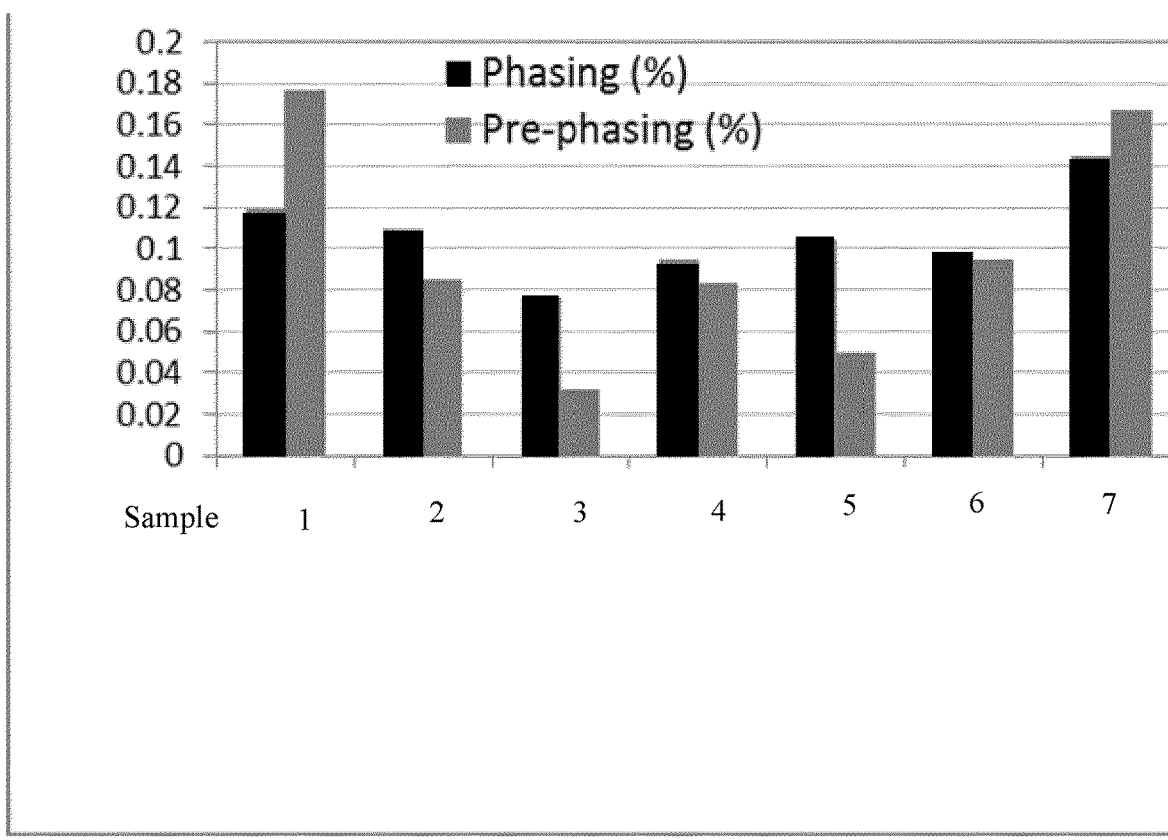
FIG. 3 shows the phasing and prephasing values of various modified nucleotide with a thermally stable 3'-OH protecting group in comparison and the standard protecting group.

Short 12-cycle sequencing experiments were first used to generate phasing and pre-phasing values. Mono-F substituted azidomethyl protected ffNs were used according to the following concentration: ffA-dye 1 (2 uM); ffT-dye 2 (10 uM), ffC-dye 3 (2 uM) and ffG-dye 4 (5 uM). Mono-F substituted azidomethyl group comprises both isomer A and B. Two dyes—dye 2 as in standard Miseq kits and dye 5 were used to label ffT. Table 1 shows various nucleotide combinations with A and B isomers of mono-F substituted azidomethyl that were evaluated in regard to phasing and pre-phasing impacts. In all cases, the pre-phasing values were substantially lower than the control that standard V2 Miseq kits nucleotides used (FIG. 3).

TABLE 1-continued

| Sample | 3'-OH Protecting Group | Phasing (%) | Pre-phasing (%) |
|---|---|---|---|
| 3 | Mono-F-A isomer (ffT-Dye 5) | 0.076 | 0.032 |
| 4 | Mono-F-A isomer (A, C and G) + Mono-F-B-ffT-Dye 5 | 0.095 | 0.083 |
| 5 | Mono-F-A (G, ffT-Dye 5) and Mono-F-B (A, C) | 0.104 | 0.05 |
| 6 | Mono-F-A (G, T) and Mono-F-B (A, C) | 0.098 | 0.095 |
| 7 | Std Miseq V2 IMX control | 0.145 | 0.167 |

Sequencing Quality Testing

2×400 bp sequencing was carried out on Miseq to evaluate the potential of these nucleotides for sequencing quality improvement. The sequencing run was performed according to manufacturer's instructions (Illumina Inc., San Diego, Calif.). The standard incorporation buffer was replaced with an incorporation buffer containing all mono-F blocked FFNs, each with a separate dye label: ffA-dye 1 (2 uM), ffT-dye 2 (1 uM), ffC-dye 3 (2 uM) and ffG-dye 4 (5 uM). The DNA library used was made following the standard TruSeq HT protocol from *B. cereus* genomic DNA.

Figure 4A:
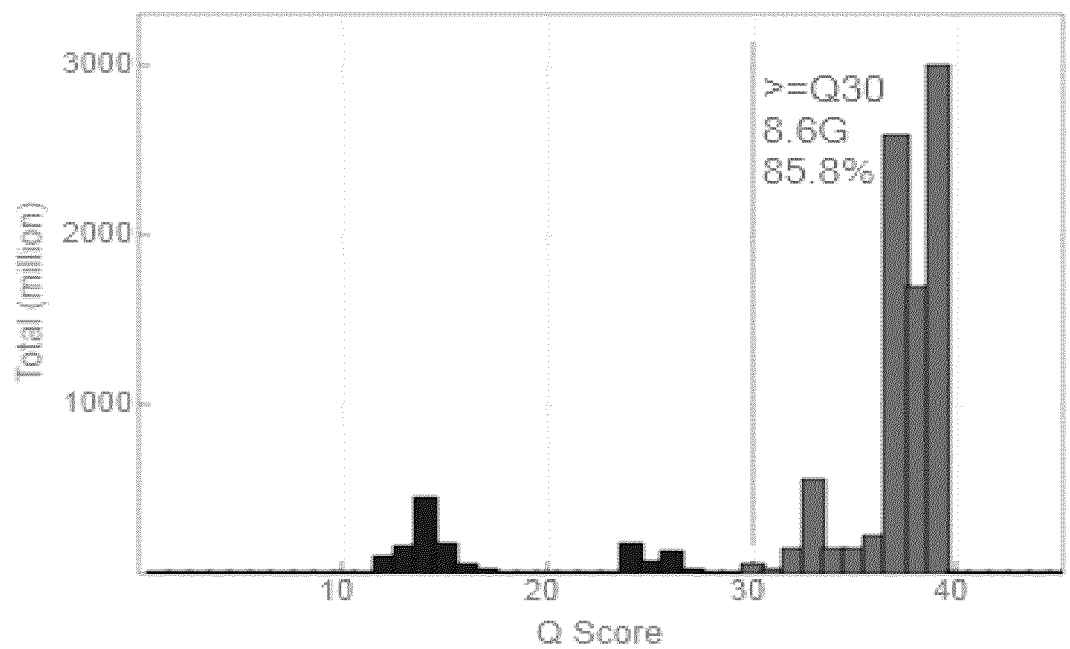
FIG. 4A shows the 2×400 bp sequencing data of mono-F ffNs-A-isomer in incorporation mix (IMX).
Figure 4B:
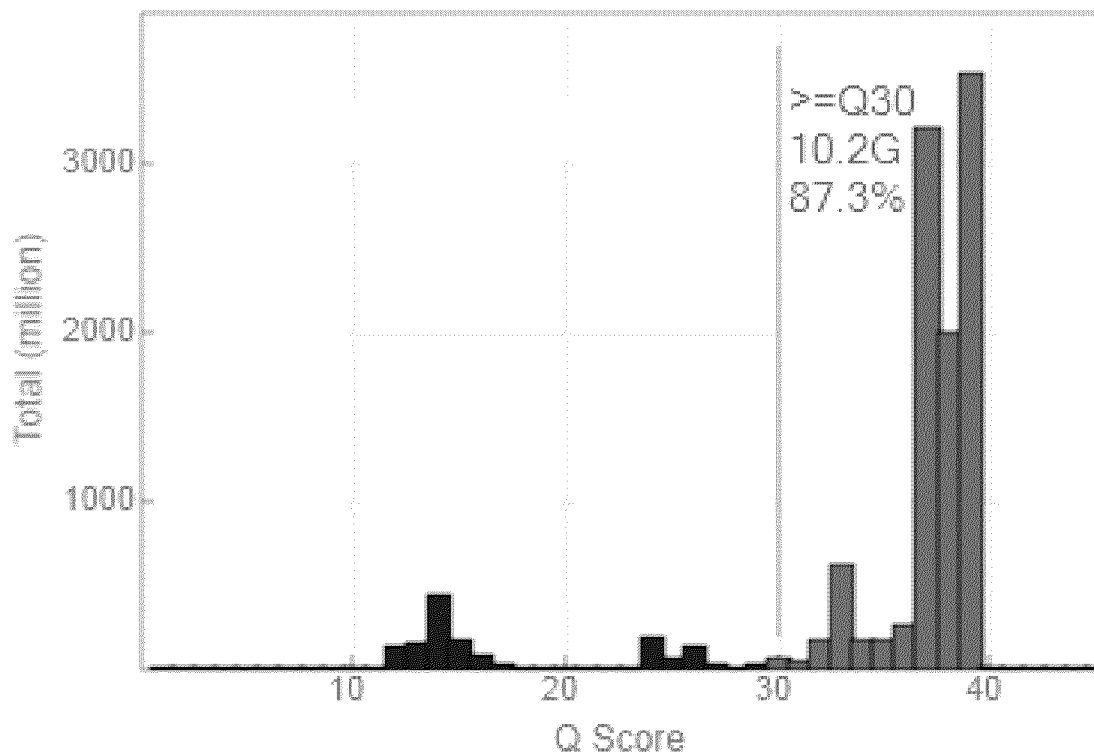
FIG. 4B shows the 2×400 bp sequencing data of mono-F ffNs-B-isomer in incorporation mix (IMX).

In both sequencing experiments (with mono-F block A and B isomer), very low pre-phasing values were observed. Coupled with low phasing values, application of these new nucleotides has generated superior 2×400 bp sequencing data with >80% of bases above Q30 in both cases (see FIG. 4A for the Q score of isomer A and FIG. 4B for the Q score chart of isomer B). These results demonstrate a great improvement compared with Miseq v2 kits (2×250 bp, 80% bases>Q30 in a typical R&D sequencing experiments, or 70% bases >Q30 as the stated specs). As shown below, Table 2 summarizes the sequencing data when using all mono-F ffNs-A-isomer in IMX. Table 3 summarizes the sequencing data using all mono-F ffNs-B-isomer in IMX.

TABLE 2

| Lane | Tiles | Density (K/mm2) | Clusters PF (%) | Phas/Prephas (%) | Reads (M) | Reads PF (M) | % Mismatch Rate (PF) | % >= Q30 | Yield Total (G) |
|---|---|---|---|---|---|---|---|---|---|
| R1 | 28 | 690 +/− 14 | 93.1 +/− 0.7 | 0.075/0.051 | 13.35 | 12.43 | 0.58 ± 0.11 | 89.7 | 5 |
| R2 | 28 | 690 +/− 14 | 93.1 +/− 0.7 | 0.092/0.078 | 13.35 | 12.43 | 1.31 ± 0.25 | 81.9 | 5 |
| Total | | | | | | | | 85.8 | 9.9 |

TABLE 3

| Lane | Tiles | Density (K/mm2) | Clusters PF (%) | Phas/Prephas (%) | Reads (M) | Reads PF (M) | % Mismatch Rate (PF) | % >= Q30 | Yield Total (G) |
|---|---|---|---|---|---|---|---|---|---|
| R1 | 28 | 816 +/− 9 | 92.7 +/− 0.6 | 0.073/0.033 | 15.79 | 14.64 | 0.44 ± 0.11 | 91.2 | 5.9 |
| R2 | 28 | 816 +/− 9 | 92.7 +/− 0.6 | 0.078/0.059 | 15.79 | 14.64 | 1.03 ± 0.19 | 83.4 | 5.9 |
| Total | | | | | | | | 87.3 | 11.7 |

TABLE 1

| Sample | 3'-OH Protecting Group | Phasing (%) | Pre-phasing (%) |
|---|---|---|---|
| 1 | Std Miseq V2 IMX control | 0.119 | 0.177 |
| 2 | Mono-F-A-isomer | 0.11 | 0.085 |

What is claimed is:

1. A modified nucleotide triphosphate comprising a nucleobase and a 2-deoxyribose sugar moiety having a removable 3'-hydroxy protecting group forming a structure —O—CH(R)N₃ covalently attached to the 3'-carbon atom, wherein R is selected from the group consisting of —$C(R^1)_m(R^2)_n$, —$C(=O)OR^3$, —$C(=O)NR^4R^5$, —$C(R^6)_2O(CH_2)_p NR^7R^8$ and —$C(R^9)_2$O-Ph-$C(=O)NR^{10}R^{ii}$;

$R^1$ is hydrogen, or optionally substituted alkyl;

$R^2$ is halogen;

$R^3$ is hydrogen or optionally substituted alkyl;

each of $R^4$ and $R^5$ is independently selected from the group consisting of hydrogen, optionally substituted alkyl, optionally substituted aryl, optionally substituted heteroaryl, and optionally substituted aralkyl;

each of $R^6$ and $R^9$ is selected from the group consisting of hydrogen, optionally substituted alkyl and halogen;

each of $R^7$, $R^8$, $R^{10}$ and $R^{11}$ is independently selected from the group consisting of hydrogen, optionally substituted alkyl, optionally substituted aryl, optionally substituted heteroaryl, and optionally substituted aralkyl;

m is an integer of 1 or 2;

n is an integer of 1 or 2; provided that m+n is equal to 3; and p is an integer of 0 to 6.

2. The modified nucleotide triphosphate of claim 1, wherein R is —$CHF_2$, —$CH_2F$, —$CHCl_2$ or —$CH_2Cl$.

3. The modified nucleotide triphosphate of claim 2, wherein R is —$CH_2F$ or —$CHF_2$.

4. The modified nucleotide triphosphate of claim 3, wherein the nucleobase is deazapurine, cytosine, thymine, or uracil.

5. The modified nucleotide triphosphate of claim 1, wherein R is —$C(=O)NR^4R^5$ and wherein $R^4$ is hydrogen and $R^5$ is $C_{1-6}$ alkyl.

6. The modified nucleotide triphosphate of claim 5, wherein $R^5$ is t-butyl.

7. The modified nucleotide triphosphate of claim 5, wherein the nucleobase is deazapurine, cytosine, thymine, or uracil.

8. The modified nucleotide triphosphate of claim 1, wherein said nucleotide is linked to a detectable label via a cleavable linker.

9. The modified nucleotide triphosphate of claim 7, wherein the cleavable linker is attached to the nucleobase.

10. The modified nucleotide triphosphate of claim 9, wherein the cleavable linker is attached via the 7-position of the deazapurine, or the 5-position of the cytosine, thymine, or uracil.

11. The modified nucleotide triphosphate of claim 8, wherein the cleavable linker comprises azido group.

12. The modified nucleotide triphosphate of claim 8, wherein the cleavable linker and the 3'-hydroxy protecting group are cleavable in a single step of chemical reaction.

13. A method of preparing a growing polynucleotide complementary to a target single-stranded polynucleotide in a sequencing reaction, comprising:

incorporating a modified nucleotide triphosphate of claim 1 into a growing complementary polynucleotide, wherein the incorporation of the modified nucleotide prevents the introduction of any subsequent nucleotide into the growing complementary polynucleotide.

14. The method of claim 13, wherein the incorporation of the modified nucleotide is accomplished by a terminal transferase, a terminal polymerase or a reverse transcriptase.

15. A method of determining the sequence of a target single-stranded polynucleotide, comprising (a) incorporating a modified nucleotide triphosphate of claim 8 into a growing complementary polynucleotide, wherein the incorporation of the modified nucleotide prevents the introduction of any subsequent nucleotide into the growing complementary polynucleotide;

(b) detecting the identity of the modified nucleotide incorporated; and (c) removing the 3'-hydroxy protecting group and the detectable label prior to introducing the next complementary nucleotide.

16. The method of claim 15, wherein the incorporation of the modified nucleotide is accomplished by a terminal polymerase.

17. The method of claim 15, wherein the identity of the modified nucleotide is determined by detecting the detectable label.

18. The method of claim 15, wherein the 3'-hydroxy protecting group and the detectable label are removed in a single step of chemical reaction.

19. The method of claim 15, wherein steps (a)-(c) are repeated multiple times.

20. A kit comprising one or more modified nucleotide triphosphate of claim 1.

21. The kit of claim 20, wherein the modified nucleotide is linked to a detectable label via a cleavable linker.

* * * * *

UNITED STATES PATENT AND TRADEMARK OFFICE
CERTIFICATE OF CORRECTION

PATENT NO. : 10,982,277 B2
APPLICATION NO. : 16/563443
DATED : April 20, 2021
INVENTOR(S) : Xiaohai Liu Page 1 of 1

It is certified that error appears in the above-identified patent and that said Letters Patent is hereby corrected as shown below:

In the Specification

In Column 11, Line 2, delete "—C(R$^1$)$^m$(R$^2$)$_n$." and insert -- —C(R$^1$)$_m$(R$^2$)$_n$.--.

In Column 13, Line 37, delete "Nucleophilic Ally" and insert --Nucleophilically--.

In Column 19, Line 9, delete "CH$_2$C$_{12}$" and insert --CH$_2$Cl$_2$--.

In Column 20, Line 15 (Approx.), delete "if" and insert --1f--.

In Column 23, Line 4, delete "CH$_2$C$_{12}$" and insert --CH$_2$Cl$_2$--.

In Column 24, Line 22 (Approx.), delete "Me2NH" and insert --Me$_2$NH--.

In Column 30, Line 17, delete "(Illumina" and insert --(Illumina--.

In the Claims

In Column 31, Claim 1, Line 3, delete "—C(R$^9$)$_2$O-Ph-C(=O)NR$^{10}$R$^{ii}$;" and insert -- —C(R$^9$)$_2$O-Ph-C(=O)NR$^{10}$R$^{11}$;--.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*